(12) United States Patent
Malphettes et al.

(10) Patent No.: US 10,100,319 B2
(45) Date of Patent: Oct. 16, 2018

(54) COMPOSITIONS AND METHODS FOR REGULATING CELL OSMOLARITY

(71) Applicant: Genentech, Inc., South San Francisco, CA (US)

(72) Inventors: Laetitia Malphettes, Ixelles (BE); Andrew Snowden, Somerville, MA (US); Inn H. Yuk, Burlingame, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/549,962

(22) Filed: Nov. 21, 2014

(65) Prior Publication Data

US 2015/0307888 A1    Oct. 29, 2015

Related U.S. Application Data

(63) Continuation of application No. 13/063,912, filed as application No. PCT/US2009/057031 on Sep. 15, 2009.

(60) Provisional application No. 61/097,149, filed on Sep. 15, 2008.

(51) Int. Cl.
*C12N 15/67* (2006.01)
*C12N 15/63* (2006.01)

(52) U.S. Cl.
CPC .............. *C12N 15/67* (2013.01); *C12N 15/63* (2013.01); *C12N 2830/002* (2013.01)

(58) Field of Classification Search
None
See application file for complete search history.

(56) References Cited

U.S. PATENT DOCUMENTS

| 6,586,206 B1 | 7/2003 | Dixit et al. |
| 2011/0269233 A1 | 11/2011 | Malphettes et al. |

FOREIGN PATENT DOCUMENTS

| WO | 02/074801 | 9/2002 |
| WO | 2008/069496 | 6/2008 |

OTHER PUBLICATIONS

Appendix A Clustal Omega alignment of the TonEBP element of Seq ID No. 1 of the instant specification, against the human VWA7 gene, generated May 9, 2014.*
Appendix B List of transcription factors contained in the TRANSFAC database; http://www.gene-regulation.com/pub/databases/transfac/cISM.html; accessed May 10, 2014.*
Clustal Omega alignment of the TonEBP element of Seq ID No. 1, against the human VWA7 gene; downloaded from EMBL's Clustal Omega server; http://www.ebi.ac.ut/Tools/msa/clustalo (Generated May 9, 2014).
Clustal Omega alignment of the TonEBP element of Seq ID No. 1, against the human HSP70-2 gene; downloaded from EMBL's Clustal Omega server; http://www.ebi.ac.uk/Tools/msa/clustalo (Generated May 9, 2014).
Canadian Office Action issued in Canadian Patent Application No. 2,734,922, pp. 1-7 (Issued: Jan. 22, 2013).
Mexican Office Action issued in Mexican Patent Application No. MX/a/2011/002638, with WO ISR and Supplementary European Search Report (received on Aug. 22, 2012), pp. 1-4 ( Jul. 20, 2012).
Database ENA (online),'Mus musculus aquaporin-2 (Aqp2) gene, exons 1 through 4 and complete cds', retrieved from EBI, Database accession No. AY055468, pp. 1-4 ( Oct. 31, 2001).
Ely, M. et al., "Role of the AP-1 factors, c-Fos and c-Jun, in high NaCl-induced activation of the osmoprotective transcription factor, TonEBP/OREBP" The FASEB Journal 21:774.6 ( 2007).
EP 09813808.4 Examination Report, pp. 1-8 ( Jul. 15, 2013).
Fogolin et al., "Impact of Temperature Reduction and Expression of Yeast Pyruvate Carboxylase on hGM-CSF-producing CHO Cells" Journal of Biotechnology 109:179-191 ( 2004).
Go. W. et al., "NFAT5 TonEBP Mutant Mice Define Osmotic Stress as a Critical Feature of the Lymphoid Microenvironment" PNAS 101(29):10673-10678 (Jul. 20, 2004).
Hasler, U. et al., "Tonicity-Responsive Enhancers Binding Protein is an Essential Regulator of Aquaporin-2 Expression in Renal Collecting Duct Principal Cells" Journal of the American Society of Nephrology 17(6):1521-1531 (Jun. 2006).
Hess, J. et al., "AP-1 subunits: quarrel and harmony among siblings" Journal of Cell Science 117(25):5965-5973 (Dec. 31, 2004).
Irarrazabal, C. et al., "Activator protein-1 contributes to high NaCl-induced increase in tonicity-responsive enhancer/osmotic response element-binding protein transactivating activity" The Journal of Biological Chemistry 283(5):2554-2563 (Feb. 1, 2008).
Jeon, U. et al., "How Tonicity Regulates Genes: Story of TonEBP Transactional Activator" Acta Physiologica 187(1-2):241-247 (May 2006).
Klawitter et al., "A Metabonomic and Proteomic Analysis of Changes in IMCD3 Cells Chronically Adapted to Hypertonicity" Nephron Physiol 109:1-10 ( 2008).
Lander et al., "Initial Sequencing and Analysis of the Human Genome" Nature 409:860-921 ( 2001).
List of transcription factors contained in the TRANSFAC dabase; http://www.gene-regulation.com/pub/databases/trasfac/clSMlhtml (Accessed May 10, 2014).
Miyakawa, H. et al., "Tonicity-responsive enhancer binding protein, a Rel-like protein that stimulates transcription in response to hypertonicity" PNAS 96:2538-2542 (Mar. 31, 1999).
Na, K. et al., "Silencing of TonEBP/NFAT5 Transcriptional Activator by RNA Interference" Journal of the American Society of Nephrology 14(2):283-288 (Feb. 2003).

(Continued)

*Primary Examiner* — Addison D Ault
(74) *Attorney, Agent, or Firm* — Morrison and Foerster LLP

(57) ABSTRACT

The invention provides compositions and methods for regulating intracellular osmolarity in cells, e.g., in cultured cells, including in cultured cells in bioreactors. The invention provides nucleic acids comprising at least one osmo-responsive transcriptional regulatory element (OR-TRE), and cells, vectors, products of manufacture, artificial organs or implants and the like containing an osmo-responsive transcriptional regulatory element (OR-TRE).

5 Claims, 7 Drawing Sheets
Specification includes a Sequence Listing.

(56) References Cited

OTHER PUBLICATIONS

Rai, T. et al., "Cloning of rat and mouse aquaporin-2 gene promoters and identification of a negative cis-regulatory element" The American Journal of Physiology 273(2):F264-F273 (Aug. 1997).
Trama, J. et al., "The NFAT-Related Protein NFATL1 (TonEBP/NFAT5) is Induced Upon T Cell Activation in a Calcineurin-Dependent Manner" The Journal of Immunology 165:4884-4894 (2008).
Umayahara, Y. et al., "Estrogen regulation of the insulin-like growth factor I gene transcription involves an AP-1 enhancer" The Journal of Biological Chemistry 269(23):16433-16442 (1994).
Woo, S. et al., "Ton/EBP/NFAT5 Stimulates Transcription of HSP70 in Response to Hypertonicity" Molecular and Cellular Biology 22(16):5753-5760 (Aug. 2002).
Zharkikh, L. et al., "Renal principal cell-specific experession of green fluorescent protein in transgenic mice" The American Journal of Physiology. Renal Physiology 283(6):F1351-F1364 (Dec. 2002).
International Preliminary Report on Patentability, dated Mar. 15, 2011, for PCT/US2009/057031, filed Sep. 15, 2009, 7 pages.
International Search Report, dated May 10, 2010, for PCT/US2009/057031, filed Sep. 15, 2009, 3 pages.
Non-Final Office Action, dated Aug. 29, 2013, for U.S. Appl. No. 13/063,912, filed Jun. 17, 2011, 10 pages.
Non-Final Office Action, dated May 21, 2014, for U.S. Appl. No. 13/063,912, filed Jun. 17, 2011, 20 pages.
Daoudal et al. "Isolation of the Mouse Aldose Reductase Promoter and Identification of a Tonicity-Responsive Element," *Journal of Biological Chemistry* 272(5):2615-2619, (1997).
Fenton et al. "Structure and Characterization of the Mouse UT-A Gene (Slcl4a2),"*Am J Physiol. Renal Physiol.* 282(4):F630-F638. (2002, e-pub. Nov. 20, 2001).
Ferraris et al. "ORE, A Eukaryotic Minimal Essential Osmotic Response Element. The Aldose Reductase Gene in Hyperosmotic Stress," *J. Biol. Chem.* 271(31):18318-18321, (1996).
Ferraris et al. "Functional Consensus for Mammalian Osmotic Response Elements," *Am. J. Physiol.* 276(3 Pt 1):C667-C673, (1999).
Ko et al. "Identification and Characterization of Multiple Osmotic Response Sequences in the Human Aldose Reductase Gene," *J Biol Chem.* 272(26):16431-16437, (1997).
Li et al. "Calcineurin-NFATc Signaling Pathway Regulates AQP2 Expression in Response to Calcium Signals and Osmotic Stress," *Am J. Physiol. Cell. Physiol.* 292:C1606-C1616, (2007).
Lopez-Rodriguez et al. "NFAT5, a Constitutively Nuclear NFAT Protein That Does not Cooperate with Fos and Jun," *Proc. Natl. Acad. Sci. USA* 96:7214-7219, (1999).
Lopez-Rodriguez et al. "Bridging the NFAT and NFκB Families: NF ATS Dimerization Regulates Cytokine Gene Transcription in Response to Osmotic Stress," *Immunity* 15:4758, (2001).
Miyakawa et al. "Cis- and Trans-Acting Factors Regulating Transcription of the BGTL Gene in Response to Hypertonicity," *Am J Physiol.* 274(4 Pt 2):F753-F761, (1998).
Nagase et al. "Prediction of the Coding Sequences of Unidentified Human Genes. XII. The Complete Sequences of 100 New cDNA Clones From Brain Which Code for Large Proteins in Vitro," *DNA Res.* 5(6):355-364, (1998).
Rim et al. "Transcription of the Sodium/myo-lnositol Cotransporter Gene Is Regulated by Multiple Responsive Enhancers Spread Over Kilobase Pairs in the 5'-Flanking Region," *J. Biol. Chem.* 273(32):20615-20621, (1998).
Stroud et al. "Structure of a TonEBP-DNA Complex Reveals DNA Encircled by a Transcription Factor," *Nat. Struct. Biol.* 9(2):90-94, (2002, e-pub. Jan. 7, 2002).

\* cited by examiner

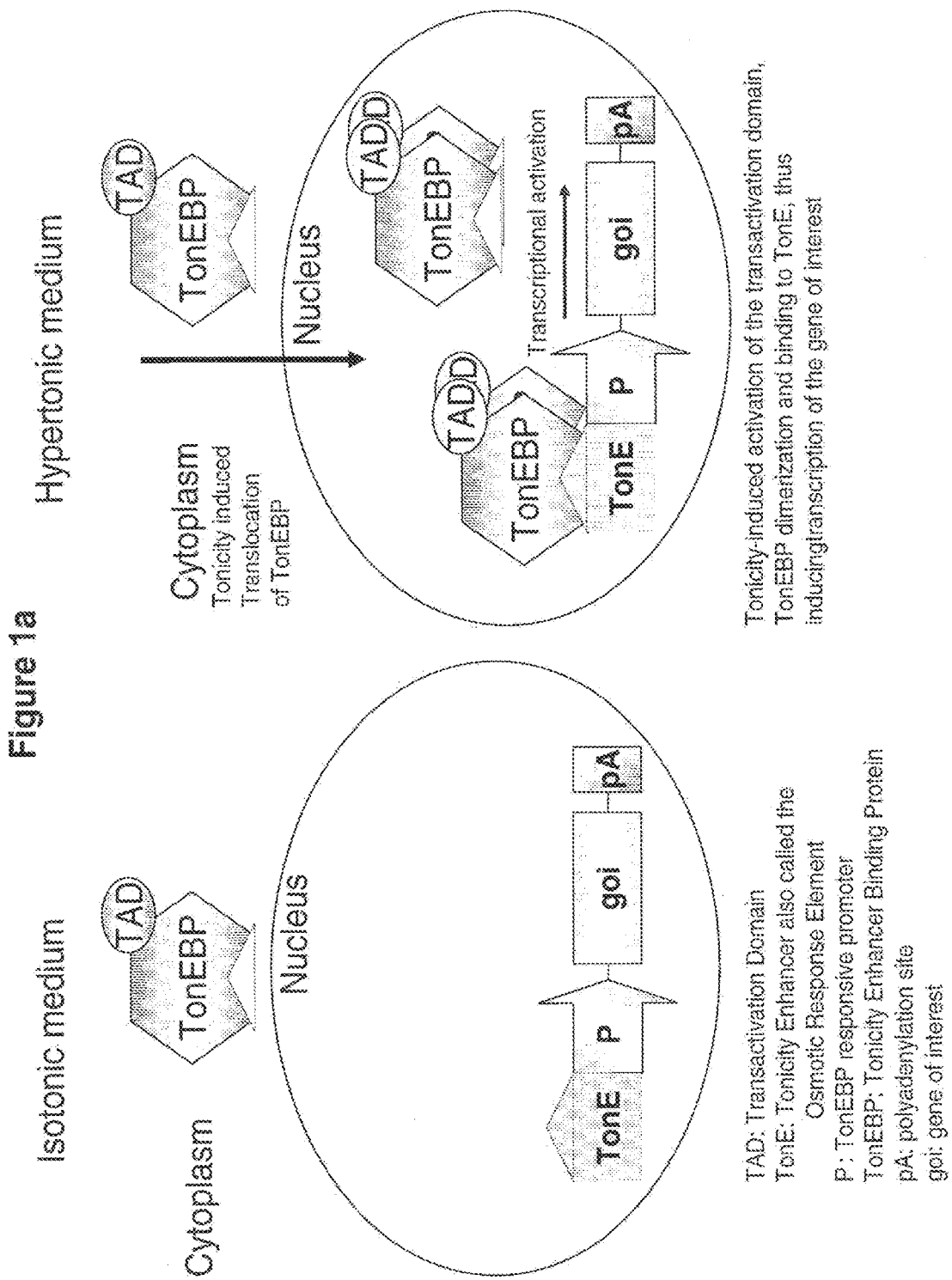

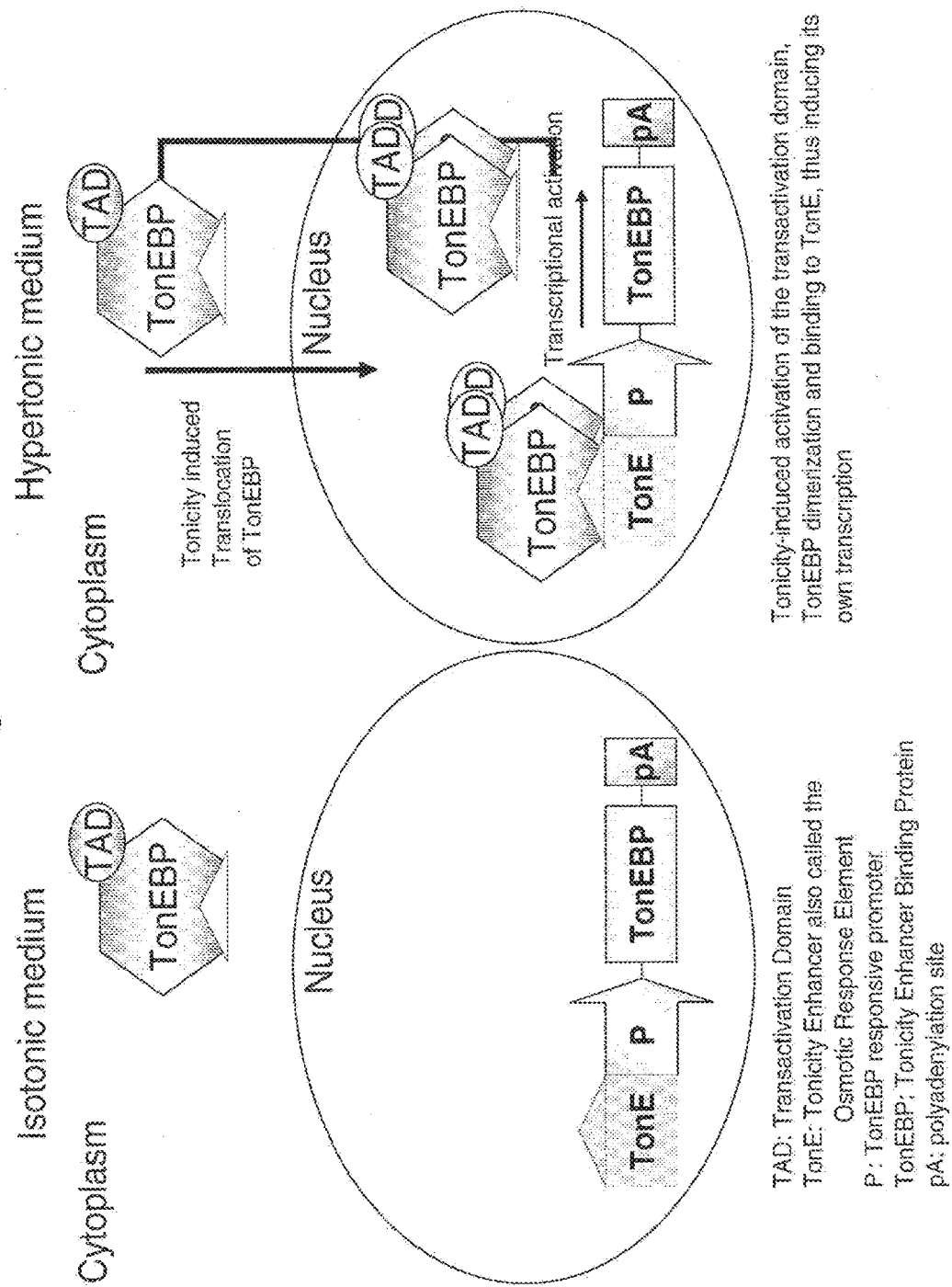

SEQUENCE LISTING

```
<160> NUMBER OF SEQ ID NOS: 41

<210> SEQ ID NO 1
<211> LENGTH: 11
<212> TYPE: DNA
<213> ORGANISM: Artificial Sequence
<220> FEATURE:
<223> OTHER INFORMATION: Recombinant construct consensus
<220> FEATURE:
<221> NAME/KEY: misc_feature
<222> LOCATION: 7, 8, 10
<223> OTHER INFORMATION: n = A,T,C or G

<400> SEQUENCE: 1
hggaawnnhn h                                                      11

<210> SEQ ID NO 2
<211> LENGTH: 7
<212> TYPE: DNA
<213> ORGANISM: Artificial Sequence
<220> FEATURE:
<223> OTHER INFORMATION: Consensus

<400> SEQUENCE: 2 hggaasr                                                            7

<210> SEQ ID NO 3
<211> LENGTH: 7
<212> TYPE: DNA
<213> ORGANISM: Artificial Sequence
<220> FEATURE:
<223> OTHER INFORMATION: Consensus

<400> SEQUENCE: 3
```

-continued tgastca                                                      7

<210> SEQ ID NO 4
<211> LENGTH: 11
<212> TYPE: DNA
<213> ORGANISM: Artificial Sequence
<220> FEATURE:
<223> OTHER INFORMATION: Consensus
<220> FEATURE:
<221> NAME/KEY: misc_feature
<222> LOCATION: 7, 8, 10
<223> OTHER INFORMATION: n = A,T,C or G

<400> SEQUENCE: 4
hggaaannhn h                                                 11

<210> SEQ ID NO 5
<211> LENGTH: 11
<212> TYPE: DNA
<213> ORGANISM: Artificial Sequence
<220> FEATURE:
<223> OTHER INFORMATION: Consensus

<400> SEQUENCE: 5
tggaaatttg t                                                 11

<210> SEQ ID NO 6
<211> LENGTH: 7
<212> TYPE: DNA
<213> ORGANISM: Artificial Sequence
<220> FEATURE:
<223> OTHER INFORMATION: Consensus

<400> SEQUENCE: 6 tgactca                                                      7

<210> SEQ ID NO 7
<211> LENGTH: 50
<212> TYPE: DNA
<213> ORGANISM: Artificial Sequence
<220> FEATURE:
<223> OTHER INFORMATION: Consensus

<400> SEQUENCE: 7
ttggaaaatc accagaatgg gatttagaga ggtgggttc ctgactcatt         50

<210> SEQ ID NO 8
<211> LENGTH: 106
<212> TYPE: DNA
<213> ORGANISM: Artificial Sequence
<220> FEATURE:
<223> OTHER INFORMATION: Consensus

<400> SEQUENCE: 8
ttgactagtt ggaaaatcac cagaatggga tttagagagg tggggttcct gactcattgc    60
tagctcgagc tcggtacccg ggtcgagtag gcgtgtacgg tgggag                 106

<210> SEQ ID NO 9
<211> LENGTH: 11
<212> TYPE: DNA
<213> ORGANISM: Artificial Sequence
<220> FEATURE:
<223> OTHER INFORMATION: Consensus

<400> SEQUENCE: 9
tggaaaatca c                                                          11

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
ggtggtttaa tcgatagaac c                                               21

<210> SEQ ID NO 11
<211> LENGTH: 11
<212> TYPE: DNA
<213> ORGANISM: Canis familiaris

<400> SEQUENCE: 11
tggaaaagtc c                                                          11

<210> SEQ ID NO 12
<211> LENGTH: 11
<212> TYPE: DNA
<213> ORGANISM: Homo sapiens

<400> SEQUENCE: 12
tggaaaaata t                                                          11

<210> SEQ ID NO 13
<211> LENGTH: 11
<212> TYPE: DNA
<213> ORGANISM: Homo sapiens

<400> SEQUENCE: 13
tggaaaaatt t                                                          11

<210> SEQ ID NO 14
<211> LENGTH: 11
<212> TYPE: DNA
<213> ORGANISM: Homo sapiens

<400> SEQUENCE: 14
tggaaaatca c                                                          11

<210> SEQ ID NO 15
<211> LENGTH: 11
<212> TYPE: DNA
<213> ORGANISM: Oryctolagus cuniculus

<400> SEQUENCE: 15
cggaaaatca c                                                          11

<210> SEQ ID NO 16
<211> LENGTH: 11
<212> TYPE: DNA
<213> ORGANISM: Mus musculus

<400> SEQUENCE: 16
tggaaaatca c                                                          11

<210> SEQ ID NO 17
<211> LENGTH: 11
<212> TYPE: DNA
<213> ORGANISM: Homo sapiens

<400> SEQUENCE: 17
tggaaaatta c                                                    11

<210> SEQ ID NO 18
<211> LENGTH: 11
<212> TYPE: DNA
<213> ORGANISM: Homo sapiens

<400> SEQUENCE: 18
tggaatatta c                                                    11

<210> SEQ ID NO 19
<211> LENGTH: 11
<212> TYPE: DNA
<213> ORGANISM: Homo sapiens

<400> SEQUENCE: 19
tggaaattta c                                                    11

<210> SEQ ID NO 20
<211> LENGTH: 11
<212> TYPE: DNA
<213> ORGANISM: Oryctolagus cuniculus

<400> SEQUENCE: 20
aggaaaatca c                                                    11

<210> SEQ ID NO 21
<211> LENGTH: 11
<212> TYPE: DNA
<213> ORGANISM: Oryctolagus cuniculus

<400> SEQUENCE: 21
cggaaaaaac c                                                    11

<210> SEQ ID NO 22
<211> LENGTH: 11
<212> TYPE: DNA
<213> ORGANISM: Oryctolagus cuniculus

<400> SEQUENCE: 22
cggaaaatac c                                                    11

<210> SEQ ID NO 23
<211> LENGTH: 11
<212> TYPE: DNA
<213> ORGANISM: Oryctolagus cuniculus

<400> SEQUENCE: 23
cggaaaatcc c                                                    11

<210> SEQ ID NO 24
<211> LENGTH: 11
<212> TYPE: DNA
<213> ORGANISM: Homo sapiens

<400> SEQUENCE: 24
tggaaaacta c                                                    11

<210> SEQ ID NO 25
<211> LENGTH: 11
<212> TYPE: DNA

```
<213> ORGANISM: Homo sapiens

<400> SEQUENCE: 25
atagaattcc a                                                        11

<210> SEQ ID NO 26
<211> LENGTH: 11
<212> TYPE: DNA
<213> ORGANISM: Homo sapiens

<400> SEQUENCE: 26
tggaattcta t                                                        11

<210> SEQ ID NO 27
<211> LENGTH: 12
<212> TYPE: DNA
<213> ORGANISM: Homo sapiens

<400> SEQUENCE: 27
tggaaaattc ca                                                       12

<210> SEQ ID NO 28
<211> LENGTH: 11
<212> TYPE: DNA
<213> ORGANISM: Homo sapiens

<400> SEQUENCE: 28
tggaaaatta c                                                        11

<210> SEQ ID NO 29
<211> LENGTH: 11
<212> TYPE: DNA
<213> ORGANISM: Homo sapiens

<400> SEQUENCE: 29
tggaaagtta c                                                        11

<210> SEQ ID NO 30
<211> LENGTH: 11
<212> TYPE: DNA
<213> ORGANISM: Homo sapiens

<400> SEQUENCE: 30
tggaaagttc c                                                        11

<210> SEQ ID NO 31
<211> LENGTH: 11
<212> TYPE: DNA
<213> ORGANISM: Mus musculus

<400> SEQUENCE: 31
tggaaagttt t                                                        11

<210> SEQ ID NO 32
<211> LENGTH: 11
<212> TYPE: DNA
<213> ORGANISM: Mus musculus

<400> SEQUENCE: 32
tggaaaattt t                                                        11

<210> SEQ ID NO 33
<211> LENGTH: 11
```

```
<212> TYPE: DNA
<213> ORGANISM: Mus musculus

<400> SEQUENCE: 33
tggaaatctc c                                                            11

<210> SEQ ID NO 34
<211> LENGTH: 11
<212> TYPE: DNA
<213> ORGANISM: Mus musculus

<400> SEQUENCE: 34
tggaaaaaca c                                                            11

<210> SEQ ID NO 35
<211> LENGTH: 11
<212> TYPE: DNA
<213> ORGANISM: Mus musculus

<400> SEQUENCE: 35
ggagttttcc a                                                            11

<210> SEQ ID NO 36
<211> LENGTH: 11
<212> TYPE: DNA
<213> ORGANISM: Mus musculus

<400> SEQUENCE: 36
tggaaaactc c                                                            11

<210> SEQ ID NO 37
<211> LENGTH: 1531
<212> TYPE: PRT
<213> ORGANISM: Mus musculus

<400> SEQUENCE: 37
```

Met Pro Ser Asp Phe Ile Ser Leu Leu Ser Ala Asp Leu Asp Leu Glu
 1               5                  10                  15

Ser Pro Lys Ser Leu Tyr Ser Arg Glu Ser Val Tyr Asp Leu Leu Pro
            20                  25                  30

Lys Glu Leu Gln Leu Pro Pro Ser Arg Glu Thr Ser Val Ala Ser Met
        35                  40                  45

Ser Gln Thr Ser Gly Gly Glu Ala Gly Ser Pro Pro Ala Val Val
    50                  55                  60

Ala Ala Asp Ala Ser Ser Ala Pro Ser Ser Ser Met Gly Gly Ala
65                  70                  75                  80

Cys Ser Ser Phe Thr Thr Ser Ser Ser Pro Thr Ile Tyr Ser Thr Ser
                85                  90                  95

Val Thr Asp Ser Lys Ala Met Gln Val Glu Ser Cys Ser Ser Ala Val
            100                 105                 110

Gly Val Ser Asn Arg Gly Val Ser Glu Lys Gln Leu Thr Ser Asn Thr
        115                 120                 125

Val Gln Gln His Pro Ser Thr Pro Lys Arg His Thr Val Leu Tyr Ile
    130                 135                 140

Ser Pro Pro Pro Glu Asp Leu Leu Asp Asn Ser Arg Met Ser Cys Gln
145                 150                 155                 160

Asp Glu Gly Cys Gly Leu Glu Ser Glu Gln Ser Cys Ser Met Trp Met
                165                 170                 175

Glu Asp Ser Pro Ser Asn Phe Ser Asn Met Ser Thr Ser Ser Tyr Asn

```
            180                 185                 190
Asp Asn Thr Glu Val Pro Arg Lys Ser Arg Lys Arg Asn Pro Lys Gln
            195                 200                 205

Arg Pro Gly Val Lys Arg Arg Asp Cys Glu Glu Ser Asn Met Asp Ile
    210                 215                 220

Phe Asp Ala Asp Ser Ala Lys Ala Pro His Tyr Val Leu Ser Gln Leu
225                 230                 235                 240

Thr Thr Asp Asn Lys Gly Asn Ser Lys Ala Gly Asn Gly Thr Leu Glu
                245                 250                 255

Asn Gln Lys Gly Thr Gly Val Lys Lys Ser Pro Met Leu Cys Gly Gln
            260                 265                 270

Tyr Pro Val Lys Ser Glu Gly Lys Glu Leu Lys Ile Val Val Gln Pro
    275                 280                 285

Glu Thr Gln His Arg Ala Arg Tyr Leu Thr Glu Gly Ser Arg Gly Ser
        290                 295                 300

Val Lys Asp Arg Thr Gln Gln Gly Phe Pro Thr Val Lys Leu Glu Gly
305                 310                 315                 320

His Asn Glu Pro Val Val Leu Gln Val Phe Val Gly Asn Asp Ser Gly
                325                 330                 335

Arg Val Lys Pro His Gly Phe Tyr Gln Ala Cys Arg Val Thr Gly Arg
            340                 345                 350

Asn Thr Thr Pro Cys Lys Glu Val Asp Ile Glu Gly Thr Thr Val Ile
    355                 360                 365

Glu Val Gly Leu Asp Pro Ser Asn Asn Met Thr Leu Ala Val Asp Cys
    370                 375                 380

Val Gly Ile Leu Lys Leu Arg Asn Ala Asp Val Glu Ala Arg Ile Gly
385                 390                 395                 400

Ile Ala Gly Ser Lys Lys Lys Ser Thr Arg Ala Arg Leu Val Phe Arg
                405                 410                 415

Val Asn Ile Met Arg Lys Asp Gly Ser Thr Leu Thr Leu Gln Thr Pro
            420                 425                 430

Ser Ser Pro Ile Leu Cys Thr Gln Pro Ala Gly Val Pro Glu Ile Leu
    435                 440                 445

Lys Lys Ser Leu His Ser Cys Ser Val Lys Gly Glu Glu Val Phe
450                 455                 460

Leu Ile Gly Lys Asn Phe Leu Lys Gly Thr Lys Val Ile Phe Gln Glu
465                 470                 475                 480

Asn Val Ser Asp Glu Asn Ser Trp Lys Ser Glu Ala Glu Ile Asp Met
                485                 490                 495

Glu Leu Phe His Gln Asn His Leu Ile Val Lys Val Pro Pro Tyr His
            500                 505                 510

Asp Gln His Ile Thr Leu Pro Val Ser Val Gly Ile Tyr Val Val Thr
    515                 520                 525

Asn Ala Gly Arg Ser His Asp Val Gln Pro Phe Thr Tyr Thr Pro Asp
    530                 535                 540

Pro Ala Ala Ala Gly Ala Leu Asn Val Asn Val Lys Lys Glu Ile Ser
545                 550                 555                 560

Ser Pro Ala Arg Pro Cys Ser Phe Glu Glu Ala Met Lys Ala Met Lys
                565                 570                 575

Thr Thr Gly Cys Asn Leu Asp Lys Val Asn Ile Ile Pro Asn Ala Leu
            580                 585                 590

Met Thr Pro Leu Ile Pro Ser Ser Met Ile Lys Ser Glu Asp Val Thr
    595                 600                 605
```

```
Pro Met Glu Val Thr Ala Glu Lys Arg Ser Ser Thr Ile Phe Lys Thr
    610             615                 620
Thr Lys Ser Val Gly Ser Thr Gln Gln Thr Leu Glu Asn Ile Ser Asn
625             630                 635                 640
Ile Ala Gly Asn Gly Ser Phe Ser Ser Pro Ser Ser His Leu Pro
                645                 650                 655
Ser Glu Asn Glu Lys Gln Gln Gln Ile Gln Pro Lys Ala Tyr Asn Pro
            660                 665                 670
Glu Thr Leu Thr Thr Ile Gln Thr Gln Asp Ile Ser Gln Pro Gly Thr
        675                 680                 685
Phe Pro Ala Val Ser Ala Ser Ser Gln Leu Pro Asn Ser Asp Ala Leu
    690                 695                 700
Leu Gln Gln Ala Thr Gln Phe Gln Thr Arg Glu Thr Gln Ser Arg Glu
705             710                 715                 720
Ile Leu Gln Ser Asp Gly Thr Val Val Asn Leu Ser Gln Leu Thr Glu
                725                 730                 735
Ala Ser Gln Gln Gln Gln Ser Pro Leu Gln Glu Gln Ala Gln Thr
            740                 745                 750
Leu Gln Gln Gln Ile Ser Ser Asn Ile Phe Pro Ser Pro Asn Ser Val
        755                 760                 765
Ser Gln Leu Gln Asn Thr Ile Gln Gln Leu Gln Ala Gly Ser Phe Thr
    770                 775                 780
Gly Ser Thr Ala Ser Gly Ser Ser Gly Ser Val Asp Leu Val Gln Gln
785             790                 795                 800
Val Leu Glu Ala Gln Gln Gln Leu Ser Ser Val Leu Phe Ser Ala Pro
                805                 810                 815
Asp Gly Asn Glu Asn Val Gln Glu Gln Leu Ser Ala Asp Ile Phe Gln
            820                 825                 830
Gln Val Ser Gln Ile Gln Ser Gly Val Ser Pro Gly Met Phe Ser Ser
        835                 840                 845
Thr Glu Pro Thr Val His Thr Arg Pro Asp Asn Leu Leu Pro Gly Arg
    850                 855                 860
Ala Glu Ser Val His Pro Gln Ser Glu Asn Thr Leu Ser Asn Gln Gln
865             870                 875                 880
Gln Gln Gln Gln Gln Gln Gln Val Met Glu Ser Ser Ala Ala Met
                885                 890                 895
Val Met Glu Met Gln Gln Ser Ile Cys Gln Ala Ala Gln Ile Gln
            900                 905                 910
Ser Glu Leu Phe Pro Ser Thr Ala Ser Ala Asn Gly Asn Leu Gln Gln
        915                 920                 925
Ser Pro Val Tyr Gln Gln Thr Ser His Met Met Ser Ala Leu Ser Thr
    930                 935                 940
Asn Glu Asp Met Gln Met Gln Cys Glu Leu Phe Ser Ser Pro Pro Ala
945             950                 955                 960
Val Ser Gly Asn Glu Thr Ser Thr Thr Thr Gln Val Ala Thr
                965                 970                 975
Pro Gly Thr Thr Met Phe Gln Thr Ser Ser Ser Gly Asp Gly Glu Glu
            980                 985                 990
Thr Gly Thr Gln Ala Lys Gln Ile Gln Asn Ser Val Phe Gln Thr Met
        995                 1000                1005
Val Gln Met Gln His Ser Gly Asp Asn Gln Pro Gln Val Asn Leu Phe
    1010                1015                1020
```

```
Ser Ser Thr Lys Ser Met Met Ser Val Gln Asn Ser Gly Thr Gln Gln
1025                1030                1035                1040

Gln Gly Asn Gly Leu Phe Gln Gln Gly Asn Glu Met Met Ser Leu Gln
            1045                1050                1055

Ser Gly Asn Phe Leu Gln Gln Ser Ser His Ser Gln Ala Gln Leu Phe
        1060                1065                1070

His Pro Gln Asn Pro Ile Ala Asp Ala Gln Asn Leu Ser Gln Glu Thr
    1075                1080                1085

Gln Gly Ser Leu Phe His Ser Pro Asn Pro Ile Val His Ser Gln Thr
1090                1095                1100

Ser Thr Thr Ser Ser Glu Gln Met Gln Pro Pro Met Phe His Ser Gln
1105                1110                1115                1120

Ser Thr Ile Ala Val Leu Gln Gly Ser Ser Val Pro Gln Asp Gln Gln
            1125                1130                1135

Ser Thr Asn Ile Phe Leu Ser Gln Ser Pro Met Asn Asn Leu Gln Thr
            1140                1145                1150

Asn Thr Val Ala Gln Glu Ala Phe Phe Ala Ala Pro Asn Ser Ile Ser
        1155                1160                1165

Pro Leu Gln Ser Thr Ser Asn Ser Glu Gln Gln Ala Ala Phe Gln Gln
    1170                1175                1180

Gln Ala Pro Ile Ser His Ile Gln Thr Pro Met Leu Ser Gln Glu Gln
1185                1190                1195                1200

Ala Gln Pro Pro Gln Gln Gly Leu Phe Gln Pro Gln Val Ala Leu Gly
            1205                1210                1215

Ser Leu Pro Pro Asn Pro Met Pro Gln Ser Gln Gln Gly Thr Met Phe
            1220                1225                1230

Gln Ser Gln His Ser Ile Val Ala Met Gln Ser Asn Ser Pro Ser Gln
            1235                1240                1245

Glu Gln Gln Gln Gln Gln Gln Gln Gln Gln Gln Gln Gln Gln Gln Gln
    1250                1255                1260

Gln Gln Ser Ile Leu Phe Ser Asn Gln Asn Thr Met Ala Thr Met Ala
1265                1270                1275                1280

Ser Pro Lys Gln Pro Pro Asn Met Ile Phe Asn Pro Asn Gln Asn
            1285                1290                1295

Pro Met Ala Asn Gln Glu Gln Gln Asn Gln Ser Ile Phe His Gln Gln
            1300                1305                1310

Ser Asn Met Ala Pro Met Asn Gln Glu Gln Gln Pro Met Gln Phe Gln
            1315                1320                1325

Ser Gln Ser Thr Val Ser Ser Leu Gln Asn Pro Gly Pro Thr Gln Ser
    1330                1335                1340

Glu Ser Ser Gln Thr Pro Leu Phe His Ser Ser Pro Gln Ile Gln Leu
1345                1350                1355                1360

Val Gln Gly Ser Pro Ser Ser Gln Glu Gln Gln Val Thr Leu Phe Leu
            1365                1370                1375

Ser Pro Ala Ser Met Ser Ala Leu Gln Thr Ser Ile Asn Gln Gln Asp
        1380                1385                1390

Met Gln Gln Ser Pro Leu Tyr Ser Pro Gln Asn Asn Met Pro Gly Ile
        1395                1400                1405

Gln Gly Ala Thr Ser Ser Pro Gln Pro Gln Ala Thr Leu Phe His Asn
        1410                1415                1420

Thr Ala Gly Gly Thr Met Asn Gln Leu Gln Asn Ser Pro Gly Ser Ser
1425                1430                1435                1440

Gln Gln Thr Ser Gly Met Phe Leu Phe Gly Ile Gln Asn Asn Cys Ser
```

```
                    1445                1450                1455
Gln Leu Leu Thr Ser Gly Pro Ala Thr Leu Pro Asp Gln Leu Met Ala
            1460                1465                1470

Ile Ser Gln Pro Gly Gln Pro Gln Asn Glu Gly Gln Pro Pro Val Thr
        1475                1480                1485

Thr Leu Leu Ser Gln Gln Met Pro Glu Asn Ser Pro Leu Ala Ser Ser
    1490                1495                1500

Ile Asn Thr Asn Gln Asn Ile Glu Lys Ile Asp Leu Leu Val Ser Leu
1505                1510                1515                1520

Gln Asn Gln Gly Asn Asn Leu Thr Gly Ser Phe
            1525                1530

<210> SEQ ID NO 38
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 38
caagcttgac tagtcaatca attacggggt cattagttca t                          41

<210> SEQ ID NO 39
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 39
agctagcaca ccgtacacgc ctaccg                                           26

<210> SEQ ID NO 40
<211> LENGTH: 1548
<212> TYPE: PRT
<213> ORGANISM: Homo sapiens

<400> SEQUENCE: 40

Met Pro Ser Asp Phe Ile Ser Leu Leu Ser Ala Asp Leu Asp Leu Glu
1               5                   10                  15

Ser Pro Lys Ser Leu Tyr Ser Arg Asp Ser Leu Lys Leu His Pro Ser
            20                  25                  30

Gln Asn Phe His Arg Ala Gly Leu Leu Glu Glu Ser Val Tyr Asp Leu
        35                  40                  45

Leu Pro Lys Glu Leu Gln Leu Pro Pro Ser Arg Glu Thr Ser Val Ala
    50                  55                  60

Ser Met Ser Gln Thr Ser Gly Gly Glu Ala Gly Ser Pro Pro Ala
65                  70                  75                  80

Val Val Ala Ala Asp Ala Ser Ser Ala Pro Ser Ser Ser Met Gly
                85                  90                  95

Gly Ala Cys Ser Ser Phe Thr Thr Ser Ser Pro Thr Ile Tyr Ser
            100                 105                 110

Thr Ser Val Thr Asp Ser Lys Ala Met Gln Val Glu Ser Cys Ser Ser
        115                 120                 125

Ala Val Gly Val Ser Asn Arg Gly Val Ser Glu Lys Gln Leu Thr Ser
    130                 135                 140

Asn Thr Val Gln Gln His Pro Ser Thr Pro Lys Arg His Thr Val Leu
145                 150                 155                 160
```

```
Tyr Ile Ser Pro Pro Glu Asp Leu Leu Asp Asn Ser Arg Met Ser
            165                 170                 175

Cys Gln Asp Glu Gly Cys Gly Leu Glu Ser Glu Gln Ser Cys Ser Met
        180                 185                 190

Trp Met Glu Asp Ser Pro Ser Asn Phe Ser Asn Met Ser Thr Ser Ser
        195                 200                 205

Tyr Asn Asp Asn Thr Glu Val Pro Arg Lys Ser Arg Lys Arg Asn Pro
        210                 215                 220

Lys Gln Arg Pro Gly Val Lys Arg Arg Asp Cys Glu Glu Ser Asn Met
225                 230                 235                 240

Asp Ile Phe Asp Ala Asp Ser Ala Lys Ala Pro His Tyr Val Leu Ser
                245                 250                 255

Gln Leu Thr Thr Asp Asn Lys Gly Asn Ser Lys Ala Gly Asn Gly Thr
            260                 265                 270

Leu Glu Asn Gln Lys Gly Thr Gly Val Lys Lys Ser Pro Met Leu Cys
        275                 280                 285

Gly Gln Tyr Pro Val Lys Ser Glu Gly Lys Glu Leu Lys Ile Val Val
        290                 295                 300

Gln Pro Glu Thr Gln His Arg Ala Arg Tyr Leu Thr Glu Gly Ser Arg
305                 310                 315                 320

Gly Ser Val Lys Asp Arg Thr Gln Gln Gly Phe Pro Thr Val Lys Leu
                325                 330                 335

Glu Gly His Asn Glu Pro Val Val Leu Gln Val Phe Val Gly Asn Asp
            340                 345                 350

Ser Gly Arg Val Lys Pro His Gly Phe Tyr Gln Ala Cys Arg Val Thr
        355                 360                 365

Gly Arg Asn Thr Thr Pro Cys Lys Glu Val Asp Ile Glu Gly Thr Thr
        370                 375                 380

Val Ile Glu Val Gly Leu Asp Pro Ser Asn Asn Met Thr Leu Ala Val
385                 390                 395                 400

Asp Cys Val Gly Ile Leu Lys Leu Arg Asn Ala Asp Val Glu Ala Arg
                405                 410                 415

Ile Gly Ile Ala Gly Ser Lys Lys Lys Ser Thr Arg Ala Arg Leu Val
            420                 425                 430

Phe Arg Val Asn Ile Met Arg Lys Asp Gly Ser Thr Leu Thr Leu Gln
        435                 440                 445

Thr Pro Ser Ser Pro Ile Leu Cys Thr Gln Pro Ala Gly Val Pro Glu
        450                 455                 460

Ile Leu Lys Lys Ser Leu His Ser Cys Ser Val Lys Gly Glu Glu Glu
465                 470                 475                 480

Val Phe Leu Ile Gly Lys Asn Phe Leu Lys Gly Thr Lys Val Ile Phe
                485                 490                 495

Gln Glu Asn Val Ser Asp Glu Asn Ser Trp Lys Ser Glu Ala Glu Ile
            500                 505                 510

Asp Met Glu Leu Phe His Gln Asn His Leu Ile Val Lys Val Pro Pro
        515                 520                 525

Tyr His Asp Gln His Ile Thr Leu Pro Val Ser Val Gly Ile Tyr Val
        530                 535                 540

Val Thr Asn Ala Gly Arg Ser His Asp Val Gln Pro Phe Thr Tyr Thr
545                 550                 555                 560

Pro Asp Pro Ala Ala Gly Ala Leu Asn Val Asn Val Lys Lys Glu Ile
                565                 570                 575

Ser Ser Pro Ala Arg Pro Cys Ser Phe Glu Glu Ala Met Lys Ala Met
```

```
                580             585             590
Lys Thr Thr Gly Cys Asn Leu Asp Lys Val Asn Ile Ile Pro Asn Ala
            595             600             605

Leu Met Thr Pro Leu Ile Pro Ser Ser Met Ile Lys Ser Glu Asp Val
        610             615             620

Thr Pro Met Glu Val Thr Ala Glu Lys Arg Ser Ser Thr Ile Phe Lys
625             630             635             640

Thr Thr Lys Ser Val Gly Ser Thr Gln Gln Thr Leu Glu Asn Ile Ser
                645             650             655

Asn Ile Ala Gly Asn Gly Ser Phe Ser Ser Pro Ser Ser His Leu
            660             665             670

Pro Ser Glu Asn Glu Lys Gln Gln Gln Ile Gln Pro Lys Ala Tyr Asn
            675             680             685

Pro Glu Thr Leu Thr Thr Ile Gln Thr Gln Asp Ile Ser Gln Pro Gly
        690             695             700

Thr Phe Pro Ala Val Ser Ala Ser Ser Gln Leu Pro Asn Ser Asp Ala
705             710             715             720

Leu Leu Gln Gln Ala Thr Gln Phe Gln Thr Arg Glu Thr Gln Ser Arg
                725             730             735

Glu Ile Leu Gln Ser Asp Gly Thr Val Val Asn Leu Ser Gln Leu Thr
            740             745             750

Glu Ala Ser Gln Gln Gln Gln Ser Pro Leu Gln Glu Gln Ala Gln
            755             760             765

Thr Leu Gln Gln Gln Ile Ser Ser Asn Ile Phe Pro Ser Pro Asn Ser
        770             775             780

Val Ser Gln Leu Gln Asn Thr Ile Gln Gln Leu Gln Ala Gly Ser Phe
785             790             795             800

Thr Gly Ser Thr Ala Ser Gly Ser Ser Gly Ser Val Asp Leu Val Gln
                805             810             815

Gln Val Leu Glu Ala Gln Gln Gln Leu Ser Ser Val Leu Phe Ser Ala
            820             825             830

Pro Asp Gly Asn Glu Asn Val Gln Glu Gln Leu Ser Ala Asp Ile Phe
            835             840             845

Gln Gln Val Ser Gln Ile Gln Ser Gly Val Ser Pro Gly Met Phe Ser
        850             855             860

Ser Thr Glu Pro Thr Val His Thr Arg Pro Asp Asn Leu Leu Pro Gly
865             870             875             880

Arg Ala Glu Ser Val His Pro Gln Ser Glu Asn Thr Leu Ser Asn Gln
                885             890             895

Gln Gln Gln Gln Gln Gln Gln Gln Val Met Glu Ser Ser Ala Ala
            900             905             910

Met Val Met Glu Met Gln Gln Ser Ile Cys Gln Ala Ala Gln Ile
            915             920             925

Gln Ser Glu Leu Phe Pro Ser Thr Ala Ser Ala Asn Gly Asn Leu Gln
        930             935             940

Gln Ser Pro Val Tyr Gln Gln Thr Ser His Met Met Ser Ala Leu Ser
945             950             955             960

Thr Asn Glu Asp Met Gln Met Gln Cys Glu Leu Phe Ser Ser Pro Pro
                965             970             975

Ala Val Ser Gly Asn Glu Thr Ser Thr Thr Thr Gln Gln Val Ala
            980             985             990

Thr Pro Gly Thr Thr Met Phe Gln Thr Ser Ser Ser Gly Asp Gly Glu
        995             1000            1005
```

```
Glu Thr Gly Thr Gln Ala Lys Gln Ile Gln Asn Ser Val Phe Gln Thr
1010                1015                1020

Met Val Gln Met Gln His Ser Gly Asp Asn Gln Pro Gln Val Asn Leu
1025                1030                1035                1040

Phe Ser Ser Thr Lys Ser Met Met Ser Val Gln Asn Ser Gly Thr Gln
                1045                1050                1055

Gln Gln Gly Asn Gly Leu Phe Gln Gln Gly Asn Glu Met Met Ser Leu
        1060                1065                1070

Gln Ser Gly Asn Phe Leu Gln Gln Ser Ser His Ser Gln Ala Gln Leu
            1075                1080                1085

Phe His Pro Gln Asn Pro Ile Ala Asp Ala Gln Asn Leu Ser Gln Glu
        1090                1095                1100

Thr Gln Gly Ser Leu Phe His Ser Pro Asn Pro Ile Val His Ser Gln
1105                1110                1115                1120

Thr Ser Thr Thr Ser Ser Glu Gln Met Gln Pro Pro Met Phe His Ser
                1125                1130                1135

Gln Ser Thr Ile Ala Val Leu Gln Gly Ser Ser Val Pro Gln Asp Gln
            1140                1145                1150

Gln Ser Thr Asn Ile Phe Leu Ser Gln Ser Pro Met Asn Asn Leu Gln
        1155                1160                1165

Thr Asn Thr Val Ala Gln Glu Ala Phe Phe Ala Ala Pro Asn Ser Ile
1170                1175                1180

Ser Pro Leu Gln Ser Thr Ser Asn Ser Glu Gln Gln Ala Ala Phe Gln
1185                1190                1195                1200

Gln Gln Ala Pro Ile Ser His Ile Gln Thr Pro Met Leu Ser Gln Glu
            1205                1210                1215

Gln Ala Gln Pro Pro Gln Gln Gly Leu Phe Gln Pro Gln Val Ala Leu
            1220                1225                1230

Gly Ser Leu Pro Pro Asn Pro Met Pro Gln Ser Gln Gln Gly Thr Met
        1235                1240                1245

Phe Gln Ser Gln His Ser Ile Val Ala Met Gln Ser Asn Ser Pro Ser
    1250                1255                1260

Gln Glu Gln Gln Gln Gln Gln Gln Gln Gln Gln Gln Gln Gln Gln Gln
1265                1270                1275                1280

Gln Gln Gln Ser Ile Leu Phe Ser Asn Gln Asn Thr Met Ala Thr Met
            1285                1290                1295

Ala Ser Pro Lys Gln Pro Pro Asn Met Ile Phe Asn Pro Asn Gln Asn
                1300                1305                1310

Asn Pro Met Ala Asn Gln Glu Gln Gln Asn Gln Ser Ile Phe His Gln
            1315                1320                1325

Gln Ser Asn Met Ala Pro Met Asn Gln Glu Gln Gln Pro Met Gln Phe
    1330                1335                1340

Gln Ser Gln Ser Thr Val Ser Ser Leu Gln Asn Pro Gly Pro Thr Gln
1345                1350                1355                1360

Ser Glu Ser Ser Gln Thr Pro Leu Phe His Ser Ser Pro Gln Ile Gln
                1365                1370                1375

Leu Val Gln Gly Ser Pro Ser Ser Gln Glu Gln Gln Val Thr Leu Phe
            1380                1385                1390

Leu Ser Pro Ala Ser Met Ser Ala Leu Gln Thr Ser Ile Asn Gln Gln
        1395                1400                1405

Asp Met Gln Gln Ser Pro Leu Tyr Ser Pro Gln Asn Asn Met Pro Gly
    1410                1415                1420
```

```
Ile Gln Gly Ala Thr Ser Ser Pro Gln Pro Gln Ala Thr Leu Phe His
1425                1430                1435                1440

Asn Thr Ala Gly Gly Thr Met Asn Gln Leu Gln Asn Ser Pro Gly Ser
                1445                1450                1455

Ser Gln Gln Thr Ser Gly Met Phe Leu Phe Gly Ile Gln Asn Asn Cys
            1460                1465                1470

Ser Gln Leu Leu Thr Ser Gly Pro Ala Thr Leu Pro Asp Gln Leu Met
        1475                1480                1485

Ala Ile Ser Gln Pro Gly Gln Pro Gln Asn Glu Gly Gln Pro Pro Val
    1490                1495                1500

Thr Thr Leu Leu Ser Gln Gln Met Pro Glu Asn Ser Pro Leu Ala Ser
1505                1510                1515                1520

Ser Ile Asn Thr Asn Gln Asn Ile Glu Lys Ile Asp Leu Leu Val Ser
                1525                1530                1535

Leu Gln Asn Gln Gly Asn Asn Leu Thr Gly Ser Phe
            1540                1545

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Arg Ala His Tyr Glu Thr Glu Gly
 1               5
```

COMPOSITIONS AND METHODS FOR REGULATING CELL OSMOLARITY

CROSS-REFERENCE TO RELATED APPLICATIONS

This application is a continuation of U.S. patent application Ser. No. 13/063,912, filed Jun. 17, 2011, which is a U.S. national phase application of International Application No. PCT/US2009/057031 under 35 U.S.C. 371, filed Sep. 15, 2009, which claims benefit of U.S. Provisional Patent Application No. 61/097,149, filed Sep. 15, 2008, the contents of which are herein incorporated by reference in their entireties.

SEQUENCE LISTING

This application contains a Sequence Listing submitted via EFS-Web and hereby incorporated by reference in its entirety. Said ASCII copy, created on Feb. 12, 2018, is named 146392005701SEQLIST.txt, and is 31,806 bytes in size.

TECHNICAL FIELD

This invention relates generally to molecular and cell biology, cell culture systems and bioreactors, and to the recombinant production of products such as polypeptides in cell culture. In particular, this invention provides compositions and methods for regulating intracellular osmolarity in cells, e.g., in cultured cells, including in cultured cells in bioreactors.

BACKGROUND OF THE RELATED ART

Bioreactors culturing mammalian cells are used to make recombinant protein drugs such as growth factors, thrombolytic agents, interferons, interleukins, erythropoietins, colony stimulating factors and various other cytokines, and antibodies. However, in bioreactors, the osmolality of the culture increases as a result of base addition to control pH as well as feedings of nutrients and supplements to supply necessary energy for the culture. Typically, throughout a fed-batch bioreactor run, osmolality increases from about 300 milliosmoles/kg (mOsm) to values sometimes as high as 600 mOsm. It has been shown that compared to 300 mOsm cell cultures, within a range of osmolality (above 340 mOsm and below a threshold comprised between 400 and 450 mOsm) specific productivity of mammalian cells increases while cells' growth rate decreases and cells' death rate is not impacted. For most cell lines there seems to exist an osmolality threshold above which cell death rate increases dramatically with osmolality (often times that thresholds seems to be comprised between 400 and 450 mOsm).

In bioreactors, increased osmolality is correlated with increased tonicity (increased NaCl). High NaCl activates the transcription factor tonicity-responsive enhancer-/osmotic response element-binding protein (TonEBP/OREBP, where TonE is also called "tonicity enhancer," or "osmotic response element"), which activates TonE, resulting in increased transcription of several protective genes whose promoters are controlled by its cognate binding sites: the enhancer ORE/TonE.

Regulation of TonEBP/OREBP transcriptional activity is complex. Within 30 min of hypertonicity, TonEBP/OREBP becomes phosphorylated and translocates into the nucleus. Hours later, TonEBP/OREBP mRNA and protein abundance increase. Also, hypertonicity increases transactivating activity of TonEBP/OREBP, associated with phosphorylation of its transactivating domain. More slowly, hypertonicity increases TonEBP/OREBP abundance through induction of its mRNA and protein synthesis.

SUMMARY OF THE INVENTION

The invention provides isolated, synthetic or recombinant nucleic acid molecules comprising: (a) at least one osmo-responsive transcriptional regulatory element (ORTRE) comprising at least one TonEBP-responsive or NFATc-responsive transcriptional enhancer operatively linked to a transcriptional regulatory sequence; (b) the nucleic acid molecule of (a), wherein the transcriptional regulatory sequence is transcriptionally active in a eukaryotic cell, or the transcriptional regulatory sequence is derived from a eukaryotic cell; (c) the nucleic acid molecule of (a) or (b), wherein the transcriptional regulatory sequence is transcriptionally active in a vertebrate, a mammalian, a human, an insect, a plant, a yeast or a fungal cell, or a virus, or the transcriptional regulatory sequence is derived from a vertebrate, a mammalian, a human, an insect, a plant, a yeast or a fungal cell, or a virus, or the transcriptional regulatory sequence is a synthetic sequence; or, (d) the nucleic acid molecule of (a), wherein the transcriptional regulatory sequence comprises a promoter and/or an enhancer.

In alternative embodiments, the at least one TonEBP-responsive or NFATc responsive transcriptional enhancer molecule (sequence) is positioned 5' to the promoter in a sense or antisense orientation; or, the at least one TonEBP-responsive or NFATc responsive transcriptional enhancer sequence is positioned 3' to the promoter in a sense or antisense orientation; or, the at least one TonEBP-responsive or NFATc-responsive transcriptional enhancer sequence is positioned 5' to the promoter in a sense or antisense orientation, and a second, third and/or additional TonEBP-responsive or NFATc responsive transcriptional enhancer sequence is positioned 3' to the promoter in a sense or antisense orientation.

In alternative embodiments, the OR-TRE further comprises at least one Activator Protein-1 (AP-1)-responsive transcriptional enhancer operatively linked to the TonEBP responsive or NFATc-responsive transcriptional enhancer sequence. The Activator Protein-1 (AP-1)-responsive transcriptional enhancer can be positioned 5' to the OR-TRE in a sense or antisense orientation; or, the Activator Protein-1 (AP-1)-responsive transcriptional enhancer can be positioned 3' to the OR-TRE in a sense or antisense orientation; or, an Activator Protein-1 (AP-1)-responsive transcriptional enhancer can be positioned 5' to the OR-TRE in a sense or antisense orientation, and a second, third and/or additional Activator Protein-1 (AP-1)-responsive transcriptional enhancer is positioned 3' to the OR-TRE in a sense or antisense orientation.

In alternative aspects, the Activator Protein-1 (AP-1)-responsive transcriptional enhancer is positioned 5' to the promoter, in a sense or antisense orientation; or, the Activator Protein-1 (AP-1)-responsive transcriptional enhancer is positioned 3' to the promoter, in a sense or antisense orientation; or, an Activator Protein-1 (AP-1) responsive transcriptional enhancer is positioned 5' to the promoter in a sense or antisense orientation, and a second Activator Protein-1 (AP-1)-responsive transcriptional enhancer is positioned 3' to the promoter in a sense or antisense orientation.

In one embodiment, at least one TonEBP-responsive or NFATc-responsive transcriptional enhancer and/or at least one Activator Protein-1 (AP-1)-responsive transcriptional enhancer has (comprises), or further comprises, a eukaryotic (e.g., a vertebrate, a mammalian, a human, an insect, a yeast or fungal), a prokaryotic, a plant, viral and/or a synthetic nucleic acid molecule sequence.

In alternative embodiments, the at least one TonEBP-responsive transcriptional enhancer comprises the nucleic acid sequence of 5'-T/A/C)GGAA(A/T)NN(T/A/C)N(T/A/C)-3' (SEQ ID NO:1), wherein N can be any nucleic acid residue; and/or the at least one NFATc-responsive transcriptional enhancer comprises the nucleic acid sequence of 5'-(T/A/C)GGAA(C/G)(A/G)-3' (SEQ ID NO:2), or 5'-(T/A/C)GGAAANN(T/A/C)N(T/A/C)-3' (SEQ ID NO:4), wherein N can be any nucleic acid residue; and/or the at least one Activator Protein-1 (AP-1)-responsive transcriptional enhancer comprises the nucleic acid sequence of 5'-TGA(C/G)TCA-3' (SEQ ID NO:3).

In alternative embodiments, the at least one TonEBP-responsive transcriptional enhancer comprises the nucleotide sequence of 5'-(T/A/C)GGAAANN(T/A/C)N(T/A/C)-3' (SEQ ID NO:4); and/or the at least one NFATc-responsive transcriptional enhancer comprises the nucleic acid sequence of 5'-TGGAAATTTGT-3' (SEQ ID NO:5); and/or the at least one Activator Protein-1 (AP-1)-responsive transcriptional enhancer comprises the nucleotide sequence of 5'-TGACTCA-3' (SEQ ID NO:6).

In one embodiment, the OR-TRE comprises the nucleotide sequence of 5'-TTGGAAAATCACCA-GAATGGGATTTAGAGAGGTGGGGTTCCTGACT-CATT-3' (SEQ ID NO:7), or, residues 2 to 12 of (SEQ ID NO:7) (which corresponds to 5'-TGGAAAATCAC-3') (SEQ ID NO:9), or 5'-TTGACTAGTTGGAAAATCACCA-GAATGGGATTTAGAGAGGTGGGGTTC CTGACTCAT-TGCTAGCTCGAGCTCGGTACCCGGGTCGAGTAG-GCGTGTACGGTGG GAG-3' (SEQ ID NO:8) where TonE and AP1 binding sites in (SEQ ID NO:7) and (SEQ ID NO:8) are in bold.

In one embodiment, a TonEBP-responsive transcriptional enhancer element (sequence) used in an osmo-responsive construct of the invention comprises a nucleic acid that specifically binds to a protein comprising the amino acid residue motif RAHYETEG (SEQ ID NO:41).

In one embodiment, the at least one TonEBP-responsive transcriptional enhancer is positioned 5' to at least one Activator Protein-1 (AP-1)-responsive transcriptional enhancer, or, at least one Activator Protein-1 (AP-1)-responsive transcriptional enhancer sequence is positioned 5' to at least one TonEBP-responsive transcriptional enhancer.

In alternative embodiments, at least one TonEBP-responsive transcriptional enhancer sequence is positioned within 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 75, 100, 125, 150, 200, 250, 300, 350, 400 or 500 or more nucleotide residues of at least one Activator Protein-1 (AP-1)-responsive transcriptional enhancer.

In alternative embodiments, at least one TonEBP-responsive transcriptional enhancer is positioned within 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 75, 100, 125, 150, 200, 250, 300, 350, 400 or 500 or more nucleotide residues of the promoter.

In alternative embodiments, at least one Activator Protein-1 (AP-1)-responsive transcriptional enhancer sequence is positioned within 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 75, 100, 125, 150, 200, 250, 300, 350, 400 or 500 or more nucleotides of the promoter.

In alternative embodiments, the promoter is a constitutive promoter, an inducible promoter, a synthetic promoter, a mammalian promoter, a bacterial promoter, a plant promoter, a yeast promoter, a fungal promoter, a viral promoter, or a cytomegalovirus (CMV) promoter.

In alternative embodiments, the OR-TRE comprises one to ten (1 to 10) or more TonEBP-responsive transcriptional enhancers, and/or the OR-TRE comprises 1, 2, 3, 4, 5, 6, 7, 8, 9 or 10 or more Activator Protein-1 (AP-1)-responsive transcriptional enhancers.

In alternative embodiments, the nucleic acid molecule further comprises one or more additional nucleic acid molecules (sequences) operatively linked to the promoter transcriptionally active in a cell, e.g., a eukaryotic cell. The additional nucleic acid molecule or molecules (sequences) can comprise one or more protein-coding nucleic acid molecules, or one or more regulatory nucleic acids (a nucleic acid having an inhibitory, stabilizing or upregulating function or effect). For example, a regulatory nucleic acid can be one or more sense or antisense nucleic acid molecules (sequences). In alternative embodiments, the additional nucleic acid molecule comprises: (a) a protein-coding nucleic acid molecule; (b) a regulatory nucleic acid molecule; or (c) the nucleic acid molecule of (b), wherein the regulatory nucleic acid molecule is an inhibitory, stabilizing or up-regulating nucleic acid molecule, or a sense or an antisense sequence.

In alternative embodiments, the additional nucleic acid molecule comprises a nucleic acid molecule (sequence) encoding an osmo-protective protein or peptide; or, the additional nucleic acid molecule comprises a nucleic acid molecule (sequence) encoding: an anti-apoptotic protein; a protein that confers resistance to oxidative stress to a cell; a chaperone protein involved in facilitating protein folding; a protein involved in extracellular secretion of proteins; a glycolytic enzyme; a cell cycle regulation protein; a glycosylation enzyme, or any combination thereof.

In alternative embodiments, the regulatory nucleic acid, e.g., inhibitory, nucleic acid molecule comprises a sense sequence, an antisense sequence, a ribozyme, a short interfering RNA (siRNA), or a microRNA (miRNA). The additional nucleic acid molecule can comprise a nucleic acid molecule encoding a NFATc or a TonEBP polypeptide.

The invention provides isolated, synthetic or recombinant osmo-responsive nucleic acid molecules comprising: (a) at least one OR-TRE of the invention operatively linked to a nucleic acid, wherein the OR-TRE regulates or drives the transcription of the nucleic acid; (b) the nucleic acid molecule of (a), wherein the transcribed nucleic acid encodes (comprises) a polypeptide-encoding nucleic acid molecule; (c) the nucleic acid molecule of (b), wherein the transcribed nucleic acid encodes: (i) an osmo-protective protein or peptide, or a protein that protects a cell in an environment of increasing osmolality, or protects a cell under conditions of hyperosmolality or increasing hyperosmolality; (ii) an anti-apoptotic protein; (iii) a protein that confers resistance to oxidative stress to a cell; (iv) a chaperone protein involved in facilitating protein folding; (v) a protein involved in extracellular secretion of proteins; (vi) a glycolytic enzyme; (vii) a cell cycle regulation protein; (viii) a glycosylation enzyme; or (ix) any combination of (i) to (viii); (d) the nucleic acid molecule of (a), wherein the transcribed nucleic acid comprises a regulatory nucleic acid, e.g., an inhibitory, stabilizing or a up-regulating nucleic acid molecule, or a nucleic acid molecule comprising sense or an antisense sequence; (e) the nucleic acid molecule of (d), wherein the regulatory nucleic acid, e.g., an inhibitory, stabilizing or a up-regulating nucleic acid molecule, comprises a sense, an antisense sequence, a ribozyme, a short interfering RNA (siRNA), or a microRNA (miRNA); (f) the polypeptide-encoding nucleic acid molecule of (b), wherein the transcribed nucleic acid encodes a NFATc polypeptide, an AP-1 polypeptide, a TonEBP polypeptide, a calcineurin polypeptide, or a combination thereof.

In alternative embodiments, the osmo-protective osmo-protective protein or peptide is a proline or a glycine-betaine, a taurine transporter, a glycine betaine-γ-aminobutyric acid transporter, a sodium-myo-inositol cotransporter, a heat shock protein, an aquaporin, or an aldose reductase. The anti-apoptotic protein can be a Bcl-2, Bcl-xL, Mcl-1, BHRF1, X-IAP, IAP1, IAP2 IEX-1L, Bfl-1 or Bcl-w. The protein that confers resistance to oxidative stress to a cell can be a superoxide dismutase, a catalase, a glutathione peroxidase, a peroxiredoxin, a sulfiredoxin, thioredoxin, thioredoxin reductase, thioredoxin peroxidase, thioltransferase, glutaredoxin or a glutathione reductase.

In alternative embodiments, the chaperone protein involved in facilitating protein folding is a binding immunoglobulin protein (BiP), calnexin, calreticulin, ERp57 or a protein disulfide isomerase (PDI).

The glycolytic enzyme can be a pyruvate carboxylase or a pyruvate kinase. The cell cycle regulation protein can be a cyclin or a cyclin-dependent kinase, or an inhibitor of a cyclin or a cyclin-dependent kinase.

The invention provides isolated, synthetic or recombinant nucleic acid molecules comprising at least one osmo-responsive transcriptional regulatory element operatively linked to at least one nucleic acid molecule comprising a targeting nucleic acid molecule. The targeting nucleic acid molecule can comprise a nucleic acid molecule for targeting a lactogenic gene or a lactogenic message or a lactogenic protein to decrease expression of a lactogenic gene or a lactogenic message or a lactogenic protein. The lactogenic gene can be a lactate dehydrogenase. The nucleic acid comprising a nucleic acid molecule targeting a lactogenic gene or lactogenic gene message can comprise a short interfering RNA (siRNA), a microRNA (miRNA), an antisense RNA and/or an RNA with ribozyme activity. In one embodiment, the at least one osmo-responsive transcriptional regulatory element comprises an osmo-responsive transcriptional regulatory element (OR-TRE) of the invention.

In one aspect, the osmo-responsive nucleic acid molecule further comprises a nucleic acid molecule coding for a transcript (message) comprising a 5' untranslated region, a 3' untranslated region or both a 5' untranslated region and a 3' untranslated region. In one aspect, the osmo-responsive nucleic acid molecule further comprises at least one transcriptional or translational regulatory sequence which, in one embodiment, can be positioned within the 5' untranslated region, or positioned within the 3' untranslated region, or both.

The invention provides vectors comprising (a) the nucleic acid molecule of the invention, (b) the nucleic acid of the invention; and/or (c) the osmo-responsive nucleic acid of the invention. In alternative embodiments, the vector is an expression cassette, a recombinant virus, a plasmid, a phage, a phagemid, an artificial chromosome or a cloning vehicle; or, the vector is a bacteriophage P1-derived vector, a bacterial artificial chromosome, a yeast artificial chromosome, or a mammalian artificial chromosome; or the vector is an extra-chromosomal episome. In one aspect, the vector is an integrating vector.

The invention provides cells comprising: (a) the nucleic acid of the invention, (b) the nucleic acid of the invention; and/or (c) the osmo-responsive nucleic acid of the invention; or (b) a vector of the invention. In alternative embodiments, the cell is a mammalian cell, a human cell, a mouse cell, an insect cell, a fungal cell, a bacterial cell, a plant cell, an immortal cell or a Chinese hamster ovary (CHO) cell. The vector in the cell can be an extra-chromosomal episome, or, the vector can be stably integrated into the cell's genome. A nucleic acid of this invention can be an episomal, transient expression construct, or a genomically integrated expression construct, which alternatively can be a stable genomic insert.

The invention provides bioreactors, culture dishes, petri dishes, test tubes, roller bottles and the like, comprising a cell of the invention.

The invention provides methods for protecting a cell in an environment of increasing osmolality, or under conditions of hyperosmolality or increasing hyperosmolality, or maintaining osmolality or osmolarity in a cell, comprising expressing an osmo-protective protein or peptide or an osmo-protective regulatory nucleic acid molecule, wherein the method comprises: (a) introducing a polynucleotide into the cell, wherein said polynucleotide comprises: a nucleic acid molecule of the invention and/or an osmo-responsive nucleic acid molecule of the invention, or the vector of the invention; wherein the polynucleotide encodes an osmo-protective protein or peptide, or is itself an osmo-protective nucleic acid molecule; and (b) culturing the cell such that the osmo-protective protein or peptide, or the osmo-protective regulatory nucleic acid, is expressed, thereby protecting the cell in an environment of increasing osmolality, or under conditions of hyperosmolality or increasing hyperosmolality.

In alternative aspects of these methods, the osmo-protective protein or peptide comprises: (i) a protein that protects a cell in an environment of increasing osmolality (e.g., protects a cell under conditions of hyperosmolality or increasing hyperosmolality); (ii) an anti-apoptotic protein; (iii) a protein that confers resistance to oxidative stress to a cell; (iv) a chaperone protein involved in facilitating protein folding; (v) a protein involved in extracellular secretion of proteins; (vi) a glycolytic enzyme; (vii) a cell cycle regulation protein; (viii) a glycosylation enzyme; or (ix) any combination of (i) to (viii).

The invention provides methods for increasing production or regulating production of a recombinant protein in a cell (including cultured cells, e.g., as cells in a bioreactor), or increasing the production of correctly folded proteins or correctly glycosylated proteins under conditions of hyperosmolality in a cell (including cultured cells, e.g., as cells in a bioreactor), comprising: (a) providing a heterologous or recombinant nucleic acid molecule encoding the recombinant protein; and (b) stably or transiently inserting into the cell a polynucleotide comprising: a nucleic acid of the invention and/or the osmo-responsive nucleic acid of the invention, wherein the nucleic acid molecule encodes an osmo-protective protein or peptide, or an osmo-protective regulatory nucleic acid; and (c) culturing the cell under conditions wherein the osmo-protective protein or peptide or osmo-protective regulatory nucleic acid of (b) and the recombinant protein of (a) are expressed, thereby increasing production or regulating production of the recombinant protein in the cell, or increasing the production or regulating production of correctly folded proteins or correctly glycosylated proteins under conditions of hyperosmolality in the cell.

The invention provides methods for increasing production or regulating production of a recombinant protein, or increasing the production or regulating production of correctly folded proteins or correctly glycosylated proteins under conditions of hyperosmolality in a cell, in a bioreactor, an implant or an artificial organ, comprising: (a) providing a bioreactor, an implant or an artificial organ comprising a cell of the invention, wherein the cell comprises a nucleic acid of the invention and/or the osmo responsive nucleic acid molecule of the invention, or the vector of the invention; and the nucleic acid molecule or vector encodes an osmo-protective protein or peptide; and (b) culturing the cell under conditions wherein the osmo-protective protein or peptide or the osmo-protective regulatory nucleic acid, and the recombinant protein are expressed, or placing the bioreactor, implant or artificial organ in conditions permissive for expression of the osmo-protective protein or peptide or the osmo-protective regulatory nucleic acid, and the recombinant protein by the cell.

The invention provides methods for adding or enhancing a cell's adaptability or resistance to osmotic stress or osmotic shock comprising introducing to a cell a polynucleotide comprising: a nucleic acid of the invention and/or the osmo-responsive nucleic acid molecule of the invention, or the vector of the invention; wherein the nucleic acid molecule or vector encodes an osmo-protective protein or peptide or an osmoprotective regulatory nucleic acid. In alternative aspects, as used herein osmotic stress is different from osmotic shock in that osmotic stress encompasses a gradual change in osmolality (stress) of a culture system, a cell, etc., versus osmotic shock, which encompasses acute change (shock) osmolality (stress) of a culture system, a cell, etc.

In alternative aspects of these methods, the method adds or enhances the cell's adaptability or resistance to hypertonic osmotic stress or hypertonic osmotic shock, or, the method adds or enhances the cell's adaptability or resistance to hypotonic osmotic stress or hypotonic osmotic shock.

The invention provides methods for increasing production or regulating production of a recombinant protein in a cell, or increasing the production of correctly folded proteins or correctly glycosylated proteins under conditions of hyperosmolality in a cell, comprising: (a) providing a heterologous or recombinant nucleic acid molecule encoding the recombinant protein; and (b) stably or transiently inserting into a cell a polynucleotide comprising: a nucleic acid of the invention and/or the osmo-responsive nucleic acid molecule of the invention, or the vector of the invention; wherein the nucleic acid molecule or vector encodes an osmo-protective protein or peptide; and (c) culturing the cell under conditions wherein the osmo-protective protein or peptide or nucleic acid of (b), and the recombinant protein of (a), are expressed.

The invention provides methods for increasing production or regulating production of a recombinant protein in an implant or an artificial organ, or increasing the production of correctly folded proteins or correctly glycosylated proteins under conditions of hyperosmolality in an implant or an artificial organ, comprising: (a) providing a cell comprising a heterologous or recombinant nucleic acid molecule encoding the recombinant protein; and (b) stably or transiently inserting into the cell a polynucleotide comprising: a nucleic acid of the invention and/or the osmo-responsive nucleic acid molecule of the invention, or the vector of the invention, wherein the nucleic acid molecule encodes an osmo-protective protein or peptide or an osmo-protective nucleic acid molecule; and (c) inserting the cell in the implant or artificial organ and maintaining the implant or artificial organ in conditions allowing expression of the osmo-protective protein or peptide or the osmo-protective nucleic acid molecule, and the recombinant protein in the cell, thereby increasing production or regulating production of the recombinant protein in the implant or the artificial organ.

The invention provides methods for the efficient production of biomolecules in dense or late-stage cell production systems, or allowing higher yields of total biomolecules or higher yields of post-translationally processed proteins in dense or late stage cell production systems, comprising: (a) stably or transiently inserting into a cell capable of generating the biomolecule a polynucleotide comprising: a nucleic acid of the invention and/or the osmo-responsive nucleic acid molecule of the invention, or the vector of the invention, wherein the nucleic acid molecule encodes an osmo-protective protein or peptide or an osmo-protective nucleic acid molecule; (b) the method of (a), wherein the biomolecule is a small molecule, a polypeptide and/or nucleic acid; or (c) the method of (a) or (b), wherein the method results in higher yields of properly folded or preferably folded (e.g., a wild type folding, wild type-pattern folding) or glycosylated polypeptides.

The invention provides artificial organs or implants comprising a cell of the invention, a vector of the invention, and/or an osmo-responsive nucleic acid molecule of the invention. The invention provides methods products of manufacture comprising a cell of the invention, a vector of the invention, and/or an osmo-responsive nucleic acid molecule of the invention. The invention provides kits comprising a cell of the invention, a nucleic acid molecule of the invention, a vector of the invention, and/or an osmoresponsive nucleic acid molecule of the invention. In one aspect, the kit further comprises instructions for practicing a method of the invention.

Thus, in certain embodiments, the invention provides an isolated nucleic acid molecule comprising at least one osmo-responsive transcriptional regulatory element (OR-TRE) comprising at least one TonEBP-responsive transcriptional enhancer or NFATc-responsive transcriptional enhancer operatively linked to a transcriptional regulator and at least one Activator Protein (AP-1)-responsive transcriptional enhancer operatively linked to said TonEBP-responsive transcriptional enhancer or NFATc-responsive transcriptional enhancer. The transcriptional regulator may be, for example, a promoter, an enhancer or a combination thereof. In some embodiments a first TonEBP-responsive transcriptional enhancer or NFATc-responsive transcriptional enhancer positioned 5' to a promoter, and a second TonEBP-responsive transcriptional enhancer or NFAT-responsive transcriptional enhancer positioned 3' to the promoter. In some embodiments, a first Activator Protein-1 (AP-1)-responsive transcriptional enhancer is positioned 5' of the OR-TRE and a second Activator Protein-1 (AP-1)-responsive transcriptional enhancer positioned 3' of the OR-TRE. In some embodiments, the Activator Protein-1 (AP-1)-responsive transcriptional enhancer is positioned 5' of the transcriptional regulator and the transcriptional regulator is a promoter. In other embodiments, the Activator Protein-1 (AP-1)-responsive transcriptional enhancer is positioned 3' of the transcriptional regulator which is a promoter. In still other embodiments, a first Activator Protein-1 (AP-1)-responsive transcriptional enhancer is positioned 5' to the transcriptional regulator and a second Activator Protein-1 (AP-1) responsive transcriptional enhancer is positioned 3' to the transcriptional regulator, wherein the first transcriptional regulator and the second transcriptional regulator are both promoters. In some embodiments, the nucleic acid molecule contains (a) at least one TonEBP-responsive transcriptional enhancer comprising the nucleic acid sequence of SEQ ID NO:1; or (b) at least one NFATc-responsive transcriptional enhancer comprising the nucleic acid sequence of SEQ ID NO:2 or SEQ ID NO:4; or (c) at least one Activator Protein-1 (AP-1)-responsive transcriptional enhancer comprising the nucleic acid sequence of SEQ ID NO:3 (wherein N can be any nucleotide).

In certain embodiments, the OR-TRE of the invention comprises the nucleotide sequence of SEQ ID NO:7, SEQ ID NO:8, or SEQ ID NO:9.

The nucleic acid molecule of the invention may further comprise an additional nucleic acid molecule operatively linked to the transcriptional regulator, wherein the transcriptional regulator is a promoter that is transcriptionally active in a eukaryotic cell. The additional nucleic acid molecule may be a protein-encoding nucleic acid molecule (e.g., encoding a protein of interest) or regulatory nucleic molecule (e.g., an inhibitory molecule, a stabilizing molecule, an up-regulating nucleic acid molecule, or one that produces an antisense molecule). In some embodiments, the inhibitory nucleic acid molecule comprises an antisense sequence, a ribozyme, a short interfering RNA (siRNA), or a microRNA (miRNA).

In some embodiments, the additional nucleic acid molecule encodes an osmo-protective protein or peptide such as, for example, a proline or a glycine-betaine, a taurine transporter, a glycine betaine-γ-aminobutyric acid transporter, a sodium-myo-inositol cotransporter, a heat shock protein, an aquaporin, an aldose reductase, or a neuropathy target esterase (NTE). In other embodiments, the additional nucleic acid molecule encodes a protein or peptide that confers a beneficial property to proteins expressed in cells. A protein that confers a benefit may be, for example, an anti-apoptotic protein (e.g., Bcl-2, Bcl-xL, Mcl-1, BHRF1, X-IAP, IAP1, IAP2 IEX-1L, Bfl-1 or Bcl-w); a protein that confers resistance to oxidative stress to a cell (e.g., superoxide dismutase, a catalase, a glutathione peroxidase, a peroxiredoxin, a sulfiredoxin, thioredoxin, thioredoxin reductase, thioredoxin peroxidase, thioltransferase, glutaredoxin or a glutathione reductase); a chaperone protein involved in facilitating protein folding (e.g., binding immunoglobulin protein (BiP), calnexin, calreticulin, ERp57 or a protein disulfide isomerase (PDI)); a protein involved in extracellular secretion of proteins; a glycolytic enzyme (e.g., pyruvate carboxylase or a pyruvate kinase); a cell cycle regulation protein (e.g., cyclin or a cyclin-dependent kinase, or an inhibitor of a cyclin or a cyclin-dependent kinase); a glycosylation enzyme, or any combination thereof. In other embodiments, the additional nucleic acid molecule encodes an NFATc or a TonEBP polypeptide.

In some embodiments, the OR-TRE is operatively linked to at least one targeting nucleic acid molecule, such as, for example, a nucleic acid molecule for targeting a lactogenic gene, a lactogenic message, or a lactogenic protein to decrease expression of said lactogenic gene (e.g., lactate dehydrogenase), lactogenic message, or a lactogenic protein. In some embodiments, these nucleic acid molecules targeting a lactogenic gene or lactogenic message comprises a short interfering RNA (siRNA), a microRNA (miRNA), an antisense RNA and/or an RNA with ribozyme activity.

The invention includes vectors comprising the nucleic acids of the invention and host cells containing such vectors.

In certain embodiments, the nucleic acid molecule of the invention further comprises (i) additional nucleic acid molecule encoding a polypeptide that confers a beneficial property to proteins expressed in cells operatively linked to the transcriptional regulator, wherein said transcriptional regulator is a promoter that is transcriptionally active in a eukaryotic cell and (ii) a nucleic acid molecule encoding a protein of interest to be expressed in cells wherein the expression of the nucleic acid molecule of (i) imparts said beneficial property to the polypeptide encoded by the nucleic acid molecule of (ii).

In such embodiments, the molecule of (i) encodes a polypeptide selected from the group consisting of an anti-apoptotic protein; a protein that confers resistance to oxidative stress to a cell; a chaperone protein involved in facilitating protein folding; a protein involved in extracellular secretion of proteins; a glycolytic enzyme; a cell cycle regulation protein; a glycosylation enzyme, or any combination thereof.

The invention also provides a method for protecting a cell under conditions of hyperosmolality comprising:
(a) introducing a polynucleotide into a cell wherein said polynucleotide comprises:
  (i) a nucleic acid molecule encoding an osmo-protective protein or peptide or a regulatory nucleic acid molecule and
  (ii) a polynucleotide encoding a second protein of interest operatively linked to a promoter; and
(b) culturing the cell such that the osmo-protective protein or peptide, or the osmo-protective regulatory nucleic acid and the protein of interest is expressed, thereby protecting the cell under conditions of hyperosmolality and allowing expression of the second protein of interest.

In these embodiments, the osmoprotective-protective protein or peptide may be, for example, a proline or a glycine-betaine, a taurine transporter, a glycine betaine-γ-aminobutyric acid transporter, a sodium-myo-inositol cotransporter, a heat shock protein, an aquaporin, an aldose reductase, or a neuropathy target esterase (NTE).

The invention also provides a method for expressing a protein of interest in a cell under conditions of hyperosmolality comprising:
(a) introducing a polynucleotide into a cell wherein said polynucleotide comprises:
  (i) the nucleic acid molecule that encodes a protein that confers a beneficial property to expressed proteins and
  (ii) a polynucleotide encoding a second protein of interest operatively linked to a promoter; and
(b) culturing the cell such that the expression of nucleic acid molecule of (i) imparts said beneficial property to the polypeptide encoded by the polynucleotide of (ii) when said cells are grown under conditions of hyperosmolality.

In these embodiments, the protein or peptide that confers a beneficial property to proteins expressed in cells may be, for example, an anti-apoptotic protein; a protein that confers resistance to oxidative stress to a cell; a chaperone protein involved in facilitating protein folding; a protein involved in extracellular secretion of proteins; a glycolytic enzyme; a cell cycle regulation protein; a glycosylation enzyme; or any combination thereof.

In the methods of the invention, cells may be cultured initially under normal culture conditions (i.e., with standard tonicity conditions) and subsequently the culture conditions may be altered to increase osmolality to an amount sufficient to increase expression of said second protein of interest. This may be accomplished by spiking the culture with a compound that increases said osmolality.

In some embodiments, the expression of proteins late in the culture (when the culture conditions have increased osmolality) is beneficial for making such proteins as proteins that are toxic to the cell, proteins that are unstable, or proteins that are difficult to express under normal culture conditions.

In other embodiments, the initial culture conditions are standard culture conditions and the culture is allowed to become hyperosmotic in the course of cell culture, thereby increasing expression of said second protein of interest which is under the control of a OR-TRE. These proteins may be proteins that are toxic to the cell, proteins that are unstable, or proteins that are difficult to express under normal culture conditions.

The invention further provides a method for adding or enhancing a cell's adaptability or resistance to osmotic stress or osmotic shock comprising introducing to a cell a polynucleotide comprising the nucleic acid molecule of the invention in which the additional nucleic acid molecule is (a) an osmo-protective protein or peptide; or (b) an osmo-protective regulatory nucleic acid.

The invention further provides a method for expressing a protein of interest in a cell under conditions of hyperosmolality comprising introducing a polynucleotide into a cell wherein said polynucleotide comprises:

(a) a protein-coding nucleic acid molecule encoding TonEBP; and (b) a polynucleotide encoding a second protein of interest operatively linked to a second OR-TRE; wherein under conditions of increased osmolality, the nucleic acid molecule of (a) is expressed, thereby expressing TonEBP protein, and wherein the TonEBP protein positively regulates expression of TonEBP and said second protein of interest. This creates a positive feedback loop system. In these embodiments, the second protein of interest may be, for example, an osmoprotective protein (e.g., a proline or a glycine-betaine, a taurine transporter, a glycine betaine-γ-aminobutyric acid transporter, a sodium-myo-inositol cotransporter, a heat shock protein, an aquaporin, an aldose reductase, or a neuropathy target esterase (NTE)); a protein that imparts a beneficial property to polypeptides expressed by said cells (e.g., an anti-apoptotic protein; a protein that confers resistance to oxidative stress to a cell; a chaperone protein involved in facilitating protein folding; a protein involved in extracellular secretion of proteins; a glycolytic enzyme; a cell cycle regulation protein; a glycosylation enzyme; or any combination thereof). In some embodiments, the method may comprise expression of a third protein of interest operatively linked to a promoter, wherein the protein that imparts a beneficial property acts on the third protein of interest.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

FIG. 1a and FIG. 1b schematically illustrate how osmo-responsive transcriptional regulatory elements (OR-TREs) of this invention increase osmo-tolerance, as discussed in detail, below.

DETAILED DESCRIPTION OF THE INVENTION

Figure 2:
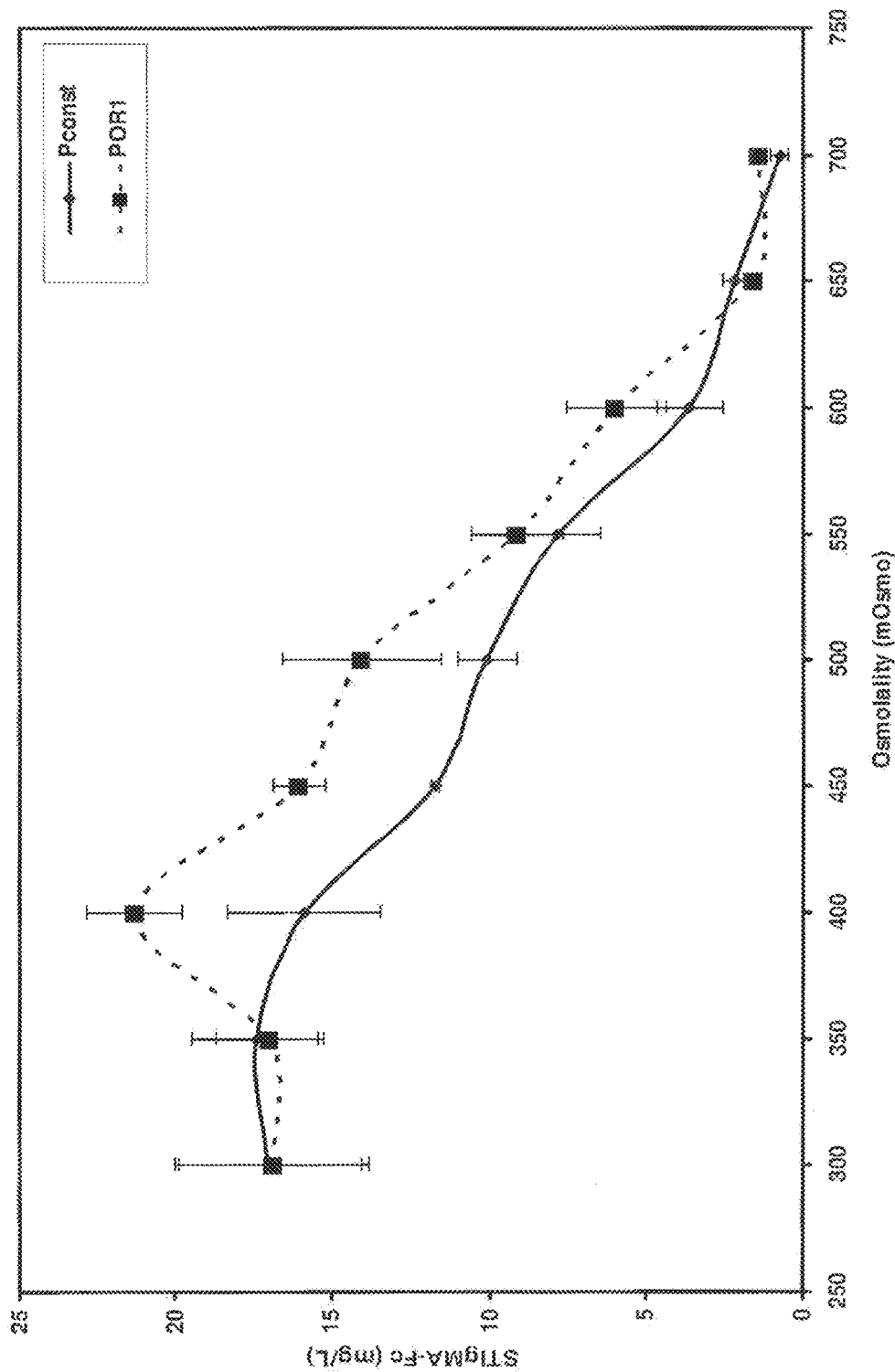
FIG. 2 schematically illustrates an experiment demonstrating the transcriptional up-regulatory activity of a construct of this invention by measuring a marker in supernatants from transfected cells, as described in detail in Example 1, below.

The invention provides compositions and methods for regulating intracellular osmolarity in cells, for example, in cultured cells, such as cells used in bioreactors. In one aspect, the invention provides compositions and methods for regulating intracellular osmolarity in cultured mammalian cells. In one embodiment, the invention provides artificial (recombinant) osmo-sensing, or "osmo-responsive," gene expression systems, and methods for making and using them. In another embodiment, by incorporating these osmo-sensing, or "osmo-responsive," gene expression systems into cells, the invention also provides engineered cells having an enhanced osmo-response, or an enhanced osmo-sensing mechanism. Thus, in one aspect, when these cells are used in culture systems, e.g., in bioreactors, their enhanced osmo-responsiveness (e.g., enhanced resistance to hypertonic or hypotonic osmotic stress) results in better cell health and survival and in an increased or boosted product production in a culture system or bioreactor.

In one embodiment, the constructs of the invention are used as inducible nucleic acid and/or polypeptide expression systems, where the signal that induces or decreases transcription of a construct the invention (e.g., a nucleic acid in a construct of the invention) is a change in osmolarity, osmolality and/or tonicity in the cell's intracellular and/or extracellular environment (e.g., a change causing conditions of hyperosmolality or increasing the degree of hyperosmolality), e.g., in a culture fluid, as in a bioreactor, culture dish, petri dish, test tube, roller bottle, implant, artificial organ, and the like.

In alternative embodiments, because compositions and methods of this invention give an osmo-protective phenotype to a cell, these compositions and methods can be used to increase or boost the generation of (manufacture of) "difficult-to-express" molecules, polypeptides and/or nucleic acids, e.g., molecules, polypeptides and/or nucleic acids that are toxic to a cell, e.g., have inherent host cell toxicity. Compositions and methods as provided herein also are used to increase or boost expression (manufacture) of "difficult to-express" polypeptides that are "difficult-to-express" in the context of "difficult-to-express" properly or as preferred/desired (e.g., a wild type folding pattern), e.g., to increase or boost proper post-translational processing, for example, to increase or boost proper folding and/or preferred/desired glycosylation (e.g., a wild type glycosylation pattern) of polypeptides in cells having post-translational mechanisms that are sensitive to osmotically stressed conditions (e.g., conditions of hyperosmolality), e.g. as in osmotically stressed culture or bioreactor conditions, e.g., as in late stage or cell dense culture environments. In another embodiment, compositions and methods as provided herein also are used to increase or boost expression of "difficult-to-express" polypeptides that are "difficult-to-express" in the context of the proteins that cannot be post-translationally processed properly or in sufficient yields in osmotically stressed conditions (e.g., conditions of hyperosmolality), e.g. as in osmotically stressed culture or bioreactor conditions, e.g., as in late stage or cell dense culture environments, for example, proteins that do not fold or become glycosylated normally or in sufficient yields in osmotically stressed conditions. In alternative embodiments, because higher yields of correct post-translationally modified, e.g., glycosylated or folded, polypeptides are generated by practicing the compositions and methods as provided herein, product quality is maintained in late stage or cell dense culture environments, such as bioreactors. For example, in one aspect, practicing the compositions and methods as provided herein results in maintaining recombinant protein quality in a manufacturing process, e.g., maintaining FDA approved recombinant protein quality in a manufacturing process, particularly when product quality is compromised in late stage or cell dense culture environments, such as bioreactors.

In other embodiments, also because the compositions and methods of this invention impart an osmo-protective phenotype to a cell, these compositions and methods can be used to increase or boost the generation (manufacture) in a dense or late-stage cell production system, including for example a cell culture, or dense or late-stage growth cells in a bioreactor, culture dish, petri dish, test tube, roller bottle, implant, artificial organ, and the like. Accordingly, use of compositions and methods as provided herein allows efficient production of biomolecules in dense or late-stage cell production systems, including allowing higher yields of total biomolecules (e.g., small molecules, polypeptides and/or nucleic acids), or higher yields of post-translationally processed proteins, e.g., higher yields of properly folded or preferably folded (e.g., a wild type folding) or glycosylated polypeptides.

Likewise, the compositions and methods of this invention can be used to induce recombinant protein expression, or to increase the degree of proper protein folding and/or glycosylation in a cell, during culture conditions, including culture conditions after the optimal cell density has been achieved; induction—e.g., an increase in transcription by an OR-TRE of this invention, is triggered by a change (e.g., an increase) in osmolarity, osmolality and/or tonicity in the cell's intracellular and/or extracellular environment (e.g., a change causing conditions of hyperosmolality or increasing the degree of hyperosmolality). The compositions and methods of this invention can be used to decouple cell growth and recombinant protein expression in a cell expression system, e.g., an implant, an artificial organ, a bioreactor, a culture medium and the like. The compositions and methods of this invention can be used as an inducible transcriptional or promoter system under conditions of hyperosmolality, or high osmolarity, osmolality and/or tonicity conditions.

Products produced by cultured cells whose production by the cells in culture is increased by practicing the methods and/or compositions of this invention include recombinant polypeptides, polysaccharides, small molecules such as polyketides (e.g., antibiotics), nucleic acids, virions and packaged viral particles (e.g., as with "producer cells" being the cultured cells), and the like.

Engineered cells of this invention can better resist osmotic stresses (e.g., conditions of hyperosmolality, including enhanced resistance to hypertonic or hypotonic osmotic stresses), they are protected in the face of increasing osmolality (e.g., conditions of hyperosmolality), and in alternative embodiments can maintain both growth and high viability at higher or lower than normal (physiologic) osmolalities. In one embodiment, use of the osmo-sensing, or "osmo-responsive," or "hyperosmolality-responsive," gene expression systems and cells of this invention allow for better culture or bioreactor yields for "difficult-to-express" proteins, for example, by decreasing cell toxicity in osmotically stressed conditions and ensuring a sufficient quantity and consistent quality of a cultured cell product, which can be a recombinant protein product and/or a properly folded or preferably folded (e.g., a wild type folding) or glycosylated protein.

In one embodiment, the invention provides a solution to decreased product yields by cells in osmotically stressed culture conditions by providing a hyperosmolality-sensitive, an osmo-sensing or an osmo-responsive gene expression system; and the invention provides cells that comprise these hyperosmolality-sensitive, osmo-sensing, osmo-responsive systems of the invention, where the cells of the invention have enhanced survival and resistance to the negative effects of conditions of hyperosmolality, hypoosmolality or any osmotically stressed condition(s), including hypertonic or hypotonic osmotic stress. The invention provides compositions, cells and methods for preventing or ameliorating problems caused by hyperosmolality or increased osmolality, e.g., hyperosmolality correlated with (associated with) increased conditions of or tonicity (e.g., increased salt, such as increased sodium or potassium salts, e.g., NaCl), in culture systems such as bioreactors. The invention provides compositions, cells and methods for preventing or ameliorating problems caused by hypo-osmolality or decreased osmolality, e.g., decreased osmolality correlated with (associated with) decreased tonicity (e.g., decreased salt, decreased sodium or potassium salts, e.g., NaCl), in culture systems such as bioreactors.

In alternative aspects, the invention provides compositions, cells and methods for preventing or ameliorating problems caused by hyper-osmolality or increased osmolality, or problems caused by hypo-osmolality or decreased osmolality, wherein the hyperosmolality or hypo-osmolality is caused by increased or decreased, respectively, levels (amounts) of components, ingredients or elements of any culture or buffer system, including for example: inorganic salts and minerals such as, e.g., sodium chloride, calcium chloride, cupric sulfate, ferric nitrate, ferrous sulfate, potassium chloride, magnesium sulfate, magnesium chloride, sodium phosphate monobasic, sodium phosphate dibasic and/or zinc sulfate; or trace elements such as, e.g.: ammonium paramolybdate, ammonium vanadium oxide, manganese sulfate, nickel chloride, selenious acid, sodium metasilicate and/or stannous chloride; or a buffer or buffer ingredient such as, e.g.: a phosphate (including e.g., monosodium phosphate, disodium phosphate), a carbonate and/or a bicarbonate (e.g., a sodium carbonate and/or sodium bicarbonate), HEPES (4-(2-hydroxyethyl)-1-piperazineethanesulfonic acid) and/or sodium butyrate; or any culture ingredient or component that can increase and/or decrease osmolality such as e.g.: a carbohydrate such as a glucose and/or a galactose, any natural or synthetic amino acid, a nucleotide and/or a cofactor, a metabolic intermediate such as e.g.: hypoxanthine, linoleic acid, lipoic acid, putrescine dihydrochloride, sodium pyruvate and/or thymidine, or a vitamin or any other organic compounds required at a low concentration such as: biotin, D-calcium pantothenate, choline chloride, cyanocobalamin, folic acid, i-inositol, niacinamide, pyridoxal, pyridoxine, riboflavin, thiamine, a hormone and/or a cofactor, for example insulin, transferrin and epidermal growth factor, or a peptides, a protein and/or a tissue hydrolysate (e.g., a peptone), or an antibiotic, for example, gentamicin sulfate, or a fatty acid such as linoleic acid, alpha tocopherol, lipid/EtOH, or a block copolymer, e.g., a polymer based on ethylene oxide and propylene oxide, e.g., PLURONIC™ (BASF, Florham Park, N.J.), that can function as an antifoaming agent, a wetting agent, a dispersant, a thickener, an emulsifier, a surfactant, an osmoprotectant, for example proline, glutamate, sorbitol, betaine, inositol, taurine and/or glycerol-phosphocholine.

In one embodiment, one or more osmoprotectant compounds are used when practicing the compositions and/or methods of this invention to augment the osmoprotective effect of practicing this invention; for example, compositions and/or methods of this invention include (comprise) use of one or more osmoprotectant compounds such as proline, glutamate, sorbitol, betaine, inositol, taurine and/or glycerol phosphocholine.

Compositions of the invention, e.g., the osmo-responsive transcriptional regulatory elements (OR-TREs) of the invention, comprise at least one tonicity enhancer binding protein (TonEBP) (also known as "osmotic response element-binding protein (OREBP)" or "NFAT5")-responsive transcriptional enhancer sequence (an ORE/TonE enhancer sequence) and/or an OR-TRE of the invention can comprise an NFATc tonicity-responsive transcriptional factor. Osmotic stress, including conditions of hyperosmolality caused by e.g., high salt (high sodium or potassium salts, e.g., NaCl) conditions, activates a transcription factor tonicity-responsive enhancer/osmotic response element-binding protein (NFATc or TonEBP/OREBP) by phosphorylation (although the invention is not limited by any particular mechanism of action), and the phosphorylated TonEBP/OREBP translocates from the cytoplasm to the nucleus, resulting in increased transcription of both the osmo-responsive transcriptional regulatory elements (OR-TREs) of the invention and endogenous osmo-responsive transcriptional regulatory elements.

Activation of endogenous osmo-responsive transcriptional regulatory elements increases expression (transcription) of several protective nucleic acids, e.g., genes, whose promoters are controlled by the enhancer ORE/TonE, including the taurine transporter (TauT), the glycine betaine-γ-aminobutyric acid transporter (BGT1), the sodium-myo-inositol cotransporter, heat shock protein 70 (HSP70), aquaporin 2 (AQP2) and the aldose reductase gene (AR); and in alternative embodiments, the osmo-responsive nucleic acids of this invention comprise coding sequence(s) for these osmo-responsive endogenous nucleic acids, e.g., genes. Thus, in one aspect, the compositions and methods of the invention impart osmo-resistance to cells by the osmo-responsive expression of osmo-responsive endogenous nucleic acids, e.g., genes, incorporated (engineered) into the compositions of the invention; e.g., including the taurine transporter (TauT), the glycine betaine-γ-aminobutyric acid transporter (BGT1), the sodium-myo-inositol cotransporter, heat shock protein 70 (HSP70), aquaporin 2 (AQP2) and/or the aldose reductase gene (AR).

However, in alternative aspects, the compositions and methods of the invention impart osmo-resistance to cells by the osmo-responsive expression of nucleic acids, e.g., genes (and proteins) heterologous the cells into which they have been inserted. For example, the taurine transporter (TauT), the glycine betaine-γ-aminobutyric acid transporter (BGT1), the sodium-myo-inositol cotransporter, heat shock protein 70 (HSP70), aquaporin 2 (AQP2) and/or the aldose reductase gene (AR) can be heterologous to the cell. The compositions and methods of the invention also can impart osmo-resistance to cells by the osmo-responsive expression of an endogenous or heterologous osmo-protective protein or peptide, such as a proline or a glycine-betaine, or a taurine transporter, or a glycine betaine-γ-aminobutyric acid transporter, or a sodium-myo-inositol cotransporter, or a heat shock protein, or a heat shock protein 70, or an aquaporin (a membrane pore protein acting as a water channel), or an aquaporin 2, or an aldose reductase.

The compositions and methods of the invention also can impart osmo-resistance to cells by the osmo-responsive expression of an endogenous or heterologous osmo protective anti-apoptotic protein, such as Bcl-2, Bcl-xL, Mcl-1, BHRF1, X-IAP, IAP1, IAP2 IEX-1L, Bfl-1 or Bcl-w.

The compositions and methods of the invention also can impart osmo-resistance to cells by the osmo-responsive expression of an endogenous or heterologous protein that confers resistance to oxidative stress to a cell, such as a superoxide dismutase, a catalase, a glutathione peroxidase, a peroxiredoxin, a sulfiredoxin, thioredoxin, thioredoxin reductase, thioredoxin peroxidase, thioltransferase, glutaredoxin or a glutathione reductase.

The compositions and methods of the invention protect cells against osmotic stress, e.g., protect again conditions of hyperosmolality, to ameliorate or prevent adverse consequences such as, but not limited to, unfolded or misfolded proteins, etc. Thus, in alternative embodiments, the compositions and methods of the invention enable a cell, including cultured cells, to generate and secrete more endogenous product, including proteins or proteins in a correct folding state and/or having better (normal, wild type) glycosylation profiles, etc. In one aspect, the compositions and methods of the invention can impart osmo-resistance to cells by the osmo-responsive expression of an endogenous or heterologous chaperone protein involved in facilitating protein folding, including the so-called unfolded protein response (or "UPR," which is activated in response to an accumulation of unfolded or misfolded proteins to prevent programmed cell death or apoptosis triggered by an accumulation of unfolded or misfolded proteins), such as a binding immunoglobulin protein (BiP) (also called glucose regulated protein 78, or Grp78), calnexin, calreticulin, ERp57, or a protein disulfide isomerase (PDI).

The compositions and methods of the invention also can impart osmo-resistance to cells by the osmo-responsive expression of an endogenous or heterologous protein involved in extracellular secretion of proteins.

The compositions and methods of the invention also can impart osmo-resistance to cells by the osmo-responsive expression of an endogenous or heterologous glycolytic enzyme, e.g., a pyruvate carboxylase or a pyruvate kinase.

The compositions and methods of the invention also can impart osmo-resistance to cells by the osmo-responsive expression of an endogenous or heterologous cell cycle regulation protein, e.g., a cyclin or a cyclin-dependent kinase (a CDK), or an inhibitor of a cyclin or a cyclin-dependent kinase.

In one aspect, the osmo-responsive nucleic acid sequences of this invention can be used to enhance/increase recombinant protein production in mammalian cell cultures by, e.g., ameliorating cell stress subsequent to osmotic stress. The invention also provides methods of using these osmo-responsive nucleic acid sequences of this invention.

The invention also provides nucleic acids in which expression of genes of interest are under the control of osmoresponse elements such that proteins of interest may be expressed under conditions of increased osmolality. In these cases the OR-TRE is operative linked to the nucleic acid encoding the gene of interest. In these embodiments, the nucleic acids may also contain OR-TRE controlled osmo-resistant genes or nucleic acids, and/or nucleic acids encoding proteins or peptides that confer a beneficial effect on expressed proteins which could be, for example, an effect on the cell's metabolism, secretion, viability or growth, or may be something that has a beneficial effect on the quality of the expressed protein, such as correct folding, post-translational modifications and the like.

The invention also provides a positive feedback mechanism in which the OR-TRE directs expression of TonEBP such that the protein may then drive further expression of TonEBP. When used in conjunction with other genes under the control of OR-TRE, the positive feedback has the effect of driving expression of these genes as well. The positive feedback may provide enhanced adaptability of the cells to hyperosmolality.

One may artificially increase the osmolality of the culture to drive the expression of genes under the control of OR-TRE's in a regulated, predictable fashion to time protein production to optimize certain properties. Alternatively, by placing expression of genes under the control of OR-TRE, genes may be expressed late in the culture stages as osmolality naturally increases. These methods may be useful in expressing proteins that are toxic to cells, proteins that are unstable, and proteins that are simply difficult to express under standard culture conditions.

The invention also provides a variety of novel artificial promoters that enable tonicity-responsive gene expression and their possible applications for recombinant protein manufacturing. In one aspect, nucleic acids of the invention comprise osmo-responsive mammalian promoters; and alternatively, in one aspect nucleic acids of the invention comprise an osmo-responsive untranslated region of the TonEBP mRNA for osmo-sensitive expression of a nucleic acid sequence of interest.

In one embodiment, the nucleic acids of the invention comprise TonEBP/OREBP responsive promoters comprising one or multiple operator module(s) specific of the TonEBP/OREBP enhanceosome cloned upstream of a minimal eukaryotic promoter. In one aspect, the nucleotide sequence −1053 to −1007 of the mouse aldose reductase promoter (see, e.g., Daoudal (1997) J. Biol. Chem. January 31; 272(5):2615-2619) which contains the TonE at position −1053 and an activator protein 1 (AP-1) site at position −1014, is used.

In alternative aspects, nucleic acids of this invention countering the effects of increased osmolality on recombinant protein production by insertion of one or multiple osmotic-response elements upstream or within the promoter sequence that drives the expression of a transgene, thus increasing its transcriptional activity as osmolality increases. For example, in natural systems, almost all of the tonicity responsive genes have one or more activator protein-1 (AP-1)-responsive sites within 35 bp of a TonE; and in alternative aspects, nucleic acids of this invention comprise one or a plurality of AP-1 sites (AP-1 binding sequences) within a similar distance (more, less or the same) of a TonE site. Presence of one or more AP-1 responsive motifs in the nucleic acids of this invention contributes to high NaCl-induced responsiveness, e.g., in this aspect, the AP-1 responsive motif-comprising osmo-responsive transcriptional regulatory elements (ORTRE) of this invention are more sensitized or more responsive (more tonicity-responsive) to osmo-stress conditions, e.g., more sensitized or more responsive to high salt (e.g., sodium or potassium salts, e.g., NaCl) culture conditions. This invention uses a variety of transgene expression alternatives, or windows, made possible by varying the number of osmotic response elements, e.g., TonE and/or AP-1, operatively linked to a promoter sequence to fine-tune transgene (a "gene of interest") expression levels to a desired level, e.g., from a basal expression to a higher, or maximal, expression in osmotically stressed (e.g., hypotonic or hypertonic) conditions.

In one embodiment, an increase in cell hyperosmolality-responsiveness (e.g., tonicity-responsiveness) is mediated by a nucleic acid of the invention increasing the rate of transcription of a nucleic acid molecule, such as a transgene, or "gene of interest," as mediated/controlled by the transcription unit's promoter. For example, in one aspect, an increase in hyperosmolality-responsive (e.g., tonicity-responsive) NFATc/OREBP or TonEBP/OREBP gene transactivating activity is mediated by the promoter of the osmo-responsive transcriptional regulatory element (OR-TRE) of the invention. In alternative embodiments, any promoter transcriptionally active in a eukaryotic cell can be used in an osmo-responsive transcriptional regulatory element (OR-TRE) of this invention, e.g., a promoter comprising or consisting of a constitutive promoter or an inducible promoter, or a synthetic promoter, or a mammalian, plant, insect, bacterial, yeast, fungal or viral promoter, or a cytomegalovirus (CMV) promoter, e.g., a minimal promoter consisting of a fragment of a human CMV promoter. In one aspect, a minimal transcription unit is used, e.g., a minimal or stripped down version of an expression vector, e.g., as described herein, to most efficiently express the nucleic acid molecule (e.g., transgene or gene of interest).

While the invention is not limited by any particular mechanism of action, in one aspect the osmo-responsive transcriptional regulatory elements (OR-TREs) of this invention increase osmo-tolerance because of the cell's TonEBP-driven positive feed-back loop for TonEBP expression, as schematically illustrated in FIG. 1a and FIG. 1b.

The compositions and methods of the invention ameliorate the increased osmolality correlated with increased tonicity (increased salt, such as sodium or potassium salts, e.g., or NaCl). In one aspect, high salt (sodium or potassium salts) in the culture environment activates the transcription factor tonicity-responsive enhancer/osmotic response element binding protein (TonEBP/OREBP) of the invention, resulting in increased transcription of the osmo-protective genes incorporated into the constructs of the invention. In these constructs, promoters are controlled by, e.g., an osmo-responsive transcriptional regulatory element (OR-TRE), or the enhancer ORE/TonE, which in one aspect includes one or more AP-1 protein binding sequences.

While the invention is not limited by any particular mechanism of action, in one aspect regulation of TonEBP/OREBP transcriptional activity is as schematically represented in FIG. 1a; this scheme involves nucleo-cytoplasmic trafficking, transactivation, and phosphorylation. In one aspect, within 30 min of hypertonicity, TonEBP/OREBP becomes phosphorylated and its nuclear distribution, i.e. the ratio of amount in the nuclear fraction to the amount in the cytoplasmic fraction, increases. In one aspect, TonEBP's transactivation depends on tonicity: TonEBP's transcriptional activity is positive under isotonic conditions, decreases in hypotonicity and increases in hypertonicity.

FIG. 1a schematically represents how TonEBP is stimulated by hypertonicity and induces transcription of promoters containing one or multiple TonEBP's cognate binding site(s): ORE/TonE. In one embodiment, any endogenous TonE (tonicity enhancer, also called the osmotic response element) containing promoter can be used to drive the expression of a recombinant protein for enhanced biopharmaceutical production.

FIG. 1b schematically represents an example of application of the osmo dependent activity of TonEBP: an osmo-responsive positive feedback loop. However, noting the invention is not limited by any particular mechanism of action, FIG. 1b pictures one of many possible exemplary mechanisms of action: a TonEBP-responsive positive feedback loop where TonEBP transactivates its own expression so that when tonicity increases, TonEBP synthetically amplifies its own stimulation: the greater the osmo-responsive activation of TonEBP, the more TonEBP is produced resulting in greater feedback.

In designing constructs of this invention, the osmo-responsive transcriptional regulatory element (OR-TRE) of this invention can transactivate a variety of osmoprotective genes, thus enabling the cells to adapt to high osmolality. In one exemplary mechanism, such an osmo-responsive positive feed-back loop could both accelerate and amplify the adaptation of mammalian cells to osmotic stress. It would increase their tolerance to high osmolality without the disadvantages of constitutive overexpression.

In some aspects, a constitutive overexpression of TonEBP could represent a superfluous drain of energy for the cells in isotonic conditions; however, because the invention encompasses osmo-responsive transcriptional regulatory elements (OR-TREs) capable of creating an osmo-resistant phenotype to any cell expressing any recombinant protein, under some circumstances it is envisioned a construct or a cell of the invention may be designed to constitutively express a gene that lends some degree of osmo-resistance to a cell. In alternative embodiments, the constructs of this invention are osmo-responsive in that they can be responsive to increases or decreases in intracellular and/or extracellular osmolality, osmolarity and/or tonicity. In alternative embodiments, osmo-responsive means any change in osmolality or osmolarity, e.g., any decrease or increase in osmolality or osmolarity, e.g., any change in molality, including any change in (e.g., increasing or decreasing conditions of) hyperosmolality or hypo-osmolality. In one aspect, "osmolality" is a measure of the osmotic pressure of dissolved solute particles in an aqueous solution. The solute particles include both ions and non-ionized molecules.

Osmolality is expressed as the concentration of osmotically active particles (i.e., osmoles) dissolved in 1 kg of water (1 mOsm/kg H2O at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts (e.g., sodium or potassium salts), sugars, metabolites, organic acids, lipids, etc. In one embodiment, the concentration of amino acids and salts, e.g., sodium and potassium salts (e.g., NaCl) in the culture medium is increased in order to achieve the desired osmolality ranges set forth herein. When used herein, the abbreviation "mOsm" means "milliosmoles/kg H2O".

For example, in one embodiment, the compositions and methods provided herein are used to maintain a cell culture medium, e.g., a found in a bioreactor, to have osmolarity in the range of between about 210 and 350 milliosmoles (mOsm), or in the range of between about 260 and 320 milliosmoles (mOsm), or in alternative embodiments targeting a cell culture osmolarity of about 280, 290, 300 or 310 mOsm/kg.

In an alternative embodiment, the compositions and methods provided herein are used to maintain a cell culture medium of relatively low osmolarity, e.g., for maintaining a cell culture medium having an osmolarity of about 248 mOsm to about 280 mOsm, see e.g., U.S. Pat. No. 5,747,341. In an alternative embodiment, the compositions and methods provided herein are used to maintain a cell culture medium of between about 280 to 330 mOsm, or between about 400 to 600 mOsm, e.g., as described in U.S. Patent App. Pub. No. 20050272124. In an alternative embodiment, the compositions and methods provided herein are used to maintain a cell culture medium of between about 250 to about 600 mOsm, as described e.g., in U.S. Pat. No. 5,705,364.

Environment or Stress Resistance Proteins

The invention provides osmo-responsive nucleic acids comprising at least one of the osmo-responsive transcriptional regulatory elements of the invention operatively linked to a nucleic acid encoding an osmo-protective protein or peptide; an anti-apoptotic protein; a protein that confers resistance to oxidative stress to a cell; a chaperone protein involved in facilitating protein folding; a protein involved in extracellular secretion of proteins; a glycolytic enzyme; a cell cycle regulation protein; or any combination thereof.

Osmo-Protective Genes

The invention provides osmo-responsive nucleic acids that encode proteins that favorably effect mammalian cells water content and/or osmotic potential. For example, the nucleic acids of this invention can osmo-responsively express nucleic acids encoding the biosynthesis of any protein that effects mammalian cells water content and/or osmotic potential, e.g., proline and glycine-betaine, and/or proteins affecting levels of other osmotically active solutes such as sugars.

Nucleic acids of this invention can osmo-responsively express a plurality of genes that improve osmotic resistance and have complementary modes of action. Combinations of these genes expressed by nucleic acids of this invention can have additive and/or synergistic effects in improving osmotic resistance in a cell, e.g., in a mammalian cell. In alternative embodiments, benefit is conferred via constitutive expression of one or more of these genes, and/or by also expressing one or more in an osmo-responsive manner, e.g., using an osmo-responsive transcriptional and/or post-transcriptional expression system of this invention. By providing a variety of combinations of both constitutive and osmo-induced increase in expression of proteins that provide engineered cells an enhanced osmo-response, or an enhanced osmo-sensing mechanism, the invention can be designed or fitted to have osmo-sensitive expression patterns suitable for any cell, e.g., for any mammalian cell, expressing any recombinant protein, to better withstand the stress of hyper- or hypo-osmolarity. For example, the compositions and methods of the invention can be used to ameliorate or prevent lactate production that acidifies culture conditions, e.g., in a culture system or a bioreactor. In most culture systems and bioreactors, in order to maintain the pH of the medium, base is pumped in and osmolality increases as a result.

There is a correlation between lactate accumulation and decreased cell growth and viability in fedbatch bioreactors. Thus, osmo-responsive overexpressing of glycolytic enzymes such as pyruvate carboxylase, pyruvate kinase and other enzymes by the compositions and methods of the invention enables a transformed cell, e.g., a mammalian cell, to switch from lactate production to lactate consumption. The result of this overexpressing of glycolytic enzyme(s) is maintaining of viability by the cell and increased recombinant protein production by the cell, e.g., the mammalian cell.

Generating and Manipulating Nucleic Acids and Vectors

The invention provides nucleic acids comprising an osmo-responsive transcriptional regulatory element (OR-TRE), osmo-responsive nucleic acids, and expression cassettes, vectors, recombinant viruses, plasmids, phages, phagemids, artificial chromosomes and cloning vehicles comprising them. The invention can be practiced in conjunction with any method or protocol or device known in the art, which are well described in the scientific and patent literature.

The invention provides "nucleic acids" or "nucleic acid sequences" comprising an osmo-responsive transcriptional regulatory element (OR-TRE), or osmo-responsive nucleic acids, and also includes RNAi such as siRNA or miRNA, oligonucleotides, nucleotides, polynucleotides, or any fragments of these, including DNA or RNA (e.g., mRNA, rRNA, tRNA) of genomic or synthetic origin, which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). Nucleic acids of the invention can encode polypeptides as described herein, and can comprise not only the coding sequence but also leader sequences or proprotein sequences and non-coding sequences, such as introns or non-coding sequences 5' and/or 3' of a coding sequence. Thus, a polynucleotide used to practice this invention can include the coding sequence for a polypeptide as well as a polynucleotide which includes additional coding and/or noncoding sequence.

General Techniques

The nucleic acids used to practice this invention, whether the osmo-responsive transcriptional regulatory element (OR-TRE), osmo-responsive nucleic acids of this invention, or the RNA, iRNA, regulatory nucleic acids (a nucleic acid having an inhibitory, stabilizing or upregulating function or effect), cDNA, genomic DNA, vectors, viruses or hybrids thereof used to practice this invention, may be isolated from a variety of sources, genetically engineered, amplified, and/or expressed/generated recombinantly.

Recombinant nucleic acids and/or polypeptides can be individually isolated or cloned and tested for a desired activity. Any recombinant expression system can be used, including bacterial, mammalian, yeast, insect or plant cell expression systems.

Alternatively, nucleic acids used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice this invention is to clone from genomic samples, and, if desired, screen and re clone inserts isolated or amplified from, e.g., genomic clones or cDNA clones. Sources of nucleic acid used to practice this invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

Transcriptional and Translational Control Sequences

The nucleic acid sequences of the invention comprise promoters and enhancers operatively linked to protein coding sequences or regulatory nucleic acids, e.g., an inhibitory, stabilizing or a up-regulating nucleic acid molecules, to direct or modulate RNA synthesis/expression. For example, in one aspect the invention provides at least one tonicity enhancer-binding protein (TonEBP)-responsive transcriptional enhancer sequence upstream (5' to) and operatively linked to a promoter sequence transcriptionally active in a eukaryotic cell. Additional enhancer sequence can also be operatively linked to the osmo-responsive transcriptional regulatory elements (OR-TREs) of the invention.

Any transcriptional regulatory sequence, e.g., a promoter or an enhancer sequence, operable in a eukaryotic cell, e.g., a mammalian cell, can be used to practice this invention, e.g., be used in a nucleic acid construct of this invention. For example, in alternative embodiments a promoter used to practice this invention is a minimal promoter (also called a "core promoter"), an inducible promoter, or a constitutive promoter. A transcriptional regulatory sequence, e.g., a promoter an enhancer sequence, is "operably linked to" a sequence to be transcribed, e.g., a protein coding sequence, when RNA polymerase which initiates transcription at the promoter will transcribe the coding sequence into an RNA, e.g., an mRNA. In one embodiment, a promoter as used herein is a regulatory region of (in) a nucleic acid, e.g., a DNA or gene, which can be located upstream (i.e., towards the 5' region of the sense strand) of the nucleic acid or gene to be transcribed, thus, the promoter initiates (allows) transcription of the nucleic acid or gene.

In alternative embodiments, a transcriptional regulatory sequence, e.g., a promoter or an enhancer sequence, can be "operably linked to" a sequence to be transcribed, e.g., a protein coding sequence, or a regulatory nucleic acid such as an inhibitory, stabilizing or a up-regulating nucleic acid molecule, or an antisense or other inhibitory sequence (such as miRNA or siRNA) even if the promoter or enhancer is not close (proximal) to the sequence to be transcribed; in other words, there is no limit to the distance a transcriptional regulatory sequence (e.g., as an enhancer such as AP-1 or a TonEBP-responsive transcriptional enhancer) is to (is positioned in relation to) the sequence to be transcribed (e.g., 20, 30, 40, 50, 100, 150, 200, 250, 300, 350, 400 or 500 or more residues), and there is no limitation on its placement on a construct (in or within a construct); noting that in some embodiments the transcriptional regulatory sequence is cis to the sequence to be transcribed, while in other aspects it is trans to the sequence to be transcribed.

In alternative embodiments, the transcriptional regulatory sequence, e.g., a promoter or an enhancer sequence (e.g., an AP-1 or a TonEBP-responsive transcriptional enhancer), can be in a sense or antisense orientation to the sequence to be transcribed, or on the same or on an opposing strand to the sequence to be transcribed.

Any minimal promoter can be used, e.g., a core promoter or minimal promoter that is the minimal portion of a promoter sequence or motif required to properly initiate transcription. In one aspect, a minimal or core promoter used to practice the invention is or comprises a fragment of a human CMV promoter; minimal promoters (core promoters) and methods of identifying them and making them are well known in the art, e.g., see Baliga (2001) Biol. Proceed. Online 3:64-69; Hettiarachchi (2003) Nucleic Acids Res. 31(18):5256-5265. For example, part of the domain A of the CaMV 35S promoter containing a TATA box and extending from the −90 position to the transcription start site +1, can be used as a "minimal promoter." Apart from the TATA box, which is the binding site for RNA polymerase II, this minimal promoter contains a least three CAAT-like boxes; these sequences potentiate the activity of upstream sequences and influence the efficiency of the promoter activity. In one aspect, these CAAT-like boxes are used alone or are attached to heterologous promoter regions to drive the expression of constructs of this invention. Other exemplary "minimal promoters" that can be used to practice this invention include a promoter comprising a CCCACCCCC (CCAC box) sequence as described e.g., by Bassel-Duby (1992) Mol. Cell Biol. 12(11): 5024-5032; or an RNA polymerase II core promoter as described e.g., by Juven-Gershon (2008) Curr. Opin. Cell Biol. 20(3):253-9. Epub 2008 Apr. 22; Juven-Gershon (2006) Biochem. Soc. Trans. 34(Pt 6):1047-50; or the minimal promoter from the myosin heavy chain gene (−164 to +16); see e.g., Smith (1998) Am. J. Physiol. 274(5 Pt 1):C1188-95.

Exemplary eukaryotic promoters that can be used to practice this invention include CMV immediate early, HSV thymidine kinase, early and late SV40, LTRs from retrovirus, mouse metallothionein I, heat shock promoters, the early and late SV40 promoter, LTRs from retroviruses, and the mouse metallothionein-I promoter. Any promoters known to control expression of genes in prokaryotic or eukaryotic cells or their viruses may also be used. Promoters that can be used to practice this invention also include the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK) and the acid phosphatase promoter; fungal promoters and the like.

Exemplary plant promoters that can be used to practice this invention include both inducible and constitutive promoters, e.g., constitutive promoters such as the cauliflower mosaic virus (CaMV) 35S transcription initiation region, the 1'- or 2'-promoter derived from T-DNA of *Agrobacterium tumefaciens*; and/or promoters inducible, e.g., upon exposure to plant hormones, such as auxins; and other transcription initiation regions from known plant genes.

Any enhancer and/or promoters known to control expression of genes in prokaryotic or eukaryotic cells or their viruses may also be used. In alternative embodiments, as used herein an enhancer is a short region of nucleic acid, e.g., DNA, that can specifically bind a protein, which can be called an activator, or an enhancer binding protein. In one aspect, binding of activators to this enhancer region can initiate the transcription of a protein coding sequence, e.g., a gene, or affect (initiate, stop, increase or decrease) the activity of a promoter. The promoter and/or gene effected by, or "operably linked to," the enhancer can be considerable distance away from the enhancer, or can even be on a different vector or chromosome. In alternative embodiments, the increase or decrease in transcription effected by the enhancer on the promoter can be due to the activators bound to the enhancer directly or indirectly effecting the recruiting of additional "transcription factors" to the enhancer on the promoter, which can enhance the binding of other proteins necessary for transcription, such as RNA or DNA polymerases.

In one aspect, expression cassettes, vectors, recombinant viruses, plasmids, phages, phagemids, artificial chromosomes and cloning vehicles of the invention expressed in eukaryotic cells can also contain additional enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

The early and late promoters of the SV40 virus are conveniently obtained as an SV40 restriction fragment that also contains the SV40 viral origin of replication. Fiers et al., Nature, 273:113 (1978); Mulligan and Berg, Science, 209: 1422-1427 (1980); Pavlakis et al., Proc. *Natl. Acad. Sci. USA*, 78:7398-7402 (1981). The immediate early promoter of the human cytomegalovirus is conveniently obtained as a HindIII E restriction fragment. Greenaway et al., Gene, 18:355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature, 295:503-508 (1982) on expressing cDNA encoding immune interferon in monkey cells; Reyes et al., Nature, 297:598-601 (1982) on expression of human β-interferon cDNA in mouse cells under the control of a thymidine kinase promoter from herpes simplex virus; Canaani (1982) *Proc. Natl. Acad. Sci. USA* 79:5166-5170, on expression of the human interferon 31 gene in cultured mouse and rabbit cells; and Gorman (1982) *Proc. Natl. Acad. Sci. USA* 79:6777-6781, on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Other methods, vectors, and host cells suitable for adaptation to the synthesis of the polypeptide of interest in recombinant vertebrate cell culture are described in Gething et al., Nature, 293:620-625 (1981); Mantei et al., Nature, 281:40-46 (1979); Levinson et al.; EP 117,060; and EP 117,058. In one embodiment, a plasmid used to practice this invention for mammalian cell culture expression of a composition of this invention, including any nucleic acid or polypeptide, is pRK5 (EP Pub. no. 307,247) or pSVI6B (PCT Pub. no. WO 91/08291, published 13 Jun. 1991).

Expression Vectors and Cloning Vehicles

The invention provides expression cassettes, vectors, recombinant viruses, plasmids, phages, phagemids, artificial chromosomes and cloning vehicles comprising the nucleic acids of the invention (comprising an osmo-responsive transcriptional regulatory element (OR-TRE) of the invention), and/or a osmo-responsive nucleic acid of the invention, including osmo-regulatory nucleic acids of the invention. Viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1 based artificial chromosomes, yeast plasmids, yeast artificial chromosomes, and any other vectors specific for specific hosts of interest (such as mammalian cells) can be used to practice the invention. In one aspect, the expression cassettes, vectors, recombinant viruses, plasmids, phages, phagemids, artificial chromosomes and cloning vehicles used to practice the invention can include chromosomal, non-chromosomal and synthetic DNA sequences. Large numbers of suitable vectors are known to those of skill in the art, and are commercially available.

Exemplary vectors are include eukaryotic vectors such as pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention.

The expression cassettes, vectors, recombinant viruses, plasmids, phages, phagemids, artificial chromosomes and cloning vehicles used to practice the invention can comprise a promoter, a ribosome binding site for translation initiation and a transcription terminator; and may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector.

Constructs for integrating vectors are well known in the art. Exemplary eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Mammalian expression vectors may also comprise an origin of replication, any necessary ribosome binding sites, a polyadenylation site, splice donor and acceptor sites, transcriptional termination sequences and 5' flanking non-transcribed sequences. In some aspects, DNA sequences derived from the SV40 splice and polyadenylation sites may be used to provide the required nontranscribed genetic elements.

In alternative aspects, nucleic acids of the invention, e.g., those comprising an osmo-responsive transcriptional regulatory element (OR-TRE), and/or osmo-responsive nucleic acids of the invention, are episomal or are stably integrated into the genome of a cell, e.g., a cell to be cultured.

For stable integration of a nucleic acid construct of this invention, any suitable carrier or vehicle can be used, e.g., a lentiviral vector and/or packaging system as described, e.g., in U.S. Pat. Nos. 7,311,907; 7,262,049, describing a pseudotyped lentiviral vector; U.S. Pat. Nos. 7,250,299; 7,226,780; 7,220,578; 7,211,247; 7,160,721, describing methods for enhancing cell growth and increasing the density of cell cultures containing lentivirus-infected host cells; U.S. Pat. Nos. 7,078,031; 7,070,993; 7,056,699; 6,955,919; to name just a few vectors and packaging systems that can be used to practice this invention.

For episomal transfer of a nucleic acid construct of this invention, any suitable carrier or vehicle can be used, e.g., a stable nuclear episomal vector as described in U.S. Pat. No. 7,294,505; a lentiviral vector system for episomal replication of a desired gene as described in U.S. Pat. No. 6,808,923; an episomal expression vector for tissue-specific gene expression as described in U.S. Pat. No. 6,797,494; human papillomavirus vectors for episomal transduction as described in U.S. Pat. No. 6,605,281; an episomal vector as described in U.S. Pat. No. 6,479,279 or 6,410,314; to name just a few vectors and packaging systems that can be used to practice this invention.

Other expression cassettes, vectors, recombinant viruses, plasmids, phages, phagemids, artificial chromosomes or cloning vehicles and systems that can be used to practice this invention include, e.g., replication-competent adenoviral vectors as described in U.S. Pat. No. 7,371,570; adenovirus (Ad) based trans-packaging systems as described in U.S. Pat. No. 7,348,178; an adenovirus as described in U.S. Pat. Nos. 7,323,177; 7,319,033; 7,318,919; or 7,306,793; to name just a few vectors and packaging systems that can be used to practice this invention.

Marker Genes

In one aspect, the expression cassettes, vectors, recombinant viruses, plasmids, phages, phagemids, artificial chromosomes and cloning vehicles used to practice the invention contain one or more selectable marker genes to permit selection of host cells, e.g., mammalian cells, containing a nucleic acid of this invention.

Exemplary selectable markers include genes encoding dihydrofolate reductase or genes conferring neomycin resistance for eukaryotic cell culture, genes conferring tetracycline or ampicillin resistance. Expression cassettes, vectors, recombinant viruses, plasmids, phages, phagemids, artificial chromosomes and cloning vehicles used to practice the invention may also include a selectable marker gene to allow for the selection of cells that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

In one aspect, in order to improve the ability to identify transfected cells, one or more selectable or screenable marker nucleic acids are used as, or in addition to, the expressible gene of interest. "Marker genes" or "marker nucleic acids" are nucleic acids that impart a distinct phenotype to cells expressing the marker gene/nucleic acid, thus allowing the transfected cells to be distinguished from cells that do not have the marker.

"Marker genes" or "marker nucleic acids" may encode either a selectable or screenable marker, depending on whether the marker confers a trait which one can "select" for by chemical means, i.e., through the use of a selective agent (e.g. an antibiotic or the like), or whether it is simply a trait that one can identify through observation or testing, i.e., by "screening". For example, the green fluorescent protein or any other fluorescent protein, bioluminescent proteins of the luciferase type, and the like. Many examples of suitable marker genes are known to the art and can be employed in the practice of this invention.

"Marker genes" or "marker nucleic acids" also can encode a "secretable marker" whose secretion can be detected as a means of identifying or selecting for transfected cells. Examples include marker which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., secreted alkaline phosphatase, secreted luciferase, the *Bacillus stearothermophilus*-derived secreted a-amylase (SAMY), *Bacillus subtilis*-derived xylanase A derivatives) and membrane bound or transiently membrane bound proteins. Any selectable marker can be used to practice this invention, and selectable markers suitable for cell transfections, including mammalian cell transfections, are known in the art. Such markers may include but are not limited to: adenosine deaminase, aminoglycoside phosphotransferase (in combination with neomycin), bleomycin resistance gene (in combination with phleomycin or bleomycin or zeocin), cytosine deaminase (in combination with N-(phosphonacetyl)-L-aspartate, inosine, and cytosine), dihydrofolate reductase (DHFR) (in combination with methotrexate), histidinol dehydrogenase (in combination with histidinol), hygromycin-B-phosphotransferase (in combination with hygromycin), thymidine kinase and xanthine-guanine phosphoribosyltransferase. When using an adenosine deaminase marker, cells that incorporate the gene can be selected by growth in the presence of low concentrations of the ADA inhibitor 2'-deoxycoformycin with cytotoxic concentrations of adenosine or its analogue 9-β-D-xylofuranosyl adenine.

Host Cells and Transformed Cells

The invention also provides transformed or transfected cells comprising a nucleic acid construct of the invention, e.g., an osmo-responsive transcriptional regulatory element (OR-TRE) of the invention, or an osmo-responsive or osmoregulatory nucleic acid of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia, Bacillus, Streptomyces, Salmonella, Pseudomonas* and *Staphylococcus*, including, e.g., *Escherichia coli, Lactococcus lactis, Bacillus subtilis, Bacillus cereus, Salmonella typhimurium, Pseudomonas fluorescens*. Exemplary fungal cells include any species of *Aspergillus*. Exemplary yeast cells include any species of *Pichia, Saccharomyces, Schizosaccharomyces*, or *Schwanniomyces*, including *Pichia pastoris, Saccharomyces cerevisiae*, or *Schizosaccharomyces pombe*. Exemplary insect cells include any species of *Spodoptera* or *Drosophila*, including *Drosophila* S2 and *Spodoptera* SJ9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477; U.S. Pat. No. 5,750,870.

An expression cassette, vector, recombinant virus, plasmid, phage, phagemid, artificial chromosome or cloning vehicle of this invention can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, constructs of the invention are introduced into the cells for screening, thus, the nucleic acids enter the cells in a manner suitable for subsequent expression of the nucleic acid. The method of introduction is largely dictated by the targeted cell type. Exemplary methods include CaPO4 precipitation, liposome fusion, lipofection (e.g., LIPOFECTIN™), electroporation, viral infection, etc. The constructs of the invention may stably integrate into the genome of the host cell (for example, with retroviral introduction) or may exist either transiently or stably in the cytoplasm; for example, through the use of traditional plasmids, utilizing standard regulatory sequences, selection markers, etc.

Where appropriate, the engineered host cells of this invention can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired recombinant polypeptide.

Host cells containing the constructs of the invention can be cultured in conventional nutrient media modified as appropriate for activating promoters, selecting transformants or amplifying genes. The culture conditions, such as temperature, pH and the like, can be those previously used with the host cell selected for expression and will be apparent to the ordinarily skilled artisan.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., 1989, supra, or electroporation is generally used for prokaryotes or other cells that contain substantial cell-wall barriers. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., Methods in Enzymology, 185:527-537 (1990) and Mansour et al., Nature, 336:348-352 (1988).

Regulatory Nucleic Acid Sequences

In one embodiment, the invention provides osmo-responsive and osmo-regulatory nucleic acids comprising at least one regulatory nucleic acid, e.g., an inhibitory, stabilizing or an up-regulating nucleic acid molecule. In one embodiment, a sequence targeting a gene message, e.g., a lactogenic gene or lactogenic gene message, is used. In one embodiment that sequence is inhibitory, e.g., comprises a short interfering RNA (siRNA), a microRNA (miRNA), an antisense RNA and/or an RNA with ribozyme activity. Thus, in alternative embodiments, the invention provides for use of regulatory (inhibiting, stabilizing or an up-regulating) nucleic acids, including nucleic acids that can "target" a gene, message (mRNA) or protein to increase, enhance, decrease or abrogate expression and/or activity of the gene, message (mRNA) or protein.

In one embodiment, these regulatory (e.g., inhibitory) nucleic acids are oligonucleotides, e.g., containing known analogues of natural nucleotides, naturally occurring nucleic acids, synthetic nucleic acids, and/or recombinant nucleic acids. The invention encompasses use of nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. The invention provides for use of regulatory nucleic acids (inhibitory, stabilizing or upregulating) deoxyribonucleotide (DNA) or ribonucleotide (RNA) in either single- or double-stranded form. The invention provides for use of nucleic acids containing known analogues of natural nucleotides. The invention provides for use of regulatory (e.g., inhibitory) mixed oligonucleotides comprising an RNA portion bearing 2'-O-alkyl substituents conjugated to a DNA portion via a phosphodiester linkage, see, e.g., U.S. Pat. No. 5,013,830. The invention provides for use of nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). The invention provides for use of PNAs containing non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones used in nucleic acids of this invention include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The invention provides for use of regulatory (e.g., inhibitory) nucleic acids including genes, polynucleotides, DNA, RNA, cDNA, mRNA, oligonucleotide primers, probes and amplification products.

Nucleic acids of the invention may be introduced in eukaryotic (e.g., mammalian) cells for the purpose of expressing RNA transcripts that function to affect gene expression patterns yet are not translated into protein. Exemplary regulatory (e.g., inhibitory) nucleic acids used to practice this invention include short interfering RNAs (siRNAs) and microRNAs (miRNAs), antisense RNA and RNA with ribozyme activity: these can function to reduce or eliminate expression of native (endogenous) or introduced (heterologous) cell genes, e.g., mammalian genes.

Genes and nucleic acids used to practice this invention may be constructed or isolated, which when transcribed, produce regulatory (e.g., antisense or sense) RNA or double-stranded RNA that is complementary to all or part(s) of a targeted messenger RNA(s). The regulatory (e.g., antisense or sense) or double-stranded RNA or siRNA or miRNA reduces production of the polypeptide product of the messenger RNA. The polypeptide product may be any protein encoded by the mammalian cell's genome.

Genes and nucleic acids used to practice this invention also can be constructed or isolated, which when transcribed produce RNA enzymes, or ribozymes, which can act as endoribonucleases and catalyze the cleavage of RNA molecules with selected sequences.

The cleavage of selected messenger RNA's can result in the reduced production of their encoded polypeptide products. These regulatory (e.g., inhibitory) nucleic acids may be used to prepare novel mammalian cell lines; these mammalian cell lines can express reduced levels of polypeptides, including but not limited to the polypeptides cited herein that may be affected by antisense or interfering RNA.

Optimal lengths and concentrations of regulatory (e.g., inhibitory or upregulatory) nucleic acids used in any particular embodiment, e.g., in a bioreactor, an implant, in a cell culture, expressed as a recombinant protein, and the like, can be determined using routine methods and screening systems. Strategies for designing optimal lengths and concentrations are well described in the scientific and patent literature, and the skilled artisan can design regulatory (e.g., inhibitory or up-regulatory) nucleic acids, e.g., oligonucleotides, using the novel reagents of the invention using routine methods and screening systems.

Antisense Oligonucleotides

The invention provides antisense oligonucleotides comprising at least one sequence targeting a gene message, e.g., a sequence targeting a lactogenic gene or lactogenic gene message. Strategies for designing antisense oligonucleotides are well described in the scientific and patent literature, and the skilled artisan can design protein encoding (e.g., lactogenic protein-encoding) oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

In one embodiment, naturally occurring nucleic acids are used as regulatory (e.g., inhibitory or up-regulatory) nucleic acids oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense xylanase, mannanase and/or glucanase sequences of the invention (see, e.g., Gold (1995) J. of Biol. Chem. 270:13581-13584).

Regulatory Ribozymes

The invention provides ribozymes capable of a transcript (a message), e.g., that can bind to a lactogenic protein-encoding message. In one embodiment, these ribozymes can regulate (e.g., inhibit) protein activity, e.g., lactogenic protein activity, by e.g. targeting mRNA. Strategies for designing ribozymes and selecting the lactogenic protein specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

A ribozyme used to practice the invention can be an enzymatic ribozyme RNA molecule, which can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting.

RNA Interference (RNAi)

In one aspect, the invention provides RNA regulatory (e.g., inhibitory, stabilizing or up-regulating) molecules, e.g., an "RNAi" molecule, for targeting protein-coding sequences, such as lactogenic protein-coding sequences. The RNAi molecule can comprise a double-stranded RNA (dsRNA) molecule, e.g., siRNA, miRNA and/or short hairpin RNA (shRNA) molecules. The RNAi molecule, e.g., siRNA (small inhibitory RNA) can inhibit expression of a protein-coding gene (e.g., a lactogenic protein-coding gene), and/or miRNA (microRNA) to inhibit translation of a protein message (e.g., a lactogenic protein message). In one aspect, the RNAi molecule, e.g., siRNA and/or miRNA, is about 11, 12, 13, 14, 15, 16, 17, 18, 19, 20, 21, 22, 23, 24, 25, 26, 27, 28, 29 or more duplex nucleotides in length.

While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's molecules, e.g., siRNA and/or miRNA, of the invention. The process may be practiced in vitro, ex vivo or in vivo. In one aspect, the RNAi molecules of the invention can be used to generate a loss-of-function mutation in a cell, an organ or an animal.

Methods for making and using regulatory nucleic acids, e.g., RNAi molecules, siRNA and/or miRNA, for regulating RNA expression, e.g., for selectively degrading RNA, are well known in the art, see, e.g., U.S. Pat. Nos. 6,506,559; 6,511,824; 6,515,109; 6,489,127.

Transgenic Non-Human Animals

The invention provides transgenic non-human animals comprising an osmo-responsive transcriptional regulatory element (OR-TRE) of the invention, e.g., to study osmo-regulation in the non-human animal Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs, chickens, goats, fish and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats.

Cell Culturing, Implants and Bioreactors

In alternative embodiments, the compositions and methods of this invention can be used to sustain the health and viability of cell in any implant, artificial organ or culture system, e.g., in bioreactors, implants, artificial organs or simple cell culture plates, bottles, dishes, tubes or flasks. Compositions and methods are used to sustain the health and viability of cells in culture conditions, e.g., when those cells are designed to produce a product, for example, a recombinant protein or polysaccharide product, or a viral (e.g., virion particle) product in the case of a "producer cell line" (see e.g., U.S. Pat. Nos. 5,837,484; 6,566,118), or an organic molecule such as a polyketide, then because the cells are healthier and more viable because of incorporation of a composition of this invention (e.g., an expression cassette, vector, recombinant virus, plasmid, phage, phagemid, artificial chromosome or cloning vehicle of this invention, or any chimeric nucleic acid comprising an osmo-responsive transcriptional regulatory element (OR-TRE) of this invention), more of this desired product is made.

Compositions and methods as provided herein also can be used to boost production of molecules, e.g., recombinant proteins, by cells in a culture system, e.g., a bioreactor, an implant and the like. In one aspect, compositions and methods as provided herein are used to maintain or increase the production of properly folded or preferably folded (e.g., a wild type folding) and/or glycosylated protein under conditions of less than optimal osmotic conditions (less than optimal osmotic conditions for a particular cell or culture system), e.g., under conditions of hyperosmolality and/or hypo-osmolality, such as those seen in late stage or dense cell culture conditions. Thus, in one embodiment, the compositions and methods as provided herein are used to maintain or increase the quality of product (e.g., recombinant proteins) produced in a cell, e.g., a cell culture system, particularly osmotically stressed conditions such as seen in late stage or dense cell culture conditions.

Compositions and methods as provided herein can be practiced with any culture system known in the art, see e.g., U.S. Pat. Nos. 5,705,364; 5,721,121; 5,976,833; 6,180,401; 6,410,270; 6,716,602; 7,294,484; 7,294,481; and U.S. Pat. App. Pub. Nos. 20030096414; 20050272124 (describing fed batch cell cultures); 20060160180; 20070254358; 20070231901 (describing a microfluidic cell culture system); 20070184529 (describing manipulating the cell culture environment for glycosylation); 20070161106.

For example, in one embodiment a "fed batch cell culture" is used, e.g., a batch culture where cells and culture medium are supplied to a culturing vessel initially and additional culture nutrients are fed, continuously or in discrete increments, to the culture during culturing, with or without periodic cell and/or product harvest before termination of culture. Fed batch culture systems used to practice this invention can be "semicontinuous fed batch cultures," e.g., where periodically whole cultures including cells and medium are removed and replaced by fresh medium. Simple "batch culture," e.g., where all components for cell culturing including cells and all culture nutrients are supplied to a culturing vessel at the start of the culturing process, also can be used to practice this invention. Perfusion culturing also can be used to practice this invention, e.g., where a supernate is not removed from the culturing vessel during a manufacturing culture growth process; cells can be restrained in the culture by, e.g., filtration, encapsulation, anchoring to microcarriers etc and the culture medium is continuously or intermittently introduced and removed from the culturing vessel.

The cells of this invention (including any cell comprising an expression cassette, vector, recombinant virus, plasmid, phage, phagemid, artificial chromosome or cloning vehicle of this invention, or any chimeric nucleic acid comprising an osmo-responsive transcriptional regulatory element (OR-TRE) of this invention) can be used in any cell culture system, including any bioreactor, cell culture plate, tubes or flask. The invention also provides bioreactor systems, cell culture systems, plates, tubes and flasks comprising cells of this invention.

For example, in practicing this invention, a cell growth phase can be followed by a polypeptide production phase, which is distinct therefrom. In one embodiment, a production phase is carried out in a different culturing vessel from the cell growth phase.

Alternatively, the same vessel can be employed for each step. For example, the culture medium of the growth phase can be supplied with high-osmolality, low-glucose containing medium for production. Alternatively, medium-exchange using cell-fluid separation devices available in the art (e.g., cross-flow filtration, rotating screens or fluidized bed microcarriers) can be used to enable the same vessel to be used.

In one embodiment, the production phase involves inoculating the cultured animal cells of the growth phase at a cell seed density of at least about $1.0 \times 10^6$ cells/mL, or at least about $3.0 \times 10^6$ cells/mL, or between about 1 and $10 \times 10^6$ cells/mL. In one embodiment, animal cells are cultured at a starting osmolality of about 400 to 600 mOsm, or between about 400 to 500 mOsm, in a culturing vessel, e.g., such as that exemplified for the growth phase.

In one embodiment, to achieve a culture medium having the osmolality specified, a PS-04™, DIESEL™ or SUPER CELL™ culture media, or similar media, can be used, and the osmolality of the culture medium can be increased via the addition of the basal concentration of glucose and a salt (such as NaCl, for example). This type of culture medium contains an excess of amino acids in order to provide additional cell nutrients and achieve a high starting osmolality. However, as will be readily apparent to the ordinarily skilled practitioner, the concentration(s) of other constituents in the culture medium can be adjusted in order to reach the desired osmolality.

In one embodiment, the osmolality is maintained at substantially the desirable range throughout the culturing. Controlling the supply of glucose to the cell culture medium helps to prevent excessive increases in osmolality substantially above the desirable optimum.

In one embodiment, the production phase is carried out in the presence of a concentration of glucose controlled throughout the culturing to be within a range between about 0.01 and 1 g/L, preferably 0.02-0.5 g/L, and more preferably 0.05-0.2 g/L. In order to monitor and control the glucose concentration of the culture medium in the range specified, FIA or other automated on-line control systems are useful.

In one embodiment, the glutamine concentration is also controlled throughout the culturing to be in a range of 0.2 to 2 mM, more preferably 0.5 to 1 mM. Control of the glutamine concentration can be achieved using a FIA system similar to that discussed above, for example.

In one embodiment, culture conditions, such as temperature, pH, $dO_2$ and the like, are those previously used with the host cell selected for protein production, and will be apparent to the ordinarily skilled artisan. For example, the pH may be adjusted to a range between 6.5 and 7.5 and the temperature for production may be between 30° C. and 38° C.

In one embodiment, the production cycle can be reduced from the normal time of about 10 to 15 days or more for recombinant proteins to about 9 days or less, or 7 days or less. In certain embodiments (e.g., where the polypeptide of interest is DNase) the production phase is terminated before the maximum polypeptide titer is obtained. This is advantageous as the resultant DNase composition has a reduced percentage deamidation compared to DNase produced in longer runs. Following the polypeptide production phase, the polypeptide of interest can be recovered from the culture medium using techniques which are well established in the art.

Bioreactors, Implants and Artificial Organs

The invention also provides implants and artificial organs, bioreactor systems, cell culture systems, plates, dishes, tubes, bottles and flasks comprising cells of this invention. Any implant, artificial organ, bioreactor systems, cell culture system, cell culture plate, dish (e.g., petri dish), cell culture tube and/or cell culture flask (e.g., a roller bottle) can be used to practice this invention.

For example, a bioreactor of the invention, or a bioreactor used to practice the methods of this invention, can be an implantable bioreactor device as described e.g., in U.S. Pat. App. Pub. No. 20080112995; or a bioreactor device as described e.g., in U.S. Pat. App. Pub. Nos. 20080057571; 20080044890; 20080044850; 20080038816; 20080032396; 20080032389; 20080032380; 20080014629; 20080014215; and/or 20080003669, and/or in U.S. Pat. Nos. 7,378,023; 7,371,567, describing bioreactors for bioartificial organs; U.S. Pat. No. 7,351,584; describing bioreactors for mammalian hepatocytes; U.S. Pat. No. 7,348,175, describing a microprocessor controlled and instrumented bioreactor; U.S. Pat. No. 7,300,584, describing a device for biological treatment of a suspension in a bioreactor; U.S. Pat. No. 7,290,669, describing an upflow bioreactor; U.S. Pat. No. 7,264,962, describing a three stage enzymatic reactor; U.S. Pat. No. 7,229,808, describing a bioreactor using viable immobilized biological material; U.S. Pat. No. 7,198,941, describing a porous vessel bioreactor apparatus; U.S. Pat. No. 7,198,940, describing a bioreactor apparatus and cell culturing system for automated cultivation and processing of living cells; U.S. Pat. No. 7,156,985, describing a bioreactor system having improved temperature control; to describe just a few exemplary bioreactors and cell culture systems that can be used to practice this invention.

In alternative embodiments, the invention provides implants, e.g., medical implants (e.g., cells secreting insulin or a cytokine or hormone), or stents, orthopedic, ocular or dental implants comprising a cell of the invention. For example, implants and artificial organs (e.g., artificial or implant skin, liver, pancreas or teeth), bioreactor systems, cell culture systems, plates, dishes, tubes and flasks can comprise stem cells, pluripotent cells, undifferentiated cells, choroid plexus cells, Schwann cells, retinal cells, nerve cells, bone cells, liver cells, liver parenchymal cells, endothelial cells, adipocytes, fibroblastic cells, Kupffer cells, kidney cells, blood vessel cells, skin cells, periodontal cells, odontoblasts, dentinoblasts, cementoblasts, enameloblasts, odontogenic ectomesenchymal tissue, osteoblasts, osteoclasts, fibroblasts, and other cells and tissues involved in odontogenesis or bone formation and/or stem cells, and other human or animal organ cells, or the cells are embryonic or adult stem cells, or a combination thereof.

Any bioreactor, implant, stent, artificial organ or similar device comprising a cell of the invention can be used to make or use the compositions or methods of this invention; for example, implants as described in U.S. Pat. Nos. 7,388,042; 7,381,418; 7,379,765; 7,361,332; 7,351,423; 6,886,568; 5,965,125; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

Osmo-Responsive Transcriptional Enhancers and their Binding Proteins

The invention provides at least one osmo-responsive transcriptional regulatory element (OR-TRE) comprising at least one TonEBP-responsive or NFATc-responsive transcriptional enhancer sequence operatively linked to a transcriptional regulatory sequence, e.g., operatively linked to promoter, such as a minimal promoter, constitutive promoter or inducible promoter, and the like. TonEBP-responsive and NFATc responsive transcriptional enhancer sequences, and the TonEBP and NFATc proteins that bind them, are well known in the art.

For example, a TonEBP-responsive transcriptional enhancer sequence can comprise the sequence: 5'-(T/A/C) GGAA(A/T)NN(T/A/C)N(T/A/C)-3' (SEQ ID NO:1); and TonEBP-responsive transcriptional enhancer sequences are described e.g., see Daoudal (1997) J. Biol. Chem. 272(5): 2615-2619; Ferraris (1999) Am. J. Physiol. 276(3 Pt 1), and others described below. Exemplary active TonEBP binding sites that can be used to practice this invention include those found in Table 1:

TABLE 1

| Origin | Sequence | Reference | SEQ ID NO: |
|---|---|---|---|
| Canine BGT1 | 5' TGGAAAAGTCC 3' | 10 | 11 |
| Human Aldose Reductase A | 5' TGGAAAAATAT 3' | 5 | 12 |
| Human Aldose Reductase B | 5' TGGAAAAATTT 3' | 5 | 13 |
| Human Aldose Reductase C | 5' TGGAAAATCAC 3' | 5 | 14 |
| Rabbit Aldose Reductase | 5' CGGAAAATCAC 3' | 3 | 15 |
| Mouse and rat Aldose Reductase | 5' TGGAAAATCAC 3' | 1 | 16 |
| Human TonEBP binding sites | 5' TGGAAAATTAC 3' | 8 | 17 |
| Human TonEBP binding sites modified 6 | 5' TGGAATATTAC 3' | 8 | 18 |
| Human TonEBP binding sites modified 7 | 5' TGGAAATTTAC 3' | 8 | 19 |

TABLE 1-continued

| Origin | Sequence | Reference | SEQ ID NO: |
|---|---|---|---|
| Rabbit TonEBP binding sites modified 1 | 5' AGGAAAATCAC 3' | 2 | 20 |
| Rabbit TonEBP binding sites modified 2 | 5' CGGAAAAAACC 3' | 2 | 21 |
| Rabbit TonEBP binding sites modified 3 | 5' C GGAAAATAC C 3' | 2 | 22 |
| Rabbit TonEBP binding sites modified 4 | 5' CGGAAAATCCC 3' | 2 | 23 |
| Human Sodium/myo-Inositol TonEA | 5' TGGAAAACTAC 3' | 9 | 24 |
| Human Sodium/myo-Inositol TonEB1 | 5' ATAGAATTCCA 3' (antisense: 5' TGGAATTCTAT 3') | 9 | 25 (26 antisense) |
| Human Sodium/myo-Inositol TonEB2/3 | 5' TGGAAAATTCCA 3' | 9 | 27 |
| Human Sodium/myo-Inositol TonEC1 | 5' TGGAAAATTAC 3' | 9 | 28 |
| Human Sodium/myo-Inositol TonEC2 | 5' TGGAAAGTTAC 3' | 9 | 29 |
| Human Sodium/myo-Inositol TonEp | 5' TGGAAAGTTCC 3' | 9 | 30 |
| Mouse HSP70 TonEA | 5' TGGAAAGTTTT 3' | 11 | 31 |
| Mouse HSP70 TonEB | 5' TGGAAAATTTT 3' | 11 | 32 |
| Mouse HSP70 TonEC | 5' TGGAAATCTCC 3' | 11 | 33 |
| Mouse HSP70 TonED | 5' TGGAAAAACAC 3' | 11 | 34 |
| Mouse Urea Transporter-A gene | 5' GGAGTTTTCCA 3' (antisense: 5' TGGAAAACTCC 3') | 4 | 35 (36 antisense) |

1. Daoudal S, Tournaire C, Halere A, Veyssière G, Jean C. Isolation of the mouse aldose reductase promoter and identification of a tonicity-responsive element. J. Biol Chem. 1997 Jan 31;272(5):2615-9.
2. Ferraris JD, Williams CK, Ohtaka A, Garcia-Pérez A. Functional consensus for mammalian osmotic response elements. Am J Physiol. 1999 Mar;276(3 Pt 1).
3. Ferraris JD, Williams CK, Jung KY, Bedford JJ, Burg MB, Garcia-Pérez A. ORE, a eukaryotic minimal essential osmotic response element. The aldose reductase gene in hyperosmotic stress. J Biol Chem. 1996 Aug 2;271(31):18318-21.
4. Fenton RA, Cottingham CA, Stewart GS, Howorth A, Hewitt JA, Smith CP. Structure and characterization of the mouse UT-A gene (Slc14a2). Am J Physiol. Renal Physiol. 2002 Apr; 282(4):F630.
5. Ko BC, Ruepp B, Bohren KM, Gabbay KH, Chung SS. Identification and characterization of multiple osmotic response sequences in the human aldose reductase gene. J Biol Chem. 1997 Jun 27;272(26):16431-7.
6. Lopez-Rodriguez C, Aramburu J, Rakeman AS, Rao A: NFAT5, a constitutively nuclear NFAT protein that does not cooperate with Fos and Jun. Proc Natl Acad Sci USA 1999, 96:7214-7219.
7. Lopez-Rodriguez C, Aramburu J, Jin L, Rakeman AS, Michino M, Rao A: Bridging the NFAT and NF-kappaB families: NFAT5 dimerization regulates cytokine gene transcription in response to osmotic stress. Immunity 2001, 15:47-58.
8. Miyakawa H, Woo SK, Chen CP, Dahl SC, Handler JS, Kwon HM. Cis- and trans-acting factors regulating transcription of the BGT1 gene in response to hypertonicity. Am J Physiol. 1998 Apr;27 4(4 Pt 2):F753-61.
9. Rim JS, Atta MG, Dahl SC, Berry GT, Handler JS, Kwon HM. Transcription of the sodium/myo-inositol cotransporter gene is regulated by multiple responsive enhancers spread over 50 kilobase pairs in the 5'-flanking region. J. Biol Chem. 1998 Aug 7;273(32):20615-21.
10. Stroud JC, Lopez-Rodriguez C, Rao A, Chen L: Structure of a TonEBP-DNA complex reveals DNA encircled by a transcription factor. Nat Struct Biol 2002, 9:90-94.
11. Woo SK, Lee SD, Na KY, Park WK, Kwon HM. TonEBP/NFAT5 stimulates transcription of HSP70 in response to hypertonicity. Mol Cell Biol. 2002 Aug;22(16):5753-60.

Boosting the Osmo-Protective Phenotype

In one aspect, the compositions and/or methods of the invention also express the proteins that bind to the osmo-responsive transcriptional enhancers, e.g., compositions (constructs) of the invention comprise nucleic acid sequence encoding at least one protein that binds to an osmo-responsive transcriptional enhancer used in a construct of this invention. This alternative embodiment is particular useful in aspects of the invention where the constructs and/or methods of the invention are used as inducible nucleic acid and/or polypeptide expression systems; where the constructs of the invention themselves can supply (manufacture), either constitutively or inducibly (e.g., osmo-responsively), additional or new proteins that bind to the osmo-responsive transcriptional enhancers to "boost" transcription activation of the osmo-responsive transcriptional enhancer sequences present in a construct of this invention.

In another embodiment, the additional or new proteins that bind to the osmoresponsive transcriptional enhancers to "boost" transcription activation of the osmoresponsive transcriptional enhancer sequences are present on separate constructs other than an osmo-responsive transcriptional regulatory element (OR-TRE) of this invention.

For example, an exemplary method of the invention comprises use of both an OR TRE comprising construct of this invention and another expression construct (e.g., an expression vector) for generating new or additional osmo-responsive transcriptional enhancer-binding sequences.

For example, a construct of this invention can encode a tonicity-responsive enhancer-binding protein, or "TonE-binding protein," or "TonEBP" having the sequence (SEQ ID NO: 37):

```
  1 MPSDFISLLS ADLDLESPKS LYSRESVYDL LPKELQLPPS RETSVASMSQ TSGGEAGSPP
 61 PAVVAADASS APSSSSMGGA CSSFTTSSSP TIYSTSVTDS KAMQVESCSS AVGVSNRGVS
121 EKQLTSNTVQ QHPSTPKRHT VLYISPPPED LLDNSRMSCQ DEGCGLESEQ SCSMWMEDSP
181 SNFSNMSTSS YNDNTEVPRK SRKRNPKQRP GVKRRDCEES NMDIFDADSA KAPHYVLSQL
241 TTDNKGNSKA GNGTLENQKG TGVKKSPMLC GQYPVKSEGK ELKIVVQPET QHRARYLTEG
301 SRGSVKDRTQ QGFPTVKLEG HNEPVVLQVF VGNDSGRVKP HGFYQACRVT GRNTTPCKEV
361 DIEGTTVIEV GLDPSNNMTL AVDCVGILKL RNADVEARIG IAGSKKKSTR ARLVFRVNIM
421 RKDGSTLTLQ TPSSPILCTQ PAGVPEILKK SLHSCSVKGE EEVFLIGKNF LKGTKVIFQE
481 NVSDENSWKS EAEIDMELFH QNHLIVKVPP YHDQHITLPV SVGIYVVTNA GRSHDVQPFT
541 YTPDPAAAGA LNVNVKKEIS SPARPCSFEE AMKAMKTTGC NLDKVNIIPN ALMTPLIPSS
601 MIKSEDVTPM EVTAEKRSST IFKTTKSVGS TQQTLENISN IAGNGSFSSP SSSHLPSENE
661 KQQQIQPKAY NPETLTTIQT QDISQPGTFP AVSASSQLPN SDALLQQATQ FQTRETQSRE
721 ILQSDGTVVN LSQLTEASQQ QQQSPLQEQA QTLQQQISSN IFPSPNSVSQ LQNTIQQLQA
781 GSFTGSTASG SSGSVDLVQQ VLEAQQQLSS VLFSAPDGNE NVQEQLSADI FQQVSQIQSG
841 VSPGMFSSTE PTVHTRPDNL LPGRAESVHP QSENTLSNQQ QQQQQQQQVM ESSAAMVMEM
901 QQSICQAAAQ IQSELFPSTA SANGNLQQSP VYQQTSHMMS ALSTNEDMQM QCELFSSPPA
961 VSGNETSTTT TQQVATPGTT MFQTSSSGDG EETGTQAKQI QNSVFQTMVQ MQHSGDNQPQ
1021 VNLFSSTKSM MSVQNSGTQQ QGNGLFQQGN EMMSLQSGNF LQQSSHSQAQ LFHPQNPIAD
1081 AQNLSQETQG SLFHSPNPIV HSQTSTTSSE QMQPPMFHSQ STIAVLQGSS VPQDQQSTNI
1141 FLSQSPMNNL QTNTVAQEAF FAAPNSISPL QSTSNSEQQA AFQQQAPISH IQTPMLSQEQ
1201 AQPPQQGLFQ PQVALGSLPP NPMPQSQQGT MFQSQHSIVA MQSNSPSQEQ QQQQQQQQQ
1261 QQQQQQSILF SNQNTMATMA SPKQPPPNMI FNPNQNPMAN QEQQNQSIFH QQSNMAPMNQ
1321 EQQPMQFQSQ STVSSLQNPG PTQSESSQTP LFHSSPQIQL VQGSPSSQEQ QVTLFLSPAS
1381 MSALQTSINQ QDMQQSPLYS PQNNMPGIQG ATSSPQPQAT LFHNTAGGTM NQLQNSPGSS
1441 QQTSGMFLFG IQNNCSQLLT SGPATLPDQL MAISQPGQPQ NEGQPPVTTL LSQQMPENSP
1501 LASSINTNQN IEKIDLLVSL QNQGNNLTGS F
```

NFATc tonicity-responsive transcriptional activating sequence also can be used in constructs of the invention; the NFATc signaling pathway is described e.g., in Li (2007) Am. J. Physiol. Cell. Physiol. 292(5):C1606-16. Sequence responsive to the tonicity-responsive enhancer binding protein described, e.g., by Miyakawa (1999) "Tonicity-responsive enhancer binding protein, arel-like protein that stimulates transcription in response to hypertonicity" Proc. Natl. Acad. Sci. USA 96(5):2538-2542 (see also, e.g., Lopez-Rodriguez (1999) Proc. Natl. Acad. Sci. USA 96(13):7214-7219), also can be used to practice this invention. This protein regulates gene expression induced by osmotic stress in mammalian cells. Unlike monomeric members of this protein family, this protein exists as a homodimer and forms stable dimers with DNA elements. Multiple transcript variants encoding different isoforms have been found for this gene.

One isoform that can be used to practice this invention is (SEQ ID NO: 40):

```
  1 MPSDFISLLS ADLDLESPKS LYSRDSLKLH PSQNFHRAGL LEESVYDLLP KELQLPPSRE
 61 TSVASMSQTS GGEAGSPPPA VVAADASSAP SSSSMGGACS SFTTSSSPTI YSTSVTDSKA
121 MQVESCSSAV GVSNRGVSEK QLTSNTVQQH PSTPKRHTVL YISPPPEDLL DNSRMSCQDE
181 GCGLESEQSC SMWMEDSPSN FSNMSTSSYN DNTEVPRKSR KRNPKQRPGV KRRDCEESNM
241 DIFDADSAKA PHYVLSQLTT DNKGNSKAGN GTLENQKGTG VKKSPMLCGQ YPVKSEGKEL
301 KIVVQPETQH RARYLTEGSR GSVKDRTQQG FPTVKLEGHN EPVVLQVFVG NDSGRVKPHG
361 FYQACRVTGR NTTPCKEVDI EGTTVIEVGL DPSNNMTLAV DCVGILKLRN ADVEARIGIA
```

```
 421  GSKKKSTRAR  LVFRVNIMRK  DGSTLTLQTP  SSPILCTQPA  GVPEILKKSL  HSCSVKGEEE

481  VFLIGKNFLK  GTKVIFQENV  SDENSWKSEA  EIDMELFHQN  HLIVKVPPYH  DQHITLPVSV

541  GIYVVTNAGR  SHDVQPFTYT  PDPAAGALNV  NVKKEISSPA  RPCSFEEAMK  AMKTTGCNLD

601  KVNIIPNALM  TPLIPSSMIK  SEDVTPMEVT  AEKRSSTIFK  TTKSVGSTQQ  TLENISNIAG

661  NGSFSSPSSS  HLPSENEKQQ  QIQPKAYNPE  TLTTIQTQDI  SQPGTFPAVS  ASSQLPNSDA

721  LLQQATQFQT  RETQSREILQ  SDGTVVNLSQ  LTEASQQQQQ  SPLQEQAQTL  QQQISSNIFP

781  SPNSVSQLQN  TIQQLQAGSF  TGSTASGSSG  SVDLVQQVLE  AQQQLSSVLF  SAPDGNENVQ

841  EQLSADIFQQ  VSQIQSGVSP  GMFSSTEPTV  HTRPDNLLPG  RAESVHPQSE  NTLSNQQQQQ

901  QQQQQVMESS  AAMVMEMQQS  ICQAAAQIQS  ELFPSTASAN  GNLQQSPVYQ  QTSHMMSALS

961  TNEDMQMQCE  LFSSPPAVSG  NETSTTTTQQ  VATPGTTMFQ  TSSSGDGEET  GTQAKQIQNS

1021  VFQTMVQMQH  SGDNQPQVNL  FSSTKSMMSV  QNSGTQQQGN  GLFQQGNEMM  SLQSGNFLQQ

1081  SSHSQAQLFH  PQNPIADAQN  LSQETQGSLF  HSPNPIVHSQ  TSTTSSEQMQ  PPMFHSQSTI

1141  AVLQGSSVPQ  DQQSTNIFLS  QSPMNNLQTN  TVAQEAFFAA  PNSISPLQST  SNSEQQAAFQ

1201  QQAPISHIQT  PMLSQEQAQP  PQQGLFQPQV  ALGSLPPNPM  PQSQQGTMFQ  SQHSIVAMQS

1261  NSPSQEQQQQ  QQQQQQQQQQ  QQQSILFSNQ  NTMATMASPK  QPPPNMIFNP  NQNPMANQEQ

1321  QNQSIFHQQS  NMAPMNQEQQ  PMQFQSQSTV  SSLQNPGPTQ  SESSQTPLFH  SSPQIQLVQG

1381  SPSSQEQQVT  LFLSPASMSA  LQTSINQQDM  QQSPLYSPQN  NMPGIQGATS  SPQPQATLFH

1441  NTAGGTMNQL  QNSPGSSQQT  SGMFLFGIQN  NCSQLLTSGP  ATLPDQLMAI  SQPGQPQNEG

1501  QPPVTTLLSQ  QMPENSPLAS  SINTNQNIEK  IDLLVSLQNQ  GNNLTGSF
```

See, e.g., Nagase (1998) *DNA Res.* 5(6):355-364; Lopez-Rodriguez (1999) *Proc. Natl. Acad. Sci. USA* 96(13):7214-7219; Miyakawa (1999) *Proc. Natl. Acad. Sci. USA* 96(5): 2538-2542.

As described above, the invention provides nucleic acid constructs that, when inserted and expressed in a cell (including cells in a bioreactor, cell culture, implants, and the like) provide an osmo-protective phenotype to that cell. In alternative embodiments, the invention provides osmo-protective constructs with enhanced capacity, e.g., by also encoding an NFATc polypeptide, an AP-1 polypeptide, a TonEBP polypeptide, a calcineurin polypeptide, or a combination thereof. An augmented osmo-protective capacity is gained when a construct of the invention also expresses an NFATc polypeptide because, e.g., NFATc polypeptides bind to tonicity responsive enhancers, resulting in more (greater, higher) expression of osmo-protective proteins in the cell. An augmented osmo-protective capacity is gained when a construct of the invention also expresses an AP-1 polypeptide because, e.g., AP-1 polypeptides can be a necessary cofactor for NFATc polypeptide binding to tonicity responsive enhancers. An augmented osmo-protective capacity is gained when a construct of the invention also expresses a TonEBP polypeptide because, e.g., TonEBP proteins bind to the TonEBP-responsive transcriptional enhancer sequences of this invention. The NFATc, AP-1, TonEBP and/or calcineurin polypeptide encoding nucleic acids can also be regulated by an osmoresponsive transcriptional regulatory element (OR-TRE) of this invention, or by another enhancer or promoter.

In an alternative embodiment, rather than being expressed on the same construct as an ORE-TRE osmo-responsive nucleic acid molecule of the invention, the NFATc, AP-1, TonEBP and/or calcineurin polypeptides are expressed on separate constructs, e.g., separate vectors, which can be episomal, transient expression constructs, or genomically integrated expression constructs.

Kits and Libraries

The invention provides kits comprising compositions and methods of the invention, including cells of the invention, target sequences, transfecting agents, transducing agents, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLES

Example 1: Design of Osmo-Sensitive Hybrid Transcriptional Regulatory Elements the Invention Provides Osmo-Responsive Transcriptional Regulatory Elements (ORTREs)

This example describes the use of a TonE binding site to design an exemplary osmo-responsive synthetic hybrid transcriptional regulatory element of this invention, and its expression characteristics at increasing osmolalities. These results demonstrate that osmo-responsive transcriptional regulatory elements of this invention can be transactivated in an osmo-dependent manner.

Methods:

Construction of the Osmo-Responsive Promoter POR1

The osmo-responsive promoter POR1 was cloned by PCR amplification of the human CMV promoter with oligos OLM155 5'-TTGACTAGTTGGAAAATCACCA-GAATGGGATTTAGAGAGGTGGGGTTCCTGA CTCAT- TGCTAGCTCGAGCTCGGTACCCGGGTCGAGTAG-GCGTGTACGGTGGGAG-3' (SEQ ID NO:8) and the annealing sequence OLM165 5'-GGTGGTTTAATCGATA-GAACC-3' (SEQ ID NO:10) where TonE and AP1 binding sites are in bold, these binding sites as well as the sequence in between them are taken as the osmotic response element (OR), the annealing sequence is in italic; a SpeI and an NheI cloning site are introduced respectively 5' and 3' of the osmotic response element (OR), and the cloning sites are underlined. The PCR product was topo cloned thus resulting in pLM216. The hybrid promoter with its directly 3' intron was excised from pLM216 with (SpeI/ClaI) and cloned into the STIgMA-FC Stalkless expression plasmid (SpeI ClaI) thus resulting in pOsmo1 (POR1-Intron-STIgMA-Fc-pA; POR1, OR-Pfragment CMV).

Cell Culture, Transfection

Chinese hamster ovary cells CHO-K1 DUX-B11 (dhfr-) were grown in suspension in a serum-free low protein (recombinant human insulin) medium. Optimized LIPO-FECTAMINE™ (Invitrogen, Carlsbad, Calif.) transfection protocols were used for high efficiency transient transfection of the cells. Transiently transfected cells were harvested six (6) hours post transfection, and seeded in six (6) well plates in serum containing medium at increasing osmolality. The osmolality of the medium was adjusted in each well by adding a fix volume of a phosphate buffer saline with increasing salt concentration. Transiently transfected cells were routinely analyzed after 48 hours for an Fc fusion gene expression by ELISA.

Results

In order to analyze the potential of the osmo-responsive element for design of a mammalian gene regulation system for biopharmaceutical production and stress responsive genetic-engineering, we fused the osmo-responsive element of the mouse aldose reductase promoter (sequences –1053 to –1007) which contains a TonE site and an AP-1 site (Activating Protein-1) (see, e.g., Daoudal et al 1997, supra) 5' of a portion of the human cytomegalovirus immediate early promoter thus constructing the osmoresponsive promoter 1 POR1.

We constructed a plasmid in which the exemplary POR1 promoter drives the expression of an Fc fusion protein pOsmo1 (POR1-Intron-STIgMA-Fc-pA; POR1, OR Pfragment CMV). Following transfection of either a constitutive promoter—(the human cytomegalovirus promoter) or the POR1-driven Fc fusion expression plasmids into CHOK1 DUX-B11 (dhfr-) cells, the transfected cells were seeded and grown for 48 hours (h) in media of increasing osmolalities. The cells' supernatants were then assayed for Fc fusion expression, as schematically illustrated in FIG. 2, where osmolalities are expressed as mOsm, and protein concentration from both the constitutive promoter and the POR1-transcriptional regulatory element of the invention in mg/L.

The expression levels of the constitutive promoter-driven expression plasmid remained stable from 300 to 400 mOsm and then decreased as osmolality further increased. This probably reflects well-described cell behaviors at high osmolality: decreasing cell growth rates and decreasing cells viability with increasing osmolality.

Hence constitutive expression of the reporter gene accounts for the effects of high osmolalities on recombinant protein expression.

The human cytomegalovirus promoter and the osmo-responsive promoter 1 drove equivalent recombinant protein expression levels at 300 mOsm. As the osmolality was increased up to 400 mOsm, POR1-driven expression levels increased and then decreased with increasing osmolality. However, the POR1-driven expression levels decreased at a much slower rate than their constitutive promoter-driven counter part.

Conclusion

Comparison of the constitutive-driven and exemplary POR1-driven Fc fusion expression levels indicates that even though the cells' physiology is affected at high osmolalities and thus overall protein production decreases, the exemplary POR1 of the invention drives higher protein expression levels than the CMV promoter in hyperosmotic medium. These results demonstrate that osmo-responsive transcriptional regulatory elements of this invention can be trans-activated in an osmo-dependent manner when transfected into CHO-K1 DUX-B11 (dhfr–) cells. Thus, these results demonstrate that the invention's transcriptional regulatory elements, as exemplified by this POR1-driven transgene expression, can be used a real-time osmolality sensor.

Figure 3:
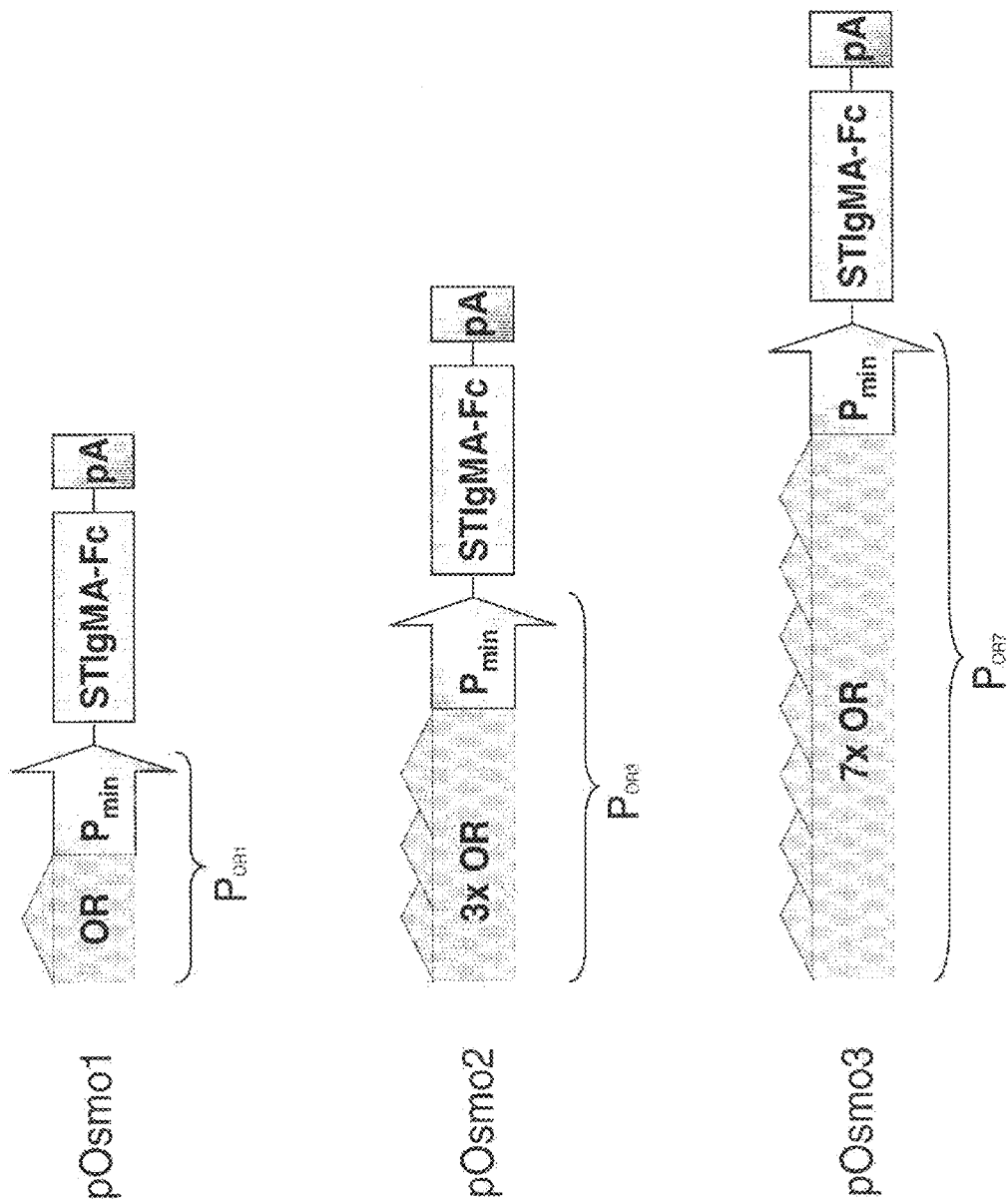
FIG. 3 schematically illustrates exemplary osmo-responsive transcriptional regulatory elements (OR-TREs) of this invention, as described in detail in Example 1, below.

Example 2: Design of a Set of Osmo-Responsive Transcriptional Regulatory Elements This example describes the design and testing of a set of osmo-responsive transcriptional regulatory elements of this invention. We tested the impact of increasing the number of osmo-responsive elements in a construct of this invention on the recombinant protein expression window at increasing osmolalities. FIG. 3 schematically illustrates how three exemplary synthetic osmo-responsive transcriptional regulatory elements of this invention were constructed.

Methods:

Construction of the Osmo-Responsive Promoters

POR1 was excised from pOsmo1 (SpeI/ClaI) and cloned into pOsmo1 (NheI/ClaI) thus resulting in an osmo-responsive hybrid promoter containing 2 osmotic response elements: pLM217 (POR2-Intron). Likewise POR3 was constructed by excision of POR2-Intron from pLM217 (SpeI/ClaI) and insertion into pOsmo1 (NheI/ClaI) thus resulting in pOsmo2 (POR3-Intron-STIgMA-Fc-pA; POR3, OR-OR-OR-Pfragment CMV). POR2-Intron was excised from pLM217 (SpeI/ClaI) and cloned into pLM217 (NheI/ClaI) thus resulting in pLM218: POR4-Intron (POR4, OR-OR-OR-OR-Pfragment CMV). POR4-Intron was excised from pLM218 (SpeI/ClaI) and ligated into pOsmo2 (NheI/ClaI) thus resulting into pOsmo3 (POR7-Intron-STIgMA-Fc-pA; POR7, OR-OR-OR-OR-OR-OR-OR Pfragment CMV).

Cell Culture, Transfection

Chinese hamster ovary cells CHO-K1 DUX-B11 (dhfr-) were grown in suspension in a serum-free low protein (recombinant human insulin) medium. Optimized LIPO-FECTAMINE™ (Invitrogen, Carlsbad, Calif.) transfection protocols were used for high efficiency transient transfection of the cells. Transiently transfected cells were harvested 6 hours post transfection, and seeded in 6 well plates in serum containing medium at increasing osmolality. The osmolality of the medium was adjusted in each well by adding a fix volume of a phosphate buffer saline with increasing salt concentration. Transiently transfected cells were routinely analyzed after 48 hours for an Fc fusion gene expression by ELISA.

Results

In order to assess the impact of an increasing number of osmo-responsive elements 5' of the human cytomegalovirus promoter fragment, we constructed two further osmo-responsive promoters bearing either 3 or 7 osmo-responsive elements cloned side by side: POR3 and POR7, as illustrated in FIG. 3. CHO-K1 DUX-B11 (dhfr-) cells were transfected with an Fc fusion expression plasmid driven either by the human cytomegalovirus constitutive promoter or the osmo responsive promoter 3, POR3 or the osmo-responsive promoter 7, POR7. Six (6) hours post-transfection, the cells were harvested and seeded in medium of increasing osmolality. Constitutive expression of the reporter gene was not significantly impacted by osmolality between 300 mOsm and 400 mOsm, Fc fusion expression level then decreased as osmolality increased, as illustrated in FIG. 4, which schematically illustrates the in vivo osmo-protective efficacy of the exemplary osmo-responsive transcriptional regulatory elements (OR-TREs) of this invention illustrated in FIG. 3; see also the normalized data in FIG. 5.

Figure 4:
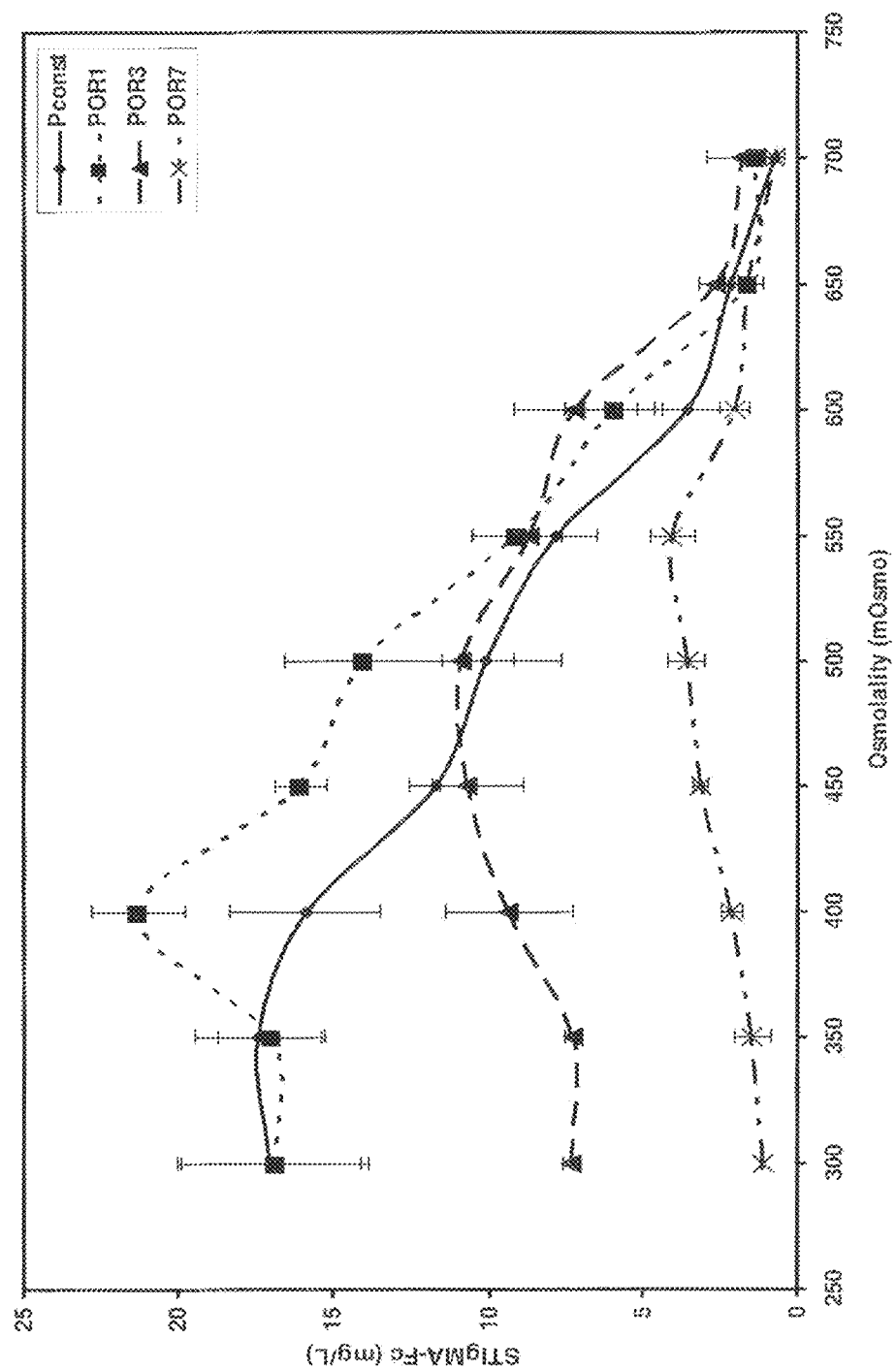
FIG. 4 schematically illustrates the in vivo osmo-protective efficacy of the exemplary osmo-responsive transcriptional regulatory elements (OR-TREs) of this invention illustrated in FIG. 3, as described in detail in Example 1, below.
Figure 5:
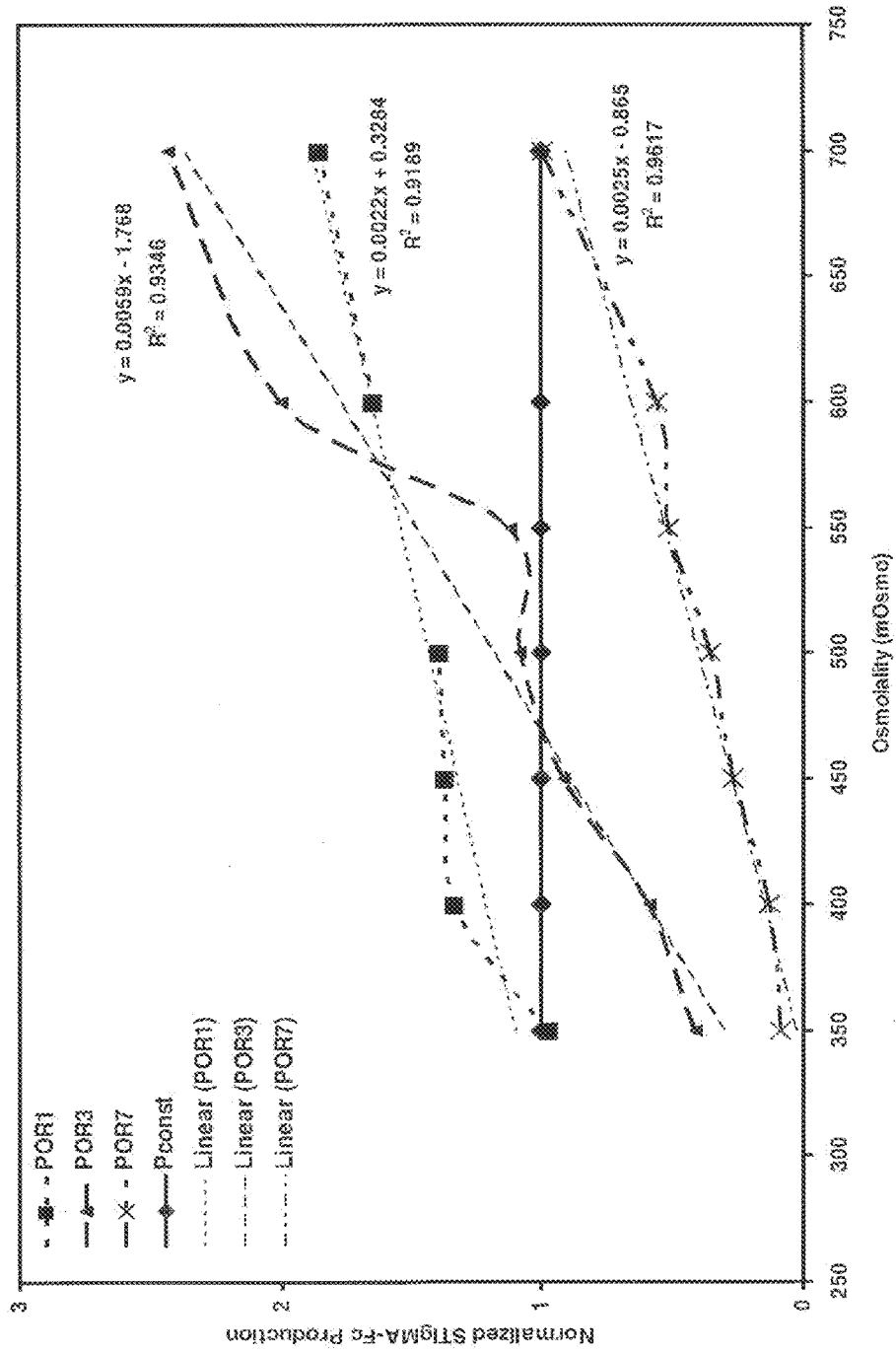
FIG. 5 schematically illustrates normalized the POR3- and POR7-driven expression levels with their constitutive expression levels, as described in detail in Example 1, below. Like reference symbols in the various drawings indicate like elements.

POR3-driven Fc fusion expression levels were half of their counterpart constitutive expression levels in isotonic medium, as illustrated in FIG. 4. As medium osmolality increased from 300 mOsm to 500 mOsm, POR3 driven expression increased to a peak of 1.5 times isotonic expression levels and then decreased with osmolality from 500 mOsm until 700 mOsm.

POR7-driven Fc fusion expression levels were fifteen times lower then their constitutive expression counterparts in isotonic medium, as illustrated in FIG. 4. As osmolality increased from 300 mOsm to 550 mOsm POR7-driven Fc fusion expression levels increased to a maximum of four times isotonic expression levels and then decreased with osmolality. Data is normalized in FIG. 5.

Conclusion

The more (higher number of) osmo-responsive elements are encoded (inserted) within osmo-responsive transcriptional regulatory elements (OR-TREs) (also called "hybrid osmo-responsive promoters") of this invention, the less the level of transgene expression in isotonic medium—but the higher their induction factor (the ratio of its maximal expression levels by isotonic expression levels). Thus, we have constructed a set of osmo-responsive promoters that yield a variety of transgene expression windows and induction factors; and the invention provides a variety of osmo-responsive transcriptional regulatory elements (OR-TREs) having one or a plurality of osmo responsive elements engineered into the construct; for example, having one or a plurality of tonicity enhancer-binding protein (TonEBP)-responsive transcriptional enhancer sequences (TonEBP-binding motifs) and as alternative embodiments, also optionally having on or a plurality of AP-1 protein binding sites (AP-1 binding motifs).

Normalized Expression Levels

Data Analysis

The relative decrease in constitutive expression levels from isotonic to hypertonic expression is indicative of the osmo-related decrease in protein production due to inhibited cell growth and viability. Thus, we normalized the POR3- and POR7-driven expression levels with their constitutive expression levels; see FIG. 4.

Conclusion

This example presents data demonstrating how increasing the number of osmo-responsive elements encoded in the constructs of this invention (the osmo-responsive transcriptional regulatory element (OR-TRE) of this invention, or "osmo-responsive promoter") does lower isotonic expression levels in an osmo-responsive element number dependent manner. This example also presents data demonstrating that the actual transactivation level of these promoters by the exemplary constructs of this invention increases with osmolality in a linear manner from 350 mOsm to 700 mOsm.

Example 3: Osmo-Sensitive Transcriptional and Posttranscriptional Gene Modulation This example describes exemplary constructs of the invention having a combined osmo-sensitive transcriptional and posttranscriptional gene modulation; e.g., exemplary constructs of the invention able to positively upregulate both transcriptional and post-transcriptional expression levels of message and polypeptide, respectively, under osmotically stressed (e.g., high salt) conditions.

Alternative embodiments combine osmo-regulation with transcriptional controls and/or post-transcriptional (e.g., translational) level controls: (1) (at the transcriptional level) either an endogenous mammalian osmo-responsive promoter and/or a synthetic eukaryotic osmo-responsive promoter of this invention; and (2) (at the posttranscriptional level) by incorporation of one or more transcriptional or translational regulatory sequences or motifs. These controls can be incorporated (engineered) into a construct of the invention such that any message (transcript) generated from that construct has an osmo-sensitive 5' and/or 3' untranslated region; and in one embodiment, additional transcriptional and/or post-transcriptional (e.g., translational) level controls.

For example, the presence of transcriptional and/or post-transcriptional (e.g., translational) level control sequences or motifs generates an mRNA (a message) that is more stable and/or longer lasting, e.g., more stable and/or longer lasting in conditions of hyperosmolality (e.g., a hyperosmotic environment); thus resulting in increased recombinant protein expression in conditions of hyperosmolality, e.g., at high osmolalities. This embodiment boosts the regulation factor between basal expression in isotonic medium and maximal gene-induction in conditions of hyperosmolality, e.g., in hyperosmotic medium.

Example 4

The yield of recombinant protein production driven by a constitutive promoter steadily decreases as osmolality increases. We reasoned that the introduction of osmo-responsive element(s) in a constitutive promoter might further transactivate the constitutive promoter and counterbalance the negative effects of hypertonicity on recombinant protein production. In order to test this hypothesis, we introduced one, three or seven osmo responsive elements in between the enhancer of the human CMV promoter and $P_{fragment\ CMV}$.

Methods:

Construction of the Osmo-Responsive Promoters

The enhancer of the human CMV promoter was PCR amplified with oligos OLM401: 5'-CAAGCTTGACTAGT-CAATCAATTACGGGGTCATTAGTTCAT-3' (SEQ ID NO:38) and OLM400: 5'-AGCTAGCACACCGTA-CACGCCTACCG-3' (SEQ ID NO:39) (restriction sites in bold, annealing sequence in italic). The PCR product was digested with HindIII and NheI, $P_{OR1}$-Intron was excised from an intermediary plasmid (SpeI/EcoRI) both DNA fragments were cloned in another intermediary plasmid (HindIII/EcoRI) thus resulting in: PconstOR1-Intron: $E_{hCMV}OR1P_{fragment\ CMV}$-Intron. The same strategy was used to construct PconstOR3-Intron: $E_{hCMV}OR3P_{fragment\ CMV}$-Intron and PconstOR7-Intron: $E_{hCMV}OR7P_{fragment\ CMV}$-Intron.

PconstOR1 was excised from the intermediary plasmid (SpeI/ClaI) and cloned into pOsmoI (SpeI/ClaI) thus resulting into: pconstOsmo1 (PconstOR1-Intron-STIgMA-Fc-pA; PconstOR1: $E_{hCMV}$-$P_{OR1}$). The same strategy was used to construct pconstOsmo3 (PconstOR3-Intron-STIgMA-Fc-pA; PconstOR3: $E_{hCMV}$-$P_{OR3}$) and pconstOsmo7 (PconstOR7-Intron-STIgMA-Fc-pA; PconstOR7: $E_{hCMV}$-$P_{OR7}$) were constructed.

Cell Culture, Transfection

Chinese hamster ovary cells CHO-K1 DUX-B11 (dhfr-) were grown in suspension in a serum-free low protein (recombinant human insulin) medium. Optimized lipofectamin transfection protocols were used for high efficiency transient transfection of the cells. Transiently transfected cells were harvested 6 hours post transfection, and seeded in 6 well plates in serum containing medium at increasing osmolality. The osmolality of the medium was adjusted in each well by adding a fix volume of a phosphate buffer saline with increasing salt concentration. Transiently transfected cells were routinely analyzed with an Fc fusion gene expression assay performed by ELISA.

Results

In order to assess the impact of the introduction of an increasing number of osmo-responsive element 3' of the enhancer of the human cytomegalovirus promoter and 5' of the human cytomegalovirus promoter fragment, we constructed three promoters bearing either 1, 3 or 7 osmo-responsive elements cloned side by side: PconstOR1, PconstOR3, PconstOR7. CHO-K1 DUX-B11 (dhfr-) cells were transfected with an Fc fusion expression plasmid driven either by the human cytomegalovirus constitutive promoter or one of these engineered promoter. 6 hours post-transfection, the cells were harvested and seeded in medium of increasing osmolality.

Figure 6:
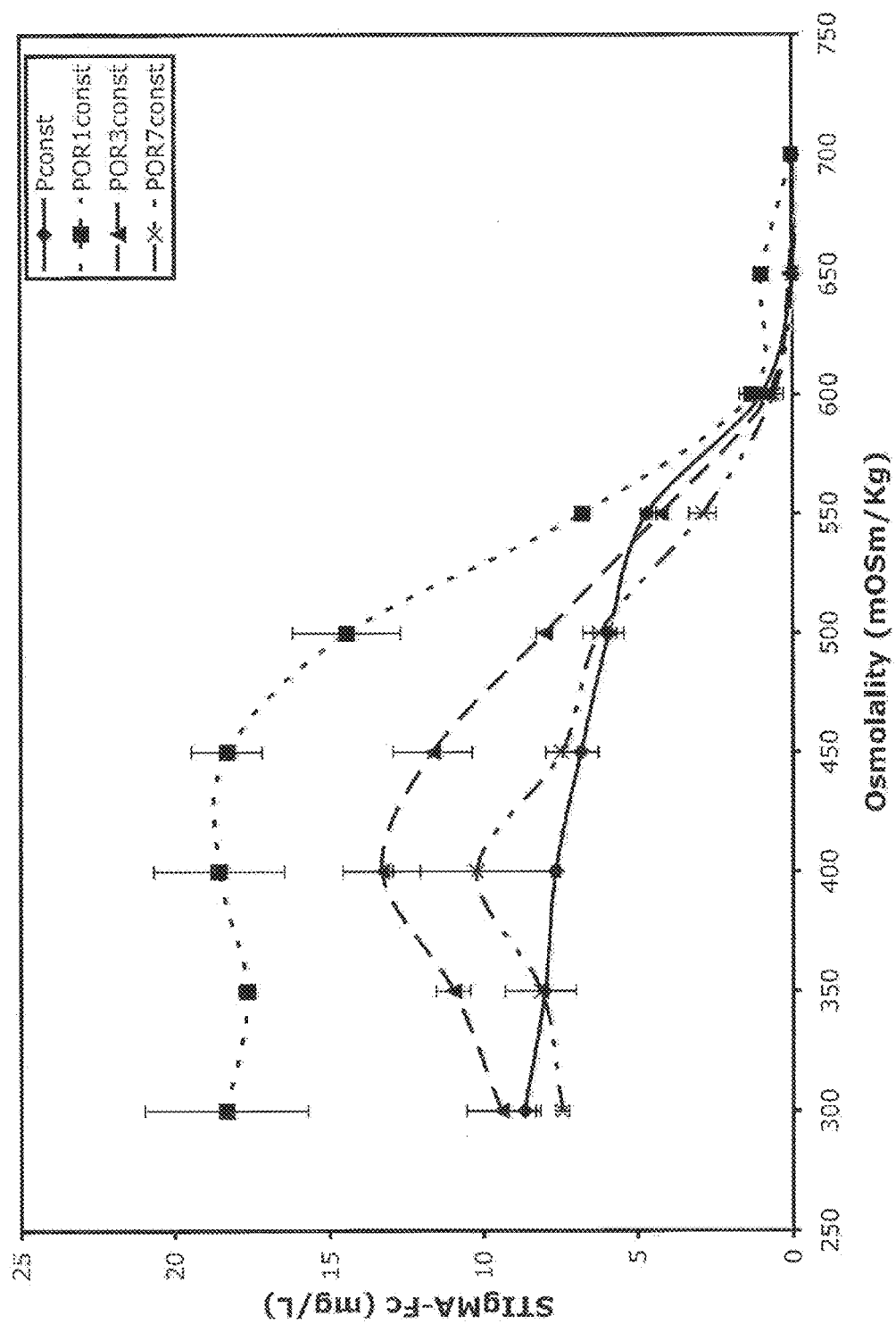
FIG. 6 shows the effects of one, three or seven ORE on protein production in hypertonic medium.

Constitutive expression of the reporter gene steadily decreased as osmolality increased (FIG. 6).

To our surprise introducing one osmo-responsive element in between the enhancer and the fragment of the CMV promoter led to a doubling of recombinant protein expression in isotonic medium. Between 300 mOsm/Kg and 450 mOsm/Kg the expression levels of the recombinant protein of interest driven by PconstOR1 were maintained at this high level and then decreased with osmolality from 500 mOsm/Kg until 700 mOsm/Kg.

The introduction of three osmo-responsive elements within the constitutive human CMV promoter led to a slight increase in recombinant protein expression compared to the wild-type CMV promoter at 300 mOsm/Kg. In contrast, the introduction of seven osmo-responsive elements led to a slight decrease of recombinant protein expression in isotonic medium. Fc fusion expression levels driven by the CMV promoter modified to contain either three or seven osmo-responsive elements increased from 300 mSom/Kg to 400 mOsm/Kg and then steadily decreased until 700 mOsm/Kg.

Conclusion

Introducing one osmo-responsive element within the human CMV promoter leads to double the recombinant protein expression levels at 300 mOsm/Kg. This was an unexpected result.

The presence of osmo-responsive elements enable to counterbalance the effects of increased osmolality on recombinant protein expression and when three or seven osmo-responsive elements are introduced recombinant expression levels are up-regulated with increasing osmolality to reach a maximum at 400 mOsm/Kg and then steadily decrease.

A number of embodiments of the invention have been described. Nevertheless, it will be understood that various modifications may be made without departing from the spirit and scope of the invention. Accordingly, other embodiments are within the scope of the following claims.

What is claimed is:

1. A method for expressing a recombinant protein in a cell under conditions of hyperosmolality, the method comprising:
   (A) introducing a first polynucleotide into the cell, wherein the first polynucleotide comprises:
      (i) a nucleic acid molecule encoding a tonicity enhancer binding protein (TonEBP) operatively linked to a first promoter, and
      (ii) a nucleic acid molecule encoding a first osmoresponsive transcriptional regulatory element (OR-TRE), wherein the first OR-TRE comprises the nucleic acid sequence of SEQ ID NO: 1 and the nucleic acid sequence of SEQ ID NO:3, wherein the nucleic acid molecule encoding the first OR-TRE is operatively linked to the first promoter,
   (B) introducing a second polynucleotide into the cell, wherein the second polynucleotide comprises:
      (i) a nucleic acid molecule encoding the recombinant protein operatively linked to a second promoter, and
      (ii) a nucleic acid molecule encoding a second OR-TRE, wherein the second OR-TRE comprises the nucleic acid sequence of SEQ ID NO: 1 and the nucleic acid sequence of SEQ ID NO:3, wherein the nucleic acid molecule encoding the second OR-TRE is operatively linked to the second promoter, and
   (C) culturing the cell under conditions wherein the TonEBP protein and the recombinant protein are expressed.

2. The method of claim 1, wherein the second polynucleotide further comprises the nucleic acid sequence of SEQ ID NO:2.

3. The method of claim 1, wherein the second polynucleotide further comprises the nucleic acid sequence of SEQ ID NO:4.

4. The method of claim 1, wherein the second polynucleotide further comprises the nucleic acid sequence of SEQ ID NO:5.

5. The method of claim 1, wherein the second polynucleotide further comprises one or more additional OR-TREs.

* * * * *